US010117899B2

(12) United States Patent
Genovese et al.

(10) Patent No.: US 10,117,899 B2
(45) Date of Patent: Nov. 6, 2018

(54) DELIVERY METHODS AND COMPOSITIONS FOR NUCLEASE-MEDIATED GENOME ENGINEERING IN HEMATOPOIETIC STEM CELLS

(71) Applicants: Sangamo BioSciences, Inc., Richmond, CA (US); Ospedale San Raffaele srl, Milan (IT); Fondazione Telethon, Rome (IT)

(72) Inventors: Pietro Genovese, Milan (IT); Philip D. Gregory, Richmond, CA (US); Michael C. Holmes, Richmond, CA (US); Angelo Leone Lombardo, Milan (IT); Luigi Naldini, Milan (IT)

(73) Assignees: Sangamo Therapeutics, Inc., Richmond, CA (US); Ospedale San Raffaele SRL, Milan (IT); Fondazione Telethon, Rome (IT)

( * ) Notice: Subject to any disclaimer, the term of this patent is extended or adjusted under 35 U.S.C. 154(b) by 271 days.

(21) Appl. No.: 14/516,189

(22) Filed: Oct. 16, 2014

(65) Prior Publication Data

US 2015/0174169 A1 Jun. 25, 2015

Related U.S. Application Data

(60) Provisional application No. 61/892,340, filed on Oct. 17, 2013.

(51) Int. Cl.

| | |
|---|---|
| ***C12N 5/10*** | (2006.01) |
| ***C12N 15/867*** | (2006.01) |
| ***C12N 15/90*** | (2006.01) |
| ***C12N 5/16*** | (2006.01) |
| ***C12N 5/0789*** | (2010.01) |
| ***A61K 35/28*** | (2015.01) |
| ***A61K 48/00*** | (2006.01) |
| ***C12N 9/22*** | (2006.01) |
| ***C12N 15/86*** | (2006.01) |
| *A61K 35/12* | (2015.01) |

(52) U.S. Cl.

CPC ............ *A61K 35/28* (2013.01); *A61K 48/005* (2013.01); *C12N 5/0647* (2013.01); *C12N 9/22* (2013.01); *C12N 15/86* (2013.01); *C12N 15/907* (2013.01); *A61K 48/00* (2013.01); *A61K 2035/124* (2013.01); *C12N 2510/00* (2013.01); *C12N 2740/16043* (2013.01)

(58) Field of Classification Search

CPC ...... C12N 15/907; C12N 15/85; C12N 15/86; C12N 2510/00; C12N 2740/16043; C12N 5/0647; C12N 9/22; A61K 35/28

USPC .................... 435/320.1, 325, 455; 424/93.21

See application file for complete search history.

(56) References Cited

U.S. PATENT DOCUMENTS

| | | | |
|---|---|---|---|
| 5,789,538 | A | 8/1998 | Rebar et al. |
| 5,925,523 | A | 7/1999 | Dove et al. |
| 6,007,988 | A | 12/1999 | Choo |
| 6,013,453 | A | 1/2000 | Choo |
| 6,140,081 | A | 10/2000 | Barbas |
| 6,140,466 | A | 10/2000 | Barbas, III et al. |
| 6,200,759 | B1 | 3/2001 | Dove et al. |
| 6,242,568 | B1 | 6/2001 | Barbas, III et al. |
| 6,410,248 | B1 | 6/2002 | Greisman et al. |
| 6,453,242 | B1 | 9/2002 | Eisenberg et al. |
| 6,479,626 | B1 | 11/2002 | Kim et al. |
| 6,503,717 | B2 | 1/2003 | Case et al. |
| 6,534,261 | B1 | 3/2003 | Cox, III et al. |
| 6,599,692 | B1 | 7/2003 | Case et al. |
| 6,607,882 | B1 | 8/2003 | Cox, III et al. |
| 6,689,558 | B2 | 2/2004 | Case |
| 6,794,136 | B1 | 9/2004 | Eisenberg et al. |
| 6,824,978 | B1 | 11/2004 | Cox, III et al. |
| 6,903,185 | B2 | 6/2005 | Kim et al. |
| 6,933,113 | B2 | 8/2005 | Case et al. |
| 6,979,539 | B2 | 12/2005 | Cox, III et al. |
| 7,013,219 | B2 | 3/2006 | Case et al. |
| 7,030,215 | B2 | 4/2006 | Liu et al. |
| 7,067,317 | B2 | 6/2006 | Rebar et al. |
| 7,070,934 | B2 | 7/2006 | Cox, III et al. |
| 7,153,949 | B2 | 12/2006 | Kim et al. |
| 7,163,824 | B2 | 1/2007 | Cox, III et al. |
| 7,253,273 | B2 | 8/2007 | Collingwood |
| 7,262,054 | B2 | 8/2007 | Jamieson et al. |
| 7,361,635 | B2 | 4/2008 | Miller et al. |
| 7,888,121 | B2 | 2/2011 | Urnov et al. |
| 7,914,796 | B2 | 3/2011 | Miller et al. |
| 7,951,925 | B2 | 5/2011 | Ando et al. |
| 7,972,854 | B2 | 7/2011 | Miller et al. |
| 8,034,598 | B2 | 10/2011 | Miller |
| 8,110,379 | B2 | 2/2012 | DeKelver et al. |

(Continued)

FOREIGN PATENT DOCUMENTS

| | | | |
|---|---|---|---|
| GB | 23388237 | A | 12/1999 |
| WO | WO 95/19431 | A1 | 7/1995 |

(Continued)

OTHER PUBLICATIONS

Lombardo et al. (2007) Nat. Biotech., vol. 25(11), 1298-1306.*

(Continued)

*Primary Examiner* — Anne Marie S Wehbe

(74) *Attorney, Agent, or Firm* — Pasternak Patent Law; Susan Abrahamson

(57) ABSTRACT

The present disclosure is in the field of genome engineering, particularly targeted modification of the genome of a hematopoietic cell.

11 Claims, 43 Drawing Sheets

Specification includes a Sequence Listing.

(56) References Cited

U.S. PATENT DOCUMENTS

| | | | |
|---|---|---|---|
| 8,329,986 B2 | 12/2012 | Butler et al. | |
| 8,399,218 B2 | 3/2013 | Gupta et al. | |
| 8,409,861 B2 | 4/2013 | Guschin et al. | |
| 8,563,314 B2 | 10/2013 | Gregory et al. | |
| 8,586,526 B2 | 11/2013 | Gregory et al. | |
| 8,623,618 B2 | 1/2014 | Doyon et al. | |
| 8,697,359 B1 | 4/2014 | Zhang | |
| 8,772,453 B2 | 7/2014 | Paschon et al. | |
| 2003/0232410 A1 | 12/2003 | Liljedahl et al. | |
| 2005/0026157 A1 | 2/2005 | Baltimore et al. | |
| 2005/0064474 A1* | 3/2005 | Urnov | C07K 14/43595 435/6.18 |
| 2005/0208489 A1 | 9/2005 | Carroll et al. | |
| 2005/0267061 A1 | 12/2005 | Martin | |
| 2006/0063231 A1 | 3/2006 | Li et al. | |
| 2006/0188987 A1 | 8/2006 | Guschin et al. | |
| 2007/0218528 A1 | 9/2007 | Miller | |
| 2008/0131962 A1 | 6/2008 | Miller | |
| 2008/0159996 A1 | 7/2008 | Ando et al. | |
| 2008/0299580 A1 | 12/2008 | DeKelver et al. | |
| 2009/0054985 A1 | 4/2009 | Anderson | |
| 2009/0068164 A1 | 4/2009 | Segal et al. | |
| 2010/0047805 A1 | 2/2010 | Wang | |
| 2010/0218264 A1 | 8/2010 | Cui et al. | |
| 2011/0027235 A1 | 2/2011 | Gregory et al. | |
| 2011/0201055 A1 | 8/2011 | Doyon et al. | |
| 2011/0207221 A1 | 8/2011 | Cost et al. | |
| 2011/0265198 A1 | 10/2011 | Gregory et al. | |
| 2011/0301073 A1 | 12/2011 | Gregory et al. | |
| 2012/0017290 A1 | 1/2012 | Cui et al. | |
| 2012/0060230 A1 | 3/2012 | Collingwood et al. | |
| 2013/0122591 A1 | 5/2013 | Cost et al. | |
| 2013/0137104 A1 | 5/2013 | Cost et al. | |
| 2013/0177960 A1 | 7/2013 | Rebar | |
| 2013/0177983 A1 | 7/2013 | Rebar | |
| 2015/0056705 A1 | 2/2015 | Conway et al. | |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/016536 A1 | 2/2002 |
| WO | WO 02/077227 A2 | 10/2002 |
| WO | WO 02/099084 A2 | 12/2002 |
| WO | WO 03/016496 A2 | 2/2003 |
| WO | WO 07/014275 A2 | 2/2007 |
| WO | WO 10/079430 A1 | 7/2010 |

OTHER PUBLICATIONS

Zou et al. (2011) Blood, vol. 117(21), 5561-5572.*

Takizawa et al. (2011) Swiss Medical Weekly, vol. 141:w11316, pp. 1-9.*

Beerli, et al., "Engineering Polydactyl Zinc-Finger Transcription Factors," *Nature Biotechnol*. 20:135-141(2002).

Biancotti, et al., "Increasing Hematopoetic Stem Cell Yield to Develop Mice With Human Immune Systems," *Biomed Res. Int*. Epub vol. 2013, Article ID 740892, 11 pages (2013).

Boch, et al., "Breaking the Code of DNA Binding Specificity of TAL-Type III Effectors," *Science* 326:1509-1512 (2009).

Bonas, et al., "Genetic and Structural Characterization of the Avirulence Gene AVRBS3 From Xanthomonas Campestris PV. Vesicatoria," *Mol. Gen. Genet*. 218:127-136 (1989).

Cannon, et al., "Electroporation of ZFN MRNA Enables Efficient CCR5 Gene Disruption in Mobilized Blood Hematopoietic Stem Cells at Clinical Scale," ASGCT 16$^{th}$ Annual Meeting, Abstract #183 (2013).

Choo, et al., "Advances in Zinc Finger Engineering," *Curr. Opin. Struct. Biol*. 10:411-416 (2000).

Christian, et al., "TAL Effector Nucleases Create Targeted DNA Double-Strand Breaks," *Genetics* epub 10.1534/genetics.110.120717.

Cong, et al., "Multiplex Genome Engineering Using CRISPR/CAS Systems," *Sciencexpress* 1/10.1126/science 1231143 (2013).

Dull, et al., "A Third-Generation Lentivirus Vector With a Conditional Packaging System," *J. Virol*. 72(11):8463-8471 (1998).

Follenzi, et al., "Gene Transfer by Lentiviral Vectors Is Limited by Nuclear Translocation and Rescued by HIV-1 POL Sequences," *Nature Genetics* 25:217-222 (2000).

Gabriel, et al., "An Unbiased Genome-Wide Analysis of Zinc-Finger Nuclease Specificity," *Nat. Biotech*. 29(9):816-823 (2011) doi: 10.1038/nbt.1948.

Genovese, et al., "Targeted Genome Editing in Human Repopulating Haematopoietic Stem Cells," *Nature* 510:235-240 (2014) doi:10.1038/nature13420.

Guo, et al., "Directed Evolution of an Enhanced and Highly Efficient Foki Cleavage Domain for Zinc Finger Nucleases," *J. Mol. Biol*. 400(1):96-107 (2010).

Haft, et al., "A Guild of 45 CRISPR-Associated (CAS) Protein Families and Multiple CRISPR/CAS Subtypes Exist in Prokaryotic Genomes," *PLoS Comput. Biol*. 1(6):474-483 (2005).

Heuer, et al., "Repeat Domain Diversity of AVRBS3-Like Genes in Ralstonia Solanacearum Strains and Association With Host Preferences in the Field," *Appl. and Envir. Micro*. 73(13):4379-4384 (2007).

Isalan, et al., "A Rapid, Generally Applicable Method to Engineer Zinc Fingers Illustrated by Targeting the HIV-1 Promoter," *Nat. Biotechnol*. 19:656-660 (2001).

Jansen, et al., "Identification of Genes That Are Associated With DNA Repeats in Prokaryotes," *Molecular Microbiology* 43(6):1565-1575 (2002).

Kay, et al., "A Bacterial Effector Acts as a Plant Transcription Factor and Induces a Cell Size Regulator," *Science* 318:648-651 (2007).

Kormann, et al., "Expression of Therapeutic Proteins After Delivery of Chemically Modified MRNA in Mice," *Nature Biotechnology* 29(2):154-157 (2011).

Lombardo, et al., "Gene Editing in Human Stem Cells Using Zinc Finger Nucleases and Integrase-Defective Lentiviral Vector Delivery," *Nat. Biotechnology* 25:1298-1306 (2007).

Lombardo, et al., "Site-Specific Integration and Tailoring of Cassette Design for Sustainable Gene Transfer," *Nature Methods* 8:861-869 (2011) doi:10.1038/nmeth.1674.

Makarova, et al., "A DNA Repair System Specific for Thermophilic Archaea and Bacteria Predicted by Genomic Context Analysis," *Nucleic Acids Res*. 30:482-496 (2002).

Makarova, et al., "A Putative RNA-Interference-Based Immune System in Prokaryotes: Computational Analysis of the Predicted Enzymatic Machinery, Functional Analogies With Eukaryotic RNAI, and Hypothetical Mechanisms of Action," *Biol. Direct* 1:7 (2006).

Moscou, et al., "A Simple Cipher Governs DNA Recognition by TAL Effectors," *Science* 326:1501 (2009).

Naldini, et al., "Efficient Transfer, Integration, and Sustained Long-Term Expression of the Transgene in Adult Rat Brains Injected With a Lentiviral Vector," *Proc. Natl. Acad. Sci. USA* 93:11382-11388 (1996).

Olovnikov, et al., "Bacterial Argonaute Samples the Transcriptome to Identify Foreign DNA," *Mol. Cell*. 51(51:594-605 (2013).

Pabo, et al., "Design and Selection of Novel CYS2HIS2 Zinc Finger Proteins," *Ann. Rev. Biochem*. 70:313-340 (2001).

Schornack, et al., "Gene-For-Gene-Mediated Recognition of Nuclear-Targeted AVRBS3-Like Bacterial Effector Proteins," *J. Plant Physiol*. 163(3):256-272 (2006).

Segal, et al., "Custom DNA-Binding Proteins Come of Age: Polydactyl Zinc-Finger Proteins," *Curr. Opin. Biotechnol*. 12:632-637 (2001).

(56) References Cited

OTHER PUBLICATIONS

Sheng, et al., "Structure-Based Cleavage Mechanism of Thermus Thermophilus Argonaute DNA Guide Strand-Mediated DNA Target Cleavage," *Proc. Natl. Acad. Sci. USA* 111(2):652-657 (2013) doi: 10.1073/pnas.1321032111.
Stella, et al., "CD34-Positive Cells: Biology and Clinical Relevance," *Haematologica* 80:367-387 (1995).
Swarts, et al., "DNA-Guided DNA Interference by a Prokaryotic Argonaute," *Nature* 507(7491):258-261 (2014).
Vogel, "A Bacterial Seek-And-Destroy System for Foreign DNA," *Science* 344(6187):972-973 (2014) doi: 10.1126/science.1252962.
Yuan, et al., "Crystal Structure of A. Aeolicus Argonaute, a Site-Specific DNA-Guided Endoribonuclease, Provides Insights Into Risc-Mediated MRNA Cleavage," *Molecular Cell* 19:405-419 (2005) doi: 10.1016/j.molcel.2005.07.011.
Zuffrey, et al., "Self-Inactivating Lentivirus Vector for Safe and Efficient In Vivo Gene Delivery," *J. Virol*. 72(12):9873-9880 (1998).
Coluccio, et al., "Targeted Gene Addition in Human Epithelial Stem Cells by Zinc-Finger Nuclease-Mediated Homologous Recombination," Molecular Therapy 21(9):1695-1704 (2013).
Provasi, et al., "Editing T Cell Specificity Towards Leukemia by Zinc Finger Nucleases and Lentiviral Gene Transfer," Nature Medicine 18(5):807-815 (2012).
Rio, et al., "Targeted Gene Therapy and Cell Reprogramming in Fanconi Anemia," Embo Molecular Medicine 6(6):835-848 (2014).
Torres, et al., "An Integration-Defective Lentivirus-Based Resource for Site-Specific Targeting of an Edited Safe-Harbour Locus in the Human Genome," Gene Therapy 21(4):343-352 (2014).

* cited by examiner

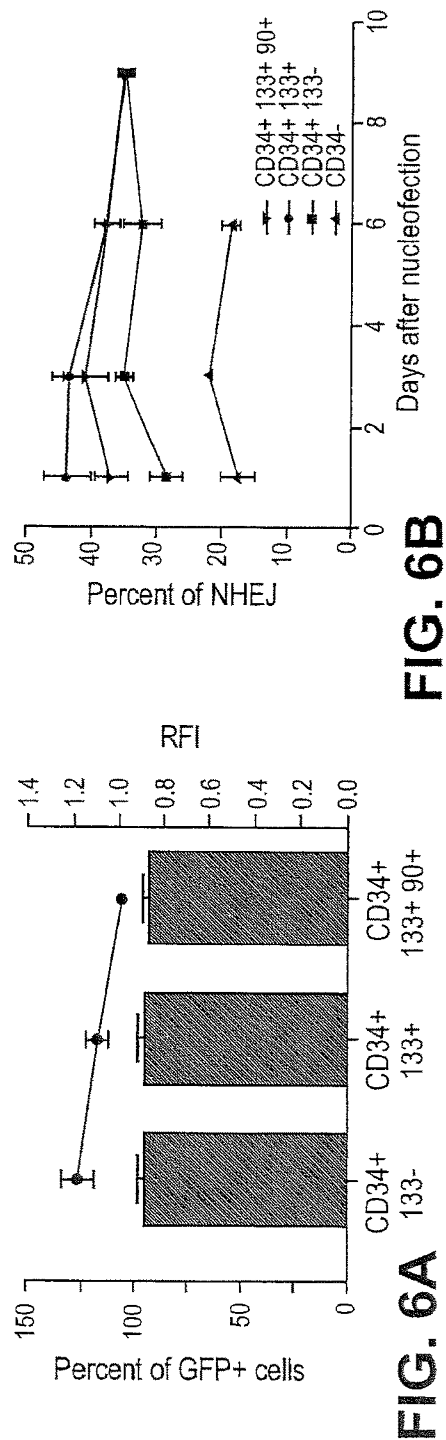
FIG. 6B
FIG. 6A
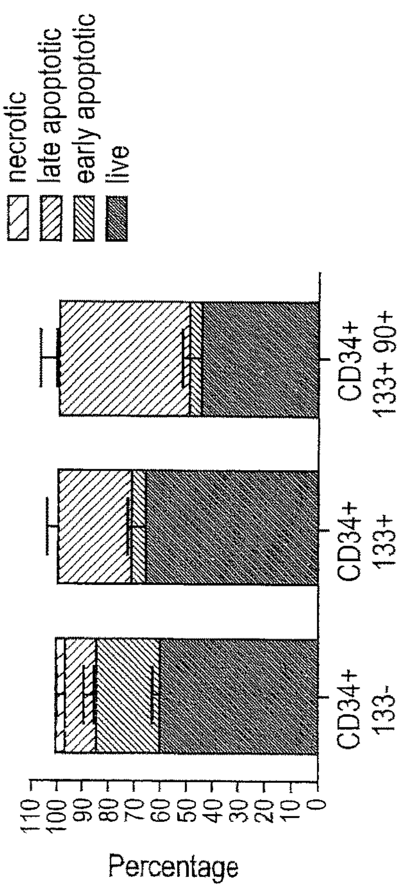
FIG. 6C

DELIVERY METHODS AND COMPOSITIONS FOR NUCLEASE-MEDIATED GENOME ENGINEERING IN HEMATOPOIETIC STEM CELLS

CROSS-REFERENCE TO RELATED APPLICATIONS

The present application claims the benefit of U.S. Provisional Application No. 61/892,340, filed Oct. 17, 2013, the disclosure of which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 11, 2014, is named 8325-0109SL.txt and is 5,059 bytes in size.

TECHNICAL FIELD

The present disclosure is in the field of genome engineering, particularly targeted modification of the genome of a hematopoietic cell.

BACKGROUND

Various methods and compositions for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20050064474; 20060063231; 201000218264; 20120017290; 20110265198; 20130137104; 20130122591; 20130177983; 20130177960 and 20150056705, the disclosures of which are incorporated by reference in their entireties for all purposes.

These methods often involve the use of engineered cleavage systems to induce a double strand break (DSB) or a nick in a target DNA sequence such that repair of the break by an error born process such as non-homologous end joining (NHEJ) or repair using a repair template (homology directed repair or HDR) can result in the knock out of a gene or the insertion of a sequence of interest (targeted integration). Cleavage can occur through the use of specific nucleases such as engineered zinc finger nucleases (ZFN), transcription-activator like effector nucleases (TALENs), or using the CRISPR/Cas system with an engineered crRNA/tracr RNA ('single guide RNA') to guide specific cleavage.

Targeted cleavage using one of the above mentioned nuclease systems can be exploited to insert a nucleic acid into a specific target location using either HDR or NHEJ-mediated processes. However, delivering both the nuclease system and the donor to the cell can be problematic. For example, delivery of a donor or a nuclease via transduction of a plasmid into the cell can be toxic to the recipient cell, especially to a cell which is a primary cell and so not as robust as a cell from a cell line.

CD34+ stem or progenitor cells are a heterogeneous set of cells characterized by their ability to self-renew and/or differentiate into the cells of the lymphoid lineage (e.g. T cells, B cells, NK cells) and myeloid lineage (e.g. monocytes, erythrocytes, eosinophiles, basophiles, and neutrophils). Their heterogeneous nature arises from the fact that within the CD34+ stem cell population, there are multiple subgroups which often reflect the multipotency (whether lineage committed) of a specific group. For example, CD34+ cells that are CD38− are more primitive, immature CD34+ progenitor cell, (also referred to as long term hematopoietic progenitors), while those that are CD34+CD38+ (short term hematopoietic progenitors) are lineage committed (see Stella et at (1995) *Hematologica* 80:367-387). When this population then progresses further down the differentiation pathway, the CD34 marker is lost. CD34+ stem cells have enormous potential in clinical cell therapy. However, in part due to their heterogeneous nature, performing genetic manipulations such as gene knock out, transgene insertion and the like upon the cells can difficult. Specifically, these cells are poorly transduced by conventional delivery vectors, the most primitive stem cells are sensitive to modification, there is limited HDR following induced DNA DSBs, and there is insufficient hematopoietic stem cell (HSC) maintenance in prolonged standard culture conditions.

Thus, there remains a need for compositions and methods for genome engineering to CD34+ cells that are less toxic and more efficient.

SUMMARY

The present invention describes compositions and methods for use in gene therapy and genome engineering. Specifically, the methods and compositions described relate to introducing nucleic acids into hematopoietic stem cells/progenitor cells (HSCs/PCs).

In some aspects, the invention comprises delivery of at least one nuclease to an HSC/PC for the purpose of genome engineering. In some embodiments, the nuclease is delivered as a peptide, while in others it is delivered as a nucleic acid encoding the nuclease. In some embodiments, more than one nuclease is used. In some preferred embodiments, the nucleic acid encoding the nuclease is an mRNA, and in some instances, the mRNA is protected and/or chemically modified (see e.g. Kormann et al, (2011) *Nature Biotechnology* 29(2):154-157). The nuclease may comprise a zinc finger nuclease (ZFN), a TALE-nuclease (TALEN), a CRISPR/Cas or TtAgo nuclease system or a combination thereof. In a preferred embodiment, the nucleic acid encoding the nuclease(s) is delivered via electroporation.

In certain embodiments, provided herein is a method of integrating one or more transgenes into a genome of an isolated cell, the method comprising: (a) introducing a donor vector comprising the one or more transgenes into the cell; (b) culturing the cell for less than 48 hours; and (c) introducing at least one nuclease into the cell, wherein the at least one nuclease cleaves the genome of the cell such that the one or more transgenes are integrated into the genome of the cell. The method steps may be repeated for integration of additional transgenes into the same and/or different loci. In certain embodiments, the cell is cultured (step (b)) for less than 24 hours. In certain embodiments, the nuclease(s) can be introduced before introduction of the donor vector within 4 hours. Any cell can be used, for example, a hematopoietic stem cell (e.g., CD34+ cell) or T-cell (e.g., CD4+ or CD8+ cell). The nuclease (e.g., ZFN, TALEN, TtAgo and/or CRISPR/Cas) may also be introduced using viral or non-viral vectors, for example in mRNA form. In certain embodiments, the nuclease targets a safe-harbor gene (e.g., a CCR5 gene, an AAVS1 gene, a *Rosa* gene, an albumin gene, etc.). The transgene may encode a protein, for example a therapeutic protein that is lacking or deficient in a subject with a disorder (e.g., lysosomal storage disease, hemoglobinopathy, hemophilia, severe immunodeficiency disorder etc.). In certain embodiments, a method of providing one or more proteins to a subject in need thereof is described, the method comprising: introducing one or more transgenes encoding the one or more proteins into an isolated cell according to any of the methods described herein and introducing the cell into the subject such that the one or more proteins are provided to the subject.

In other aspects, the invention comprises delivery of a donor nucleic acid to a target cell. The donor may be delivered prior to, after, or along with the nucleic acid encoding the nuclease(s). In certain embodiments, the donor is delivered simultaneously with the nuclease(s). In other embodiments, the donor is delivered prior to the nuclease(s), including any time before, for example, immediately before, 1 to 60 minutes before (or any time therebetween), 1 to 24 hours before (or any time therebetween), 1 to 48 hours (or any time therebetween) or more than 48 hours before. In certain embodiments, the donor is delivered after the nuclease, preferably within 4 hours. The donor nucleic acid comprises an exogenous sequence (transgene) to be integrated into the genome of the cell, for example, an endogenous locus. The transgene is preferably integrated at or near (e.g., within 1-50 base pairs) of the site of cleavage by the nuclease(s). In some embodiments, the donor comprises a full length gene or fragment thereof flanked by regions of homology with the targeted cleavage site. In some embodiments, the donor lacks homologous regions and is integrated into a target locus through homology independent mechanism (i.e. NHEJ). In other embodiments, the donor comprises a smaller piece of nucleic acid flanked by homologous regions for use in the cell (i.e. for gene correction). In some embodiments, the donor comprises a gene encoding a functional or structural component such as a shRNA, RNAi, miRNA, or the like. In other embodiments the donor comprises a gene encoding a regulatory element that binds to and/or modulate expression of a gene of interest. In other aspects, the donor is delivered by viral and/or non-viral gene transfer methods. In preferred embodiments, the donor is delivered to the cell via a lentiviral vector (LV). In some embodiments the lentiviral vector is derived from HIV. In some embodiments, the LV is not capable of integrating into the host cell's genome (IDLV). In some embodiments the IDLV is produced using a mutant defective integrase. The donor may be delivered using the same gene transfer system as used to deliver the nuclease (including on the same vector) or may be delivered using a different delivery system that is used for the nuclease. In certain embodiments, the donor is delivered using a viral vector (e.g., LV) and the nuclease(s) is (are) delivered in mRNA form.

The sequence of interest of the donor molecule may comprise one or more sequences encoding a functional polypeptide (e.g., a cDNA), with or without a promoter. In certain embodiments, the nucleic acid sequence comprises a sequence encoding an antibody, an antigen, an enzyme, a growth factor, a receptor (cell surface or nuclear), a hormone, a lymphokine, a cytokine, a reporter, functional fragments of any of the above and combinations of the above. In embodiments in which the functional polypeptide encoding sequences are promoterless, expression of the integrated sequence is then ensured by transcription driven by an endogenous promoter or other control element in the region of interest. In other embodiments, a "tandem" cassette is integrated into the selected site in this manner, the first component of the cassette comprising a promoterless sequence as described above, followed by a transcription termination sequence, and a second sequence, encoding an autonomous expression cassette. Additional sequences (coding or non-coding sequences) may be included in the donor molecule between the homology arms, including but not limited to, sequences encoding a 2A peptide, SA site, IRES, etc.

In another aspect, described herein are methods of integrating a donor nucleic acid into the genome of a cell via homology-independent mechanisms. The methods comprise creating a double-stranded break (DSB) in the genome of a cell and cleaving the donor molecule using a nuclease, such that the donor nucleic acid is integrated at the site of the DSB. In certain embodiments, the donor nucleic acid is integrated via non-homology dependent methods (e.g., NHEJ). As noted above, upon in vivo cleavage the donor sequences can be integrated in a targeted manner into the genome of a cell at the location of a DSB. The donor sequence can include one or more of the same target sites for one or more of the nucleases used to create the DSB. Thus, the donor sequence may be cleaved by one or more of the same nucleases used to cleave the endogenous gene into which integration is desired. In certain embodiments, the donor sequence includes different nuclease target sites from the nucleases used to induce the DSB. DSBs in the genome of the target cell may be created by any mechanism. In certain embodiments, the DSB is created by one or more zinc-finger nucleases (ZFNs), fusion proteins comprising a zinc finger binding domain, which is engineered to bind a sequence within the region of interest, and a cleavage domain or a cleavage half-domain. In other embodiments, the DSB is created by one or more TALE DNA-binding domains (naturally occurring or non-naturally occurring) fused to a nuclease domain (TALEN). In yet further embodiments, the DSB is created using a CRISPR/Cas or TtAgo nuclease system where an engineered single guide RNA or its functional equivalent is used as needed to guide the nuclease to a targeted site in a genome. In other aspects, the nuclease(s) binds to and/or cleaves a safe-harbor gene, for example a CCR5 gene, a PPP1R12C (also known as AAVS1) gene, a *Rosa* gene or an albumin gene in mammalian cells. In addition, to aid in selection in mammalian systems, the HPRT locus may be used.

In other aspects, provided herein is a cell which has been genetically modified (e.g., transgenic) as described herein, for example using a nuclease to introduce the genetic modification. In certain embodiments, the cell is made by the methods described herein. In certain embodiments, the cell comprises a transgene that is integrated into a safe-harbor locus, such as CCR5, AAVS1, ALB, Rosa26 and/or HPRT. The cells comprising the integrated transgene may express the transgene from an endogenous promoter or, alternatively, the transgene may include regulatory and control elements such as exogenous promoters that drive expression of the transgene (e.g., when integrated into a safe harbor locus). In certain embodiments, the cells comprising the transgene do not include any viral vector sequences integrated into the genome. The cells may be any eukaryotic cell, for example CD34+ stem cells (e.g., patient-derived stem cells mobilized in patients from the bone marrow into the peripheral blood via granulocyte colony-stimulating factor (GCSF) or other mobilizing agent administration or harvested directly from the bone marrow or umbilical cords). The cells can be harvested, purified, cultured, and the nucleases and/or donor introduced into the cell by any suitable method.

Compositions such as pharmaceutical compositions comprising the genetically modified cells as described herein are also provided. In some embodiments, the compositions comprise CD34+ HSC/PC or HSC/PC cell population. In other embodiments, the compositions comprise T cells (e.g. CD4+ and/or CD8+ T cells). In still further embodiments, the T cell compositions comprise only CD4+ or only CD8+ cells.

In another aspect, provided are methods of using the genetically modified cells as described herein. In some aspects, genetically modified blood cell precursors ("HSC/PC") are given in a bone marrow transplant and the HSC/PC differentiate and mature in vivo. In some embodiments, the HSC/PC are isolated following G-CSF-induced mobilization, and in others, the cells are isolated from human bone marrow or umbilical cords. In some aspects, the HSC/PC are edited by treatment with a nuclease designed to knock out a specific gene or regulatory sequence. In other aspects, the HSC/PC are modified with an engineered nuclease and a donor nucleic acid such that a wild type gene or other gene of interest is inserted and expressed and/or an endogenous aberrant gene is corrected. In some embodiments, the modified HSCs/PC are administered to the patient following mild myeloablative pre-conditioning. In other aspects, the HSC/PC are administered after full myeloablation such that following engraftment, 100% of the hematopoietic cells are derived from the modified HSC/PC. Furthermore, the cell may be arrested in the G2 phase of the cell cycle.

In some embodiments, the nuclease and LV comprising the donor are given to the CD34+ population using a precise temporal methodology. In some embodiments, the methodology includes a prolonged target cell stimulation to achieve greater efficiency of modification. In still further embodiments, the target cells are treated with compounds known to preserve stemness of the cells to prevent cell differentiation during transduction. In some embodiments, the preservative compound used is Aryl Hydrocarbon Receptor Antagonist (StemRegenin 1, SR1), while in others, 16.16 dimethylprostaglandin E2 (dmPGE2) is used, and in some embodiments, a combination of the two are used.

In some embodiments, the transgenic HSC/PC cell and/or animal includes a transgene that encodes a human gene. In some instances, the transgenic animal comprises a knock out at the endogenous locus corresponding to exogenous transgene, thereby allowing the development of an in vivo system where the human protein may be studied in isolation. Such transgenic models may be used for screening purposes to identify small molecules or large biomolecules or other entities which may interact with or modify the human protein of interest. In some aspects, the transgene is integrated into the selected locus (e.g., safe-harbor) into a stem cell (e.g., an embryonic stem cell, an induced pluripotent stem cell, a hematopoietic stem or precursor cell, etc.) or animal embryo obtained by any of the methods described herein, and then the embryo is implanted such that a live animal is born. The animal is then raised to sexual maturity and allowed to produce offspring wherein at least some of the offspring comprise edited endogenous gene sequence or the integrated transgene.

A kit, comprising the LVs and nucleic acids of the invention, is also provided. The kit may comprise nucleic acids encoding the nucleases, (e.g. RNA molecules or ZFN, TALEN or CRISPR/Cas system encoding genes contained in a suitable expression vector), or aliquots of the nuclease proteins, donor molecules, suitable stemness modifiers, instructions for performing the methods of the invention, and the like. The kit may also comprise donor molecules of interest such as selection or screening markers.

These and other aspects will be readily apparent to the skilled artisan in light of disclosure as a whole.

BRIEF DESCRIPTION OF THE DRAWINGS

FIG. 1A is a schematic representation of the IDLV template for HDR containing a GFP expression cassette (driven by the phosphoglycerate kinase promoter, PGK) flanked by sequences homologous to the genomic target locus (light gray lines, "homology arms"); the target locus with the ZFNs cleavage site is indicated; the locus after HDR showing the PCR primers used to assay targeted integration (black arrows). FIG. 1B is a task oriented flow chart for gene targeting and cell analyses. FIG. 1C shows Cord Blood (CB)-derived CD34+ cells were transduced with donors as shown in FIG. 1A with IDLV templates comprising homology arms specific for AAVS1 or IL2RG and, one day later, electroporated (+ZFNs) or not (Donor only) with ZFNs mRNAs specific for each locus. As additional control, cells were transduced with IDLV carrying unrelated homology arms to the ZFN target site ("Unrelated donor"). Cells were analyzed for GFP expression by flow cytometry three days after electroporation. The top of FIG. 1C shows a representative flow cytometry dot plots where percentages of GFP+ cells and Mean Fluorescence Intensities (MFI) in arbitrary units are indicated. The bottom of FIG. 1C is a histogram showing the percentage of GFP+ cells measured by flow cytometry three days after electroporation (light gray bar) and the percent of non-homologous end joining (NHEJ) measured by Cell assay at the target locus ten days after treatment (black bar). The data shown are means±SEM (AAVS1, n=39 on 19 CB donors; IL2RG, n=10 on 9 CB donors) "nd" indicates not detectable, "np": not performed. FIG. 1D depicts the results from the treated cells from FIG. 1C after being assessed by PCR for targeted integration into AAVS1 by primers amplifying the 5' or 3' HDR-mediated integration junctions. This representative analysis was performed on the bulk (left) and FACS-sorted GFP positive and negative cells (right) where the PCR products were electrophoresed on a gel as shown. "NTC" indicates no template control. FIG. 1E shows a Southern blot (top) and a gel of a PCR experiment (bottom, as in FIG. 1D) analyses of genomic DNA extracted from the expanded outgrowth of iPSC clones obtained by reprogramming CD34+ cells sorted for GFP expression ten days after gene targeting. Shown on the left are the data for AAVS1 targeting and on the right shows the data for IL2RG targeting. Southern blot analysis was performed following restriction enzyme digestion where the probes were made against regions outside of the homology arms included in the vectors. All analyzed GFP+ clones (AAVS1, n=1; IL2RG, n=4) displayed targeted integration (TI) of the cassette. "UT" means untreated cells. FIG. 1F depicts representative growth curves of CD34+ cells transduced with IDLV and electroporated with ZFNs mRNAs (TI), transduced only (IDLV), or untreated (UT). FIG. 1G is a histogram showing the percentages of live (7AAD−, AnnexinV−), early apoptotic (7AAD−, AnnexinV+), late apoptotic (7AAD+, AnnexinV+) and necrotic (7AAD+, AnnexinV−) CD34+ cells one day after the indicated treatments. The data shown are means±SEM from 2 independent experiments. FIG. 1H depicts Colony Forming Cells (CFC) from CD34+ cells treated as indicated. The data shown are means±SEM from 3 independent experiments. FIG. 1I on the left depicts representative bright field and fluorescence microscopy images of GFP+ erythroid and myeloid colonies. Scale bar, 0.5 mm. On the right side of FIG. 1I is a histogram showing the percentage of GFP+ cells measured in liquid culture three days after the gene targeting procedure and on the corresponding GFP+ colonies counted in CFC assay two weeks after plating. Data shown are means±SEM (n=32 for liquid culture and n=85 for CFC; experiment performed on 7 CB donors). ns: not significant (unpaired t test). FIG. 1J shows targeting specificity in CFC. Genomic DNA from GFP+ colonies was analyzed by PCR for targeted integration into AAVS1 or IL2RG (top panel). Bars represent percentage of colonies positive for both 5' and 3' integration junctions (integration by HDR), for either a 5' or 3' junction (integration by HDR+NHEJ) or negative for both (Unknown) at the indicated target site. Numbers of colonies screened are indicated on top of the bars. The bottom gels show PCR amplicons for the target and a control locus (CCR5). FIGS. 1K and 1L show the efficiency of different gene delivery platforms in CD34+ cells. FIG. 1K shows CD34+ cells that were pre-stimulated with early acting cytokines for 24 hr and then transduced with GFP-encoding IDLV (MOI: $5\times10^{2}$) or Adenoviral Vector serotype 5/35 (MOI: $5\times10^{3}$); or electroporated with GFP-expressing mRNA (500 μg/ml) or plasmid DNA (25 μg/ml). The cells were analyzed by flow cytometry at the indicated days after the procedure. Representative density plots of GFP expression 24 hours post treatment. "UT" indicates untreated cells. FIG. 1L shows kinetics of transgene expression measured as percentage of GFP+ cells (left) and relative GFP fluorescence intensity (RFI, measured as the ratio between the mean fluorescence intensity of the treated cells at each time point to the untreated cells) in arbitrary units.

FIG. 2A shows end point analyses performed 12-23 weeks post-transplant on peripheral blood (PB), spleen and bone marrow (BM). The left panels show percentages of human CD45+ cells in the indicated organs and the right panel shows percentages of the indicated cell populations within the human CD45+ cells. B, myeloid, T cells and erythroid progenitors were defined by expression of CD19, CD33 or CD13, CD3 and CD235a respectively. Dots represent individual mice. Mean±SEM are shown (n=42; 6 independent experiments performed on 13 CB donors). FIG. 2B shows a time course of engraftment by human GFP+ cells in the PB of mice from a representative experiment. Mice were analyzed every 2 weeks for the percentage of GFP+ cells within circulating human CD45+ cells. Dashed lines represent mice in which GFP+ cells were no longer detectable 12 weeks post-transplant. Continuous lines represent mice with long-term engrafted GFP+ cells. n=5 CB donors. FIG. 2C shows the percentages of GFP+ cells among the human graft in the indicated organs at the end of the experiment (left panel) and the percentages of GFP+ cells within the indicated cell populations (right panel), as in FIG. 2A. Only mice harboring GFP+ cells above an arbitrary threshold of 0.1%, 12 weeks post-transplant are represented in the graphs (n=18; 6 independent experiments performed on 13 CB donors). FIG. 2D shows percentages of GFP+ cells (right) within primitive and committed human progenitors in the mouse BM, defined according to the CD34 and CD38 markers (boxed on left). FIG. 2E shows human lymphoid (CD19+) and myeloid (CD33+ and CD13+) cells sorted from BM and spleen and CD34+ progenitors sorted from BM that were analyzed by PCR for targeted integration into AAVS1. The same analysis was performed on GFP+ colonies plated from BM-derived CD34+ cells. FIG. 2F shows representative bright field and fluorescence microscopy images of the GFP+ lymphoid and myeloid cells in FIG. 2E. Scale bars, 0.5. FIG. 2G shows percentages of NHEJ at AAVS1 and IL2RG ZFNs target sites measured by Cell assay on genomic DNA from total BM cells.

FIG. 3A depicts the gating strategy used to identify subpopulations of CB cells according to expression of CD90, CD133 and CD34 surface markers. FIG. 3B shows a histogram following flow cytometry analyses of cells three days after the gene targeting procedure, when GFP becomes detectable. Bars represent percentages of GFP+ cells measured within the indicated subpopulations. The left most panel shows results of the protocol described in FigurelB. Other panels refer to protocols using longer prestimulation and/or the indicated drugs, as shown in the schematic in FIG. 3C. Data shown are means±SEM (n=31, 15, 14, 15, 7, and 5 respectively on 37 total CB donors). *p<0.05; *p<0.001 (one-way Anova with Bonferroni's multiple comparison post-test). FIG. 3D shows the composition of CD34+ cell cultures treated or not with SR1 over time according to the subpopulations indicated in the legend of FIG. 3B. Means±SEM (n=4 different CB donors). FIG. 3E shows a histogram of the total (left) and GFP+(right) colonies from CD34+ cells treated for gene targeting in medium supplemented with or without SR1. Data shown are means±SEM (n=20, 14). FIG. 3F is a histogram that shows the yield of GFP+ primitive progenitors (CD133+) relative to that obtained using the original protocol of FigurelB. Data shown are means±SEM (n=8, 7, 11, 10, 3, and 5, from left to right in the figure) p<0.01 (one-way Anova with Bonferroni's multiple comparison post-test). FIG. 3G shows data for CD34+ cells treated with the indicated targeting protocols that were injected in NSG mice. The histogram shows the percentage of mice that scored positive for GFP+ cells at 14 weeks post-transplant. FIG. 3H shows a time course of engraftment of human CD45+ cells treated with the indicated protocols in PB. Data shown are means±SEM (24 h SR1, n=5; 48 h SR1, n=6; 48 h, n=5) **p<0.0001, *p<0.001 (two-way Anova). FIG. 3I shows percentages of GFP+ cells within CD45+ cells treated with the indicated protocols in the PB at 14 weeks post-transplant. Only mice scored as GFP positive are shown. Data shown are means±SEM (n=3 independent experiments). Mice transplanted with the cells for the 24 hours under no SR1 condition are shown for comparison from FIG. 2C. FIG. 3J is a graph showing cell numbers after days in culture following treatment with the indicated reagents.

FIG. 4A is a schematic representation of the IL2RG donor template, in which a promoter-less partial IL2RGcDNA and a PGK-GFP expression cassette are flanked by sequences homologous to those surrounding the ZFNs target site in the endogenous IL2RG locus. HDR-mediated targeted integration knocks-in the cDNA so that its expression is driven from the endogenous IL2RG promoter. Boxed numbers indicate exons. FIG. 4B shows a flow chart of a transplantation experiment in NSG mice, including a tumor challenge and the resultant analyses. FIG. 4C, left panel, shows the percentage of human CD45+ cells in the PB of mice transplanted with male CD34+ cells treated as indicated for IL2RG targeting.

Analyses performed at the time just prior to tumor injection (top panel) and three weeks later (bottom panel). The right panel shows the percentages of T and NK cells (CD3+ and CD 16/56+ cells, respectively) measured within the human CD45+ cells derived from the indicated treatment groups in PB. FIG. 4D shows the fold change in the absolute number of the indicated lineages in the cells derived from the indicated treatment groups in transplanted mouse PB 3 weeks after tumor challenge. Data shown are means±SEM (24 h SR1, n=5; 48 h SR1, n=6; 48 h, n=5). FIG. 4E shows the fold expansion of T and NK cells, comparing the GFP− and GFP+ cells. FIG. 4F shows representative density plots of γ-chain expressing T cells (top) and NK cells (bottom) from PB that show GFP marking. (n=4,9 respectively). FIG. 4G depicts the percent of NHEJ in the IL2RG gene measured by Cell assay on CD34+ cells kept in liquid culture ten days after electroporation and on the human Lin+ myeloid and lymphoid progeny sorted from the BM and spleen of transplanted mice. FIG. 4H shows ex vivo growth of GFP+ and GFP− T cells sorted from the spleen of transplanted mice and stimulated with anti-CD3/28 beads in medium supplemented with IL7 and ILLS (n=4). FIG. 4I depicts Southern blot (top) and PCR (bottom) analyses showing targeted integration of the corrective IL2RGcDNA in T cells from transplanted mice, sorted according to GFP expression. "UT" indicates untreated cells. FIG. 4J shows tumor growth (left) and tumor weight, three weeks after challenge (right), in mice transplanted (n=16) or not (n=3) with treated CD34+ cells. ****p<0.0001 (two-way Anova and unpaired t test, respectively).

FIG. 5A (top) is a schematic representation (not in scale) of a plasmid DNA template used for in vitro mRNA transcription with the T7 promoter, the Kozak sequence (SEQ ID NO: 21) and the XbaI restriction enzyme used for the plasmid linearization depicted. The protein domains of a ZFN are shown in its open reading frame (ORF). NLS: nuclear localization signal; ZFP: Zinc Finger Protein; FokI: FokI nuclease domain. Representative denaturing gel electrophoresis of in vitro transcribed mRNAs encoding for the pair of ZFNs specific for AAVS1, before (−) and after (pA) enzymatic polyadenylation is shown in the bottom left panel. The ZFN mRNAs were produced either as two separated transcripts (ZFN-L and ZFN-R) or as a single construct encoding for both ZFNs linked by a Tav.2A self-cleavage peptide sequence (ZFN-L.2A.ZFN-R; Middle). The bottom right panel shows nuclease activity in CB-derived CD34+ cells that were electroporated either with the two separate transcripts or with the single mRNA co-expressing both ZFNs. ZFN activity was measured on treated cells as percentage of NHEJ detected at the ZFN target site by Cell assay 10 days after electroporation. FIG. 5B shows dose optimization of ZFNs mRNA delivery in CD34+ cells. CB-derived CD34+ cells were transduced with GFP expressing donor IDLV and then electroporated with the indicated escalating doses of mRNA (left panel). Percentages of GFP+ cells measured by flow cytometry 3 days after treatment. The percentages of viable cells (indicated on top of the histogram) were calculated as percentages of 7AAD negative cells gated on singlets. mRNA dose-response for ZFNs activity (percent NHEJ) as measured by Cell assay at day 10 post electroporation (right panel). Data shown are means±SEM (n=3). A dose dependent increase in the percentage of NHEJ and GFP+ cells was observed for the first three mRNA doses, whereas the highest dose caused a significant reduction in the number of viable cells, which probably negatively impacted the efficiency of gene targeting. Based on these data, we selected the dose of 175 μg/ml RNA to perform all the experiments. FIG. 5C shows CB-derived CD34+ cells were either transduced with the GFP-AAVS1 donor IDLV and electroporated with the cognate ZFNs mRNAs, or co-electroporated with GFP-AAVS1 donor plasmid DNA and ZFNs mRNAs. (Left) Cell viability was measured by flow cytometry three days after electroporation, comparing untreated cells (UT) and gene targeted cells using IDLV or plasmid as donor templates. ****p<0.0001 (one-way Anova with Bonferroni's multiple comparison post-test). (Right) Percentage of GFP+ cells using either donor templates. Data shown are means±SEM (UT, n=3; IDLV, n=18; Plasmid, n=10). *p<0.05 (unpaired t-test). FIG. 5D shows optimization of the schedule for ZFNs and donor template delivery to CD34+ cells. After one day of prestimulation, CB-derived CD34+ cells were first transduced with the AAVS1 donor IDLV and then electroporated at the indicated hours post-infection with ZFNs mRNAs (Left) or, first electroporated with ZFNs mRNAs and then transduced with IDLV donor (Right). The time lines of the experiments are shown on the top of FIG. 5D. The percentages of GFP+ cells measured by flow cytometry three days after treatment and NHEJ measured by Cell assay ten days after treatment are shown on bottom left where the percentage of GFP+ cells is shown on the left of each doublet in the histogram and the percent NHEJ detected in shown on the right. On the bottom right, the percentage of GFP+ cells is expressed as fold to the percentage achieved in the same experiment with the best strategy on the left.

FIGS. 6A through 6C show investigation of lower gene targeting in the more primitive cells. FIG. 6A depicts flow cytometry of GFP+CD34+ cells, after 24 hr of prestimulation, electroporated with GFP mRNA at the same dose used for one ZFN mRNA and AAVS1-specific ZFN mRNA. Flow cytometry analysis was performed two days later using the gating strategy shown in FIG. 3A. Bars represent the percentage of GFP+ cells (plotted on left axis) while the line shows the level of transgene expression (plotted on the right axis as MFI, measured in arbitrary units). Data shown are means±SEM (n=16 on 6 CB donors). FIG. 6B shows FACS analysis of gene targeted GFP+CD34+ cells FACS sorted one day after electroporation according to the gating strategy showed in FIG. 3A. The sorted populations were sampled at the indicated times and levels of NHEJ at the ZFN target site (AAVS1) were determined by Cell assay (n=3). FIG. 6C shows results of apoptosis analysis performed one day after electroporation on CD34+ cells transduced with GFP-AAVS1 donor IDLV and electroporated with ZFNs mRNAs. Percentages of live (7AAD−, AnnexinV−), early apoptotic (7AAD−, AnnexinV+), late apoptotic (7AAD+, AnnexinV+) and necrotic (7AAD+, AnnexinV−) cells. Data shown are means±SEM (n=5 on 4 CB donors).

FIG. 7A shows the percentage of the indicated lineages within the human cells in the PB of transplanted mice 14 weeks post-transplant. Data shown are means±SEM (48 h, n=3; 48 h SR1, n=5; 48 h PGE2, n=3; 48 h PGE2 SR1, n=6). Overall, the addition of SR1 and PGE2 to the in vitro culture did not significantly affect the in vivo differentiation of treated cells. Notably, the increased human engraftment achieved with the optimized culture conditions (as illustrated in FIG. 3H) correlates with increased T cell development. FIG. 7B shows multi-lineage GFP marking in individual NSG mice transplanted with CD34+ cells treated using the indicated protocols for targeted integration. Percentages of GFP+ cells were calculated within the CD45+ Lin+ populations (represented with different shapes of dots) in different organs (represented by different dots colors). The analysis was performed on PB at 14 weeks post transplantation and on spleen and BM at the end of the experiments. Only mice displaying greater than or equal to 0.1% GFP+ cells were scored as GFP positive and are represented in the graph. (n=2 independent experiments). Note that with the improved gene targeting protocols for targeted integration, all GFP+ mice harbor multilineage GFP+ cells. FIG. 7C shows analysis of the primitive human compartment in the BM of transplanted mice from FIG. 7B. The analysis was performed 14 weeks post-transplant in NSG mice injected with CD34+ cells treated with the indicated gene targeting protocols. (Left) Gating strategy used to define progenitors (CD34+ CD38+), MLPs (CD34+ CD38− CD90lo/− CD45RA+), MPPs (CD34+ CD38− CD90− CD45RA−) and HSCs (CD34+ CD38− CD90+ CD45RA−). (Right) Percentages of GFP+ cells measured within the populations defined on the left. Data shown are means±SEM (48 h SR1, n=4; 48 h PGE2, n=3; 48 h PGE2 SR1, n=5). FIG. 7D shows genomic DNA from total BM cells of transplanted mice was analyzed by PCR to determine targeted integration into IL2RG. Each lane represents one mouse (Left). (Right) Schematics of the different sets of primers used to detect on target insertions mediated by HDR or NHEJ (with the vector in sense or reverse orientation with respect to IL2RG).

FIG. 8A shows results from the interferon regulatory factor 7 (IRF7) gene; FIG. 8B shows results from the 2'-5'-oligoadenylate synthetase 1 (OAS1) gene and FIG. 8C shows results from the retinoic acid-inducible gene 1 (RIG1) gene. As shown, the gene targeting procedure described herein strongly upregulates IFN-I signaling.

In FIG. 11A, the left-most bar shows results in CD34− cells; the bar second from the left shows results in CD34+ CD133− cells; the bar second from the right shows results in CD34+ CD133+ cells and the right-most bar shows results in CD34+ CD133+ CD90+ cells.

DETAILED DESCRIPTION

Figure 1A:
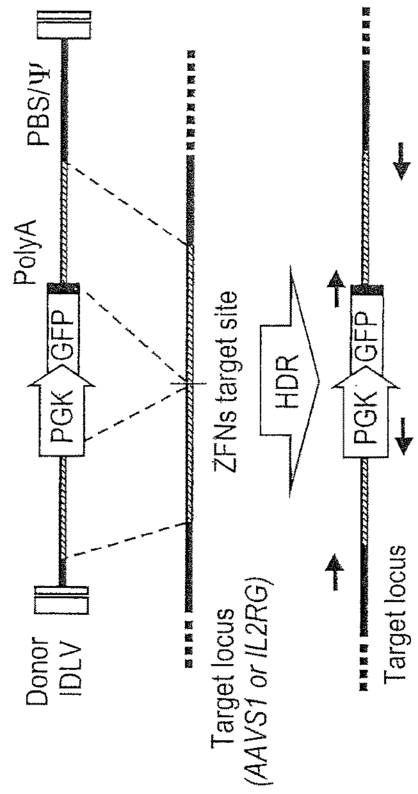
FIGS. 1A through 1L show targeted integration into AAVS1 or IL2RGin CD34+ cells.

Disclosed herein are compositions and methods for nuclease-mediated (e.g., NHEJ or HDR capture) targeted integration of a transgene.

In one aspect, the present invention provides a method for targeted integration into purified hematopoietic stem cells (HSC) and/or progenitor cells (PC), said method comprising the following steps: (a) delivering a donor nucleic acid to the HSC and/or PC cells; (b) culturing the cells obtained by step (a); and (c) delivering at least one nuclease to the cells obtained by step (b) such that the donor nucleic acid is integrated into the genome. In some embodiments, the method further comprises treating the HSC and/or PC cells with a compound that preserves stemness of the cells, preferably with an aryl Hydrocarbon Receptor Antagonist such as StemRegenin 1 (SR1) and/or 16.16 dimethyl-prostaglandin E2 (dmPGE2). In certain embodiments the method comprises delivering the donor nucleic acid to the HSC and/or PC cells by viral and/or non-viral gene transfer, preferably by a lentiviral vector (LV) gene transfer, more preferably by a non integrating lentiviral vector (IDLV) gene transfer. In particular embodiments, the method comprises delivering at least one nuclease of step (c) by electroporation. In some embodiments, the donor nucleic acid is an exogenous sequence, preferably an exogenous sequence flanked by regions of homology to an endogenous locus, more preferably an exogenous sequence flanked by regions of homology to an endogenous safe harbor locus or a locus downstream the regulatory regions of an endogenous gene. In some embodiments, the at least one nuclease is selected from the group comprising a zinc finger nuclease (ZFN), a TALE-nuclease (TALEN), Ttago nuclease system, a CRISPR/Cas nuclease or a combination thereof. In some embodiments, the HSC and/or PC cells are selected from the group comprising CD34+ cells, CD34+CD133+ cells, CD34+CD133− cells, CD34+CD133+CD90+ cells, or a combination thereof. In particular embodiments, the method comprises the following steps: (a) infecting the HSC and/or PC cells with an IDLV vector comprising an exogenous sequence flanked by regions of homology to an endogenous locus; (b) culturing the cells of step (a) for 1 to 3 days; and (c) electroporating mRNA encoding a pair of zinc finger nucleases (ZFNs) specific for the endogenous locus into the cells of step (b) such that the exogenous sequence is integrated into the endogenous locus. In some embodiments, the exogenous sequence is integrated into an endogenous safe harbor locus or downstream the regulatory regions of an endogenous gene, such that expression of the exogenous sequence is driven by the endogenous regulatory regions. In certain embodiments the HSC and/or PC cells are selected from the group comprising CD34+ cells, CD34+CD133+ cells, CD34+CD133− cells and CD34+CD133+CD90+ cells, or combination thereof. In further aspects, the present invention provides a genetically modified HSC or PC or a population of genetically modified HSCs and/or PCs obtainable by the method of the invention. In further aspects, the present invention provides a pharmaceutical composition comprising the genetically modified HSC or PC or population of genetically modified HSCs and/or PCs of the invention and a pharmaceutically acceptable carrier, excipient or diluents. In further aspects, the genetically modified HSC or PC or population of genetically modified HSCs and/or PCs of the invention or the pharmaceutical composition of the invention are used in therapy. In various embodiments, the present invention provides a method of engrafting genetically modified HSCs and/or PCs into a host organism, the method comprising administering the HSCs and/or PCs or population or the pharmaceutical composition of the invention to the host organism.

In particular, nuclease-mediated (i.e. ZFN, TALEN or CRISPR/Cas system) targeted integration of an exogenous sequence is efficiently achieved in a CD34+ HSC/PC. Efficiency of HSC/PC modification is achieved through using a lentiviral delivery system for the transgene and mRNA delivery of the nuclease. Additionally, cell stimulators and the transducing reagents are administered in a tightly controlled temporal fashion, and stemness preservation reagents may be added to prevent cell differentiation during the transduction method.

Delivery of ZFNs and donor template DNA was optimized as detailed and cell types include any hematopoietic stem cell or precursor cell, including CD34+ cells. The methods described herein result in long-term multilineage engraftment in animals treated with the modified cells.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

DEFINITIONS

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

A "TALE DNA binding domain" or "TALE" is a polypeptide comprising one or more TALE repeat domains/units. The repeat domains are involved in binding of the TALE to its cognate target DNA sequence. A single "repeat unit" (also referred to as a "repeat") is typically 33-35 amino acids in length and exhibits at least some sequence homology with other TALE repeat sequences within a naturally occurring TALE protein. See, e.g., U.S. Pat. No. 8,586,526;

Zinc finger and TALE binding domains can be "engineered" to bind to a predetermined nucleotide sequence, for example via engineering (altering one or more amino acids) of the recognition helix region of a naturally occurring zinc finger or TALE protein. Therefore, engineered DNA binding proteins (zinc fingers or TALEs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP and/or TALE designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication No. 20110301073.

A "selected" zinc finger protein or TALE is a protein not found in nature whose production results primarily from an empirical process such as phage display, interaction trap or hybrid selection. See e.g., U.S. Pat. Nos. 8,586,526; 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197, WO 02/099084.

"TtAgo" is a prokaryotic Argonaute protein thought to be involved in gene silencing. TtAgo is derived from the bacteria *Thermus thermophilus*. See, e.g., Swarts et al, ibid, G. Sheng et al., (2013) *Proc. Natl. Acad. Sci. U.S.A.* 111, 652). A "TtAgo system" is all the components required including, for example, guide DNAs for cleavage by a TtAgo enzyme.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair mechanisms. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

In the methods of the disclosure, one or more targeted nucleases as described herein create a double-stranded break in the target sequence (e.g., cellular chromatin) at a predetermined site, and a "donor" polynucleotide, having homology to the nucleotide sequence in the region of the break, can be introduced into the cell. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another.

In any of the methods described herein, additional pairs of zinc-finger proteins or TALEN can be used for additional double-stranded cleavage of additional target sites within the cell.

Any of the methods described herein can be used for insertion of a donor of any size and/or partial or complete inactivation of one or more target sequences in a cell by targeted integration of donor sequence that disrupts expression of the gene(s) of interest. Cell lines with partially or completely inactivated genes are also provided.

Furthermore, the methods of targeted integration as described herein can also be used to integrate one or more exogenous sequences. The exogenous nucleic acid sequence can comprise, for example, one or more genes or cDNA molecules, or any type of coding or noncoding sequence, as well as one or more control elements (e.g., promoters). In addition, the exogenous nucleic acid sequence may produce one or more RNA molecules (e.g., small hairpin RNAs (shRNAs), inhibitory RNAs (RNAis), microRNAs (miRNAs), etc.).

In certain embodiments of methods for targeted recombination and/or replacement and/or alteration of a sequence in a region of interest in cellular chromatin, a chromosomal sequence is altered by homologous recombination with an exogenous "donor" nucleotide sequence. Such homologous recombination is stimulated by the presence of a double-stranded break in cellular chromatin, if sequences homologous to the region of the break are present.

In any of the methods described herein, the exogenous nucleotide sequence (the "donor sequence" or "transgene") can contain sequences that are homologous, but not identical, to genomic sequences in the region of interest, thereby stimulating homologous recombination to insert a non-identical sequence in the region of interest. Thus, in certain embodiments, portions of the donor sequence that are homologous to sequences in the region of interest exhibit between about 80 to 99% (or any integer therebetween) sequence identity to the genomic sequence that is replaced. In other embodiments, the homology between the donor and genomic sequence is higher than 99%, for example if only 1 nucleotide differs as between donor and genomic sequences of over 100 contiguous base pairs. In certain cases, a non-homologous portion of the donor sequence can contain sequences not present in the region of interest, such that new sequences are introduced into the region of interest. In these instances, the non-homologous sequence is generally flanked by sequences of 50-1,000 base pairs (or any integral value therebetween) or any number of base pairs greater than 1,000, that are homologous or identical to sequences in the region of interest. In other embodiments, the donor sequence is non-homologous to the first sequence, and is inserted into the genome by non-homologous recombination mechanisms.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain). See, also, U.S. Patent Publication Nos. 2005/0064474, 20070218528, 2008/0131962 and 2011/0201055, incorporated herein by reference in their entireties.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 100,000,000 nucleotides in length (or any integer value therebetween or thereabove), preferably between about 100 and 100,000 nucleotides in length (or any integer therebetween), more preferably between about 2000 and 20,000 nucleotides in length (or any value therebetween) and even more preferable, between about 5 and 15 kb (or any value therebetween).

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity using standard techniques. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods known in the art. Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. An exogeneous molecule can also be the same type of molecule as an endogenous molecule but derived from a different species than the cell is derived from. For example, a human nucleic acid sequence may be introduced into a cell line originally derived from a mouse or hamster.

By contrast, an "endogenous" molecule is one that is normally present in a particular cell at a particular developmental stage under particular environmental conditions. For example, an endogenous nucleic acid can comprise a chromosome, the genome of a mitochondrion, or other organelle, or a naturally-occurring episomal nucleic acid. Additional endogenous molecules can include proteins, for example, transcription factors and enzymes.

As used herein, the term "product of an exogenous nucleic acid" includes both polynucleotide and polypeptide products, for example, transcription products (polynucleotides such as RNA) and translation products (polypeptides).

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP or TALE DNA-binding domain and one or more activation domains) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression. Genome editing (e.g., cleavage, alteration, inactivation, activation, random mutation) can be used to modulate expression. Gene inactivation refers to any reduction in gene expression as compared to a cell has not been modified as described herein (e.g., by a ZFP, TALE and/or CRISPR/Cas system). Gene inactivation may be partial or complete.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

"Eukaryotic" cells include, but are not limited to, fungal cells (such as yeast), plant cells, animal cells, mammalian cells and human cells (e.g., T-cells).

"Secretory tissues" are those tissues in an animal that secrete products out of the individual cell into a lumen of some type which are typically derived from epithelium. Examples of secretory tissues that are localized to the gastrointestinal tract include the cells that line the gut, the pancreas, and the gallbladder. Other secretory tissues include the liver, tissues associated with the eye and mucous membranes such as salivary glands, mammary glands, the prostate gland, the pituitary gland and other members of the endocrine system. Additionally, secretory tissues include individual cells of a tissue type which are capable of secretion.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP, TALE or Cas DNA-binding domain is fused to an activation domain, the ZFP, TALE or Cas DNA-binding domain and the activation domain are in operative linkage if, in the fusion polypeptide, the ZFP, TALE of Cas DNA-binding domain portion is able to bind its target site and/or its binding site, while the activation domain is able to upregulate gene expression. When a fusion polypeptide in which a ZFP, TALE or Cas DNA-binding domain is fused to a cleavage domain, the ZFP, TALE or Cas DNA-binding domain and the cleavage domain are in operative linkage if, in the fusion polypeptide, the ZFP, TALE or Cas DNA-binding domain portion is able to bind its target site and/or its binding site, while the cleavage domain is able to cleave DNA in the vicinity of the target site (e.g., 1 to 500 base pairs or any value therebetween on either side of the target site).

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one or more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

A "vector" is capable of transferring gene sequences to target cells. Typically, "vector construct," "expression vector," and "gene transfer vector," mean any nucleic acid construct capable of directing the expression of a gene of interest and which can transfer gene sequences to target cells. Thus, the term includes cloning, and expression vehicles, as well as integrating vectors.

A "reporter gene" or "reporter sequence" refers to any sequence that produces a protein product that is easily measured, preferably although not necessarily in a routine assay. Suitable reporter genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence. "Expression tags" include sequences that encode reporters that may be operably linked to a desired gene sequence in order to monitor expression of the gene of interest.

A "safe harbor" locus is a locus within the genome wherein a gene may be inserted without any deleterious effects on the host cell. Most beneficial is a safe harbor locus in which expression of the inserted gene sequence is not perturbed by any read-through expression from neighboring genes. Non-limiting examples of safe harbor loci in mammalian cells are the AAVS1, HPRT, albumin and CCR5 genes in human cells, and Rosa26 in murine cells (see, e.g., U.S. Pat. Nos. 7,888,121; 7,972,854; 7,914,796; 7,951,925; 8,110,379; 8,409,861; 8,586,526; U.S. Patent Publications Nos.20030232410; 20050208489; 20050026157; 20060063231; 20080159996; 201000218264; 20120017290; 20110265198; 20130137104; 20130122591; 20130177983 and 20130177960) and the Zp15 locus in plants (see U.S. Pat. No. 8,329,986).

The terms "subject" and "patient" are used interchangeably and refer to mammals such as human patients and non-human primates, as well as experimental animals such as rabbits, dogs, cats, rats, mice, and other animals. Accordingly, the term "subject" or "patient" as used herein means any mammalian patient or subject to which the or stem cells of the invention can be administered. Subjects of the present invention include those that have been exposed to one or more chemical toxins, including, for example, a nerve toxin.

"Stemness" refers to the relative ability of any cell to act in a stem cell-like manner, i.e., the degree of toti-, pluri-, or oligopotentcy and expanded or indefinite self-renewal that any particular stem cell may have.

Nucleases

Described herein are compositions, particularly nucleases, such as TALEs, homing endonucleases, CRISPR/Cas and/or Ttago guide RNAs, that are useful for in vivo cleavage of a donor molecule carrying a transgene and nucleases for cleavage of the genome of a cell such that the transgene is integrated into the genome in a targeted manner. In certain embodiments, one or more of the nucleases are naturally occurring. In other embodiments, one or more of the nucleases are non-naturally occurring, i.e., engineered in the DNA-binding domain and/or cleavage domain. For example, the DNA-binding domain of a naturally-occurring nuclease may be altered to bind to a selected target site (e.g., a meganuclease that has been engineered to bind to site different than the cognate binding site). In other embodiments, the nuclease comprises heterologous DNA-binding and cleavage domains (e.g., zinc finger nucleases; TAL-effector domain DNA binding proteins; meganuclease DNA-binding domains with heterologous cleavage domains). In other embodiments, the nuclease comprises a system such as the CRISPR/Cas or Ttago system.

A. DNA-binding Domains

In certain embodiments, the composition and methods described herein employ a meganuclease (homing endonuclease) DNA-binding domain for binding to the donor molecule and/or binding to the region of interest in the genome of the cell. Naturally-occurring meganucleases recognize 15-40 base-pair cleavage sites and are commonly grouped into four families: the LAGLIDADG (SEQ ID NO:22) family, the GIY-YIG family, the His-Cyst box family and the HNH family. Exemplary homing endonucleases include I-SceI, I-CeuI, PI-PspI, PI-Sce, I-SceIV, I-CsmI, I-PanI, I-SceII, I-PpoI, I-SceIII, I-CreI, I-Tevl, I-TevII and I-TevIII. Their recognition sequences are known. See also U.S. Pat. Nos. 5,420,032; 6,833,252; Belfort et al. (1997) Nucleic Acids Res.25:3379-3388; Dujon et al. (1989) Gene 82:115-118; Perler et al. (1994) Nucleic Acids Res. 22, 1125-1127; Jasin (1996) Trends Genet.12:224-228; Gimble et al. (1996) J. Mol. Biol. 263:163-180; Argast et al. (1998) J. Mol. Biol. 280:345-353 and the New England Biolabs catalogue.

In certain embodiments, the methods and compositions described herein make use of a nuclease that comprises an engineered (non-naturally occurring) homing endonuclease (meganuclease). The recognition sequences of homing endonucleases and meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S. Pat. Nos. 5,420,032; 6,833,252; Belfort et al. (1997) *Nucleic Acids Res.* 25:3379-3388; Dujon et al. (1989) *Gene* 82:115-118; Perler et al. (1994) *Nucleic Acids Res.* 22, 1125-1127; Jasin (1996) *Trends Genet.* 12:224-228; Gimble et al. (1996) *J. Mol.* Biol. 263:163-180; Argast et al. (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al. (2002) *Molec. Cell* 10:895-905; Epinat et al. (2003) *Nucleic Acids Res.* 31:2952-2962; Ashworth et al. (2006) *Nature* 441:656-659; Paques et al. (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

In other embodiments, the DNA-binding domain of one or more of the nucleases used in the methods and compositions described herein comprises a naturally occurring or engineered (non-naturally occurring) TAL effector DNA binding domain. See, e.g., U.S. Pat. No. 8,586,526, incorporated by reference in its entirety herein. The plant pathogenic bacteria of the genus *Xanthomonas* are known to cause many diseases in important crop plants. Pathogenicity of *Xanthomonas* depends on a conserved type III secretion (T3S) system which injects more than 25 different effector proteins into the plant cell. Among these injected proteins are transcription activator-like (TAL) effectors which mimic plant transcriptional activators and manipulate the plant transcriptome (see Kay et at (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et at (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack et at (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar 1 strain GMI1000 and in the biovar 4 strain RS1000 (See Heuer et at (2007) *Appl and Envir Micro* 73(13): 4379-4384). These genes are 98.9% identical in nucleotide sequence to each other but differ by a deletion of 1,575 by in the repeat domain of hpx17. However, both gene products have less than 40% sequence identity with AvrBs3 family proteins of *Xanthomonas*. See, e.g., U.S. Pat. No. 8,586,526, incorporated by reference in its entirety herein.

Specificity of these TAL effectors depends on the sequences found in the tandem repeats. The repeated sequence comprises approximately 102 by and the repeats are typically 91-100% homologous with each other (Bonas et al, ibid). Polymorphism of the repeats is usually located at positions 12 and 13 and there appears to be a one-to-one correspondence between the identity of the hypervariable diresidues (RVDs) at positions 12 and 13 with the identity of the contiguous nucleotides in the TAL-effector's target sequence (see Moscou and Bogdanove, (2009) *Science* 326:1501 and Boch et at (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al, ibid). Engineered TAL proteins have been linked to a FokI cleavage half domain to yield a TAL effector domain nuclease fusion (TALEN) exhibiting activity in a yeast reporter assay (plasmid based target). See, e.g., U.S. Patent Publication No. 20110301073; Christian et at ((2010)<Genetics epub 10.1534/genetics.110.120717).

In certain embodiments, the DNA binding domain of one or more of the nucleases used for in vivo cleavage and/or targeted cleavage of the genome of a cell comprises a zinc finger protein. Preferably, the zinc finger protein is non-naturally occurring in that it is engineered to bind to a target site of choice. See, for example, See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061, all incorporated herein by reference in their entireties.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; and WO 01/88197. In addition, enhancement of binding specificity for zinc finger binding domains has been described, for example, in co-owned WO 02/077227.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 8,772,453; 6,479,626; 6,903,185; and 7,153,949 for exemplary linker sequences-. The proteins described herein may include any combination of suitable linkers between the individual zinc fingers of the protein.

Selection of target sites; ZFPs and methods for design and construction of fusion proteins (and polynucleotides encoding same) are known to those of skill in the art and described in detail in U.S. Pat. Nos. 6,140,081; 5,789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

In certain embodiments, the DNA-binding domain is part of a CRISPR/Cas nuclease system. See, e.g., U.S. Pat. No. 8,697,359 and U.S. Patent Publication No. 20150056705. The CRISPR (clustered regularly interspaced short palindromic repeats) locus, which encodes RNA components of the system, and the cas (CRISPR-associated) locus, which encodes proteins (Jansen et al., 2002. Mol. Microbiol. 43: 1565-1575; Makarova et al., 2002. Nucleic Acids Res. 30: 482-496; Makarova et al., 2006. Biol. Direct 1: 7; Haft et al., 2005. PLoS Comput. Biol. 1: e60) make up the gene sequences of the CRISPR/Cas nuclease system. CRISPR loci in microbial hosts contain a combination of CRISPR-associated (Cas) genes as well as non-coding RNA elements capable of programming the specificity of the CRISPR-mediated nucleic acid cleavage.

The Type II CRISPR is one of the most well characterized systems and carries out targeted DNA double-strand break in four sequential steps. First, two non-coding RNA, the pre-crRNA array and tracrRNA, are transcribed from the CRISPR locus. Second, tracrRNA hybridizes to the repeat regions of the pre-crRNA and mediates the processing of pre-crRNA into mature crRNAs containing individual spacer sequences. Third, the mature crRNA:tracrRNA complex directs Cas9 to the target DNA via Watson-Crick base-pairing between the spacer on the crRNA and the protospacer on the target DNA next to the protospacer adjacent motif (PAM), an additional requirement for target recognition. Finally, Cas9 mediates cleavage of target DNA to create a double-stranded break within the protospacer. Activity of the CRISPR/Cas system comprises of three steps: (i) insertion of alien DNA sequences into the CRISPR array to prevent future attacks, in a process called 'adaptation', (ii) expression of the relevant proteins, as well as expression and processing of the array, followed by (iii) RNA-mediated interference with the alien nucleic acid. Thus, in the bacterial cell, several of the so-called 'Cas' proteins are involved with the natural function of the CRISPR/Cas system and serve roles in functions such as insertion of the alien DNA etc.

In certain embodiments, Cas protein may be a "functional derivative" of a naturally occurring Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity in common with a corresponding native sequence polypeptide. A biological activity contemplated herein is the ability of the functional derivative to hydrolyze a DNA substrate into fragments. The term "derivative" encompasses both amino acid sequence variants of polypeptide, covalent modifications, and fusions thereof. Suitable derivatives of a Cas polypeptide or a fragment thereof include but are not limited to, mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically or by a combination of these two procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In some embodiments, the DNA binding domain is part of a TtAgo system (see Swarts et al, ibid; Sheng et al, ibid). In eukaryotes, gene silencing is mediated by the Argonaute (Ago) family of proteins. In this paradigm, Ago is bound to small (19-31 nt) RNAs. This protein-RNA silencing complex recognizes target RNAs via Watson-Crick base pairing between the small RNA and the target and endonucleolytically cleaves the target RNA (Vogel (2014) *Science* 344: 972-973). In contrast, prokaryotic Ago proteins bind to small single-stranded DNA fragments and likely function to detect and remove foreign (often viral) DNA (Yuan et al., (2005) *Mol. Cell* 19, 405; Olovnikov et al. (2013) *Mol. Cell* 51, 594; Swarts et al., ibid). Exemplary prokaryotic Ago proteins include those from *Aquifex aeolicus, Rhodobacter sphaeroides*, and *Thermus thermophilus*.

One of the most well-characterized prokaryotic Ago protein is the one from *T. thermophilus* (TtAgo; Swarts et al. ibid). TtAgo associates with either 15 nt or 13-25 nt single-stranded DNA fragments with 5' phosphate groups. This "guide DNA" bound by TtAgo serves to direct the protein-DNA complex to bind a Watson-Crick complementary DNA sequence in a third-party molecule of DNA. Once the sequence information in these guide DNAs has allowed identification of the target DNA, the TtAgo-guide DNA complex cleaves the target DNA. Such a mechanism is also supported by the structure of the TtAgo-guide DNA complex while bound to its target DNA (G. Sheng et al., ibid). TtAgo from *Rhodobacter sphaeroides* (RsAgo) has similar properties (Olivnikov et al. ibid).

Exogenous guide DNAs of arbitrary DNA sequence can be loaded onto the TtAgo protein (Swarts et al. ibid.). Since the specificity of TtAgo cleavage is directed by the guide DNA, a TtAgo-DNA complex formed with an exogenous, investigator-specified guide DNA will therefore direct TtAgo target DNA cleavage to a complementary investigator-specified target DNA. In this way, one may create a targeted double-strand break in DNA. Use of the TtAgo-guide DNA system (or orthologous Ago-guide DNA systems from other organisms) allows for targeted cleavage of genomic DNA within cells. Such cleavage can be either single- or double-stranded. For cleavage of mammalian genomic DNA, it would be preferable to use of a version of TtAgo codon optimized for expression in mammalian cells. Further, it might be preferable to treat cells with a TtAgo-DNA complex formed in vitro where the TtAgo protein is fused to a cell-penetrating peptide. Further, it might be preferable to use a version of the TtAgo protein that has been altered via mutagenesis to have improved activity at 37 degrees Celsius. TtAgo-RNA-mediated DNA cleavage could be used to affect a panoply of outcomes including gene knock-out, targeted gene addition, gene correction, targeted gene deletion using techniques standard in the art for exploitation of DNA breaks.

Thus, the nuclease comprises a DNA-binding domain in that specifically binds to a target site in any gene into which it is desired to insert a donor (transgene).

B. Cleavage Domains

Any suitable cleavage domain can be operatively linked to a DNA-binding domain to form a nuclease. For example, ZFP DNA-binding domains have been fused to nuclease domains to create ZFNs—a functional entity that is able to recognize its intended nucleic acid target through its engineered (ZFP) DNA binding domain and cause the DNA to be cut near the ZFP binding site via the nuclease activity. See, e.g., Kim et al. (1996) *Proc Natl Acad Sci USA* 93(3):1156-1160. More recently, ZFNs have been used for genome modification in a variety of organisms. See, for example, U.S. Patent Publications 20030232410; 20050208489; 20050026157; 20050064474; 20060188987; 20060063231; and International Publication WO 07/014275. Likewise, TALE DNA-binding domains have been fused to nuclease domains to create TALENs. See, e.g., U.S. Pat. No. 8,586, 526.

As noted above, the cleavage domain may be heterologous to the DNA-binding domain, for example a zinc finger DNA-binding domain and a cleavage domain from a nuclease or a TALEN DNA-binding domain and a cleavage domain, or meganuclease DNA-binding domain and cleavage domain from a different nuclease. Heterologous cleavage domains can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotide pairs or more). In general, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer. Bitinaite et al. (1998) *Proc. Natl. Acad. Sci. USA* 95: 10,570-10,575. Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are described in U.S. Pat. No. 7,888,121, incorporated herein in its entirety. Additional restriction enzymes also contain separable binding and cleavage domains, and these are contemplated by the present disclosure. See, for example, Roberts et al. (2003) *Nucleic Acids Res.* 31:418-420.

In certain embodiments, the cleavage domain comprises one or more engineered cleavage half-domain (also referred to as dimerization domain mutants) that minimize or prevent homodimerization, as described, for example, in U.S. Pat. Nos. 8,772,453; 8,623,618; 8,409,861; 8,034,598; 7,914,796; and 7,888,121, the disclosures of all of which are incorporated by reference in their entireties herein. Amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains.

Exemplary engineered cleavage half-domains of FokI that form obligate heterodimers include a pair in which a first cleavage half-domain includes mutations at amino acid residues at positions 490 and 538 of FokI and a second cleavage half-domain includes mutations at amino acid residues 486 and 499.

Thus, in one embodiment, a mutation at 490 replaces Glu (E) with Lys (K); the mutation at 538 replaces Iso (I) with Lys (K); the mutation at 486 replaced Gln (Q) with Glu (E); and the mutation at position 499 replaces Iso (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. U.S. Pat. Nos. 7,914,796 and 8,034,598, the disclosures of which are incorporated by reference in their entireties. In certain embodiments, the engineered cleavage half-domain comprises mutations at positions 486, 499 and 496 (numbered relative to wild-type FokI), for instance mutations that replace the wild type Gln (Q) residue at position 486 with a Glu(E) residue, the wild type Iso (I) residue at position 499 with a Leu (L) residue and the wild-type Asn (N) residue at position 496 with an Asp (D) or Glu (E) residue (also referred to as a "ELD" and "ELE" domains, respectively). In other embodiments, the engineered cleavage half-domain comprises mutations at positions 490, 538 and 537 (numbered relative to wild-type FokI), for instance mutations that replace the wild type Glu (E) residue at position 490 with a Lys (K) residue, the wild type Iso (I) residue at position 538 with a Lys (K) residue, and the wild-type His (H) residue at position 537 with a Lys (K) residue or a Arg (R) residue (also referred to as "KKK" and "KKR" domains, respectively). In other embodiments, the engineered cleavage half-domain comprises mutations at positions 490 and 537 (numbered relative to wild-type FokI), for instance mutations that replace the wild type Glu (E) residue at position 490 with a Lys (K) residue and the wild-type His (H) residue at position 537 with a Lys (K) residue or a Arg (R) residue (also referred to as "KIK" and "KIR" domains, respectively). See, e.g., U.S. Pat. No. 8,772,453. In other embodiments, the engineered cleavage half domain comprises the "Sharkey" and/or "Sharkey' " mutations (see Guo et al, (2010) *J. Mol. Biol.* 400(1):96-107).

Engineered cleavage half-domains described herein can be prepared using any suitable method, for example, by site-directed mutagenesis of wild-type cleavage half-domains (Fok I) as described in U.S. Patent Publication Nos. 20050064474; 20080131962; and 20110201055.

Alternatively, nucleases may be assembled in vivo at the nucleic acid target site using so-called "split-enzyme" technology (see, e.g. U.S. Patent Publication No. 20090068164). Components of such split enzymes may be expressed either on separate expression constructs, or can be linked in one open reading frame where the individual components are separated, for example, by a self-cleaving 2A peptide or IRES sequence. Components may be individual zinc finger binding domains or domains of a meganuclease nucleic acid binding domain.

Nucleases can be screened for activity prior to use, for example in a yeast-based chromosomal system as described in U.S. Pat. No. 8,563,314. Expression of the nuclease may be under the control of a constitutive promoter or an inducible promoter, for example the galactokinase promoter which is activated (de-repressed) in the presence of raffinose and/or galactose and repressed in presence of glucose.

The Cas9 related CRISPR/Cas system comprises two RNA non-coding components: tracrRNA and a pre-crRNA array containing nuclease guide sequences (spacers) interspaced by identical direct repeats (DRs). To use a CRISPR/Cas system to accomplish genome engineering, both functions of these RNAs must be present (see Cong et al, (2013) *Sciencexpress* 1/10.1126/science 1231143). In some embodiments, the tracrRNA and pre-crRNAs are supplied via separate expression constructs or as separate RNAs. In other embodiments, a chimeric RNA is constructed where an engineered mature crRNA (conferring target specificity) is fused to a tracrRNA (supplying interaction with the Cas9) to create a chimeric cr-RNA-tracrRNA hybrid (also termed a single guide RNA). (see Jinek ibid and Cong, ibid).

Target Sites

As described in detail above, DNA domains can be engineered to bind to any sequence of choice. An engineered DNA-binding domain can have a novel binding specificity, compared to a naturally-occurring DNA-binding domain. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453,242 and 6,534,261, incorporated by reference herein in their entireties. Rational design of TAL-effector domains can also be performed. See, e.g., U.S. Pat. No. 8,586,526.

Exemplary selection methods applicable to DNA-binding domains, including phage display and two-hybrid systems, are disclosed in U.S. Pat. Nos. 8,586,526; 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in co-owned WO 02/077227.

Selection of target sites; nucleases and methods for design and construction of fusion proteins (and polynucleotides encoding same) are known to those of skill in the art and described in detail in U.S. Patent Application Publication Nos. 20050064474 and 20060188987, incorporated by reference in their entireties herein.

In addition, as disclosed in these and other references, DNA-binding domains (e.g., multi-fingered zinc finger proteins) may be linked together using any suitable linker sequences, including for example, linkers of 5 or more amino acids. See, e.g., U.S. Pat. Nos. 6,479,626; 6,903,185; and 7,153,949 for exemplary linker sequences 6 or more amino acids in length. The proteins described herein may include any combination of suitable linkers between the individual DNA-binding domains of the protein. See, also, U.S. Pat. No. 8,586,526.

As noted above, the DNA-binding domains of the nucleases may be targeted to any gene. In certain embodiments, the nuclease (DNA-binding domain component) is targeted to a "safe harbor" locus, which includes, by way of example only, the AAVS1, HPRT, albumin and CCR5 genes in human cells, and Rosa26 in murine cells (see, e.g., U.S. Pat. Nos. 7,888,121; 7,972,854; 7,914,796; 7,951,925; 8,110,379; 8,409,861; 8,586,526; U.S. Patent Publications 20030232410; 20050208489; 20050026157; 20060063231; 20080159996; 201000218264; 20120017290; 20110265198; 20130137104; 20130122591; 20130177983 and 20130177960) and the Zp15 locus in plants (see U.S. Pat. No. 8,329,986).

Donors

The present disclosure relates to nuclease-mediated targeted integration of an exogenous sequence into the genome of an HSC/PC in which the exogenous sequence is introduced using a lentiviral vector (e.g., IDLV). As noted above, insertion of an exogenous sequence (also called a "donor sequence" or "donor" or "transgene"), for example for correction of a mutant gene or for increased expression of a wild-type gene or for expression of a transgene. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

Described herein are methods of targeted insertion of any polynucleotides for insertion into a chosen location. Polynucleotides for insertion can also be referred to as "exogenous" polynucleotides, "donor" polynucleotides or molecules or "transgenes." The donor polynucleotide can be DNA or RNA, single-stranded and/or double-stranded and can be introduced into a cell in linear or circular form. See, e.g., U.S. Patent Publication Nos. 20100047805 and 20110207221. The donor sequence(s) are preferably contained within a DNA MC, which may be introduced into the cell in circular or linear form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by viruses (e.g., adenovirus, AAV, herpesvirus, retrovirus, lentivirus and integrase defective lentivirus (IDLV)).

In certain embodiments, the double-stranded donor includes sequences (e.g., coding sequences, also referred to as transgenes) greater than 1 kb in length, for example between 2 and 200 kb, between 2 and 10 kb (or any value therebetween). The double-stranded donor also includes at least one nuclease target site, for example. In certain embodiments, the donor includes at least 2 target sites, for example for a pair of ZFNs or TALENs. Typically, the nuclease target sites are outside the transgene sequences, for example, 5' and/or 3' to the transgene sequences, for cleavage of the transgene. The nuclease cleavage site(s) may be for any nuclease(s). In certain embodiments, the nuclease target site(s) contained in the double-stranded donor are for the same nuclease(s) used to cleave the endogenous target into which the cleaved donor is integrated via homology-independent methods.

The donor is generally inserted so that its expression is driven by the endogenous promoter at the integration site, namely the promoter that drives expression of the endogenous gene into which the donor is inserted (e.g., globin, AAVS1, etc.). However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. In other embodiments, the transgene (e.g., with or without globin encoding sequences) is integrated into any endogenous locus, for example a safe-harbor locus. See, e.g., US patent publications 20080299580; 20080159996 and 201000218264.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals. Additionally, splice acceptor sequences may be included. Exemplary splice acceptor site sequences are known to those of skill in the art and include, by way of example only, CTGACCTCTTCTCTTCCTCCCACAG, (SEQ ID NO:19) (from the human HBB gene) and TTTCTCTCCACAG (SEQ ID NO:20) (from the human Immunoglobulin-gamma gene).

The transgenes carried on the donor sequences described herein may be isolated from plasmids, cells or other sources using standard techniques known in the art such as PCR. Donors for use can include varying types of topology, including circular supercoiled, circular relaxed, linear and the like. Alternatively, they may be chemically synthesized using standard oligonucleotide synthesis techniques. In addition, donors may be methylated or lack methylation. Donors may be in the form of bacterial or yeast artificial chromosomes (BACs or YACs).

The double-stranded donor polynucleotides described herein may include one or more non-natural bases and/or backbones. In particular, insertion of a donor molecule with methylated cytosines may be carried out using the methods described herein to achieve a state of transcriptional quiescence in a region of interest.

The exogenous (donor) polynucleotide may comprise any sequence of interest (exogenous sequence). Exemplary exogenous sequences include, but are not limited to any polypeptide coding sequence (e.g., cDNAs), promoter sequences, enhancer sequences, epitope tags, marker genes, cleavage enzyme recognition sites and various types of expression constructs. Marker genes include, but are not limited to, sequences encoding proteins that mediate antibiotic resistance (e.g., ampicillin resistance, neomycin resistance, G418 resistance, puromycin resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

In a preferred embodiment, the exogenous sequence (transgene) comprises a polynucleotide encoding any polypeptide of which expression in the cell is desired, including, but not limited to antibodies, antigens, enzymes, receptors (cell surface or nuclear), hormones, lymphokines, cytokines, reporter polypeptides, growth factors, and functional fragments of any of the above. The coding sequences may be, for example, cDNAs.

For example, the exogenous sequence may comprise a sequence encoding a polypeptide that is lacking or non-functional in the subject having a genetic disease, including but not limited to any of the following genetic diseases: achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasiaossificans progressive, fragile X syndrome, galactosemis, Gaucher's disease, generalized gangliosidoses (e.g., GM1), hemochromatosis, the hemoglobin C mutation in the 6$^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipdius, neurofibromatosis, Neimann-Pick disease, osteogenesis *imperfecta, porphyria*, Prader-Willi syndrome, progeria, *Proteus* syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted integration include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

In certain embodiments, the exogenous sequences can comprise a marker gene (described above), allowing selection of cells that have undergone targeted integration, and a linked sequence encoding an additional functionality. Non-limiting examples of marker genes include GFP, drug selection marker(s) and the like.

Additional gene sequences that can be inserted may include, for example, wild-type genes to replace mutated sequences. For example, a wild-type Factor IX gene sequence may be inserted into the genome of a stem cell in which the endogenous copy of the gene is mutated. The wild-type copy may be inserted at the endogenous locus, or may alternatively be targeted to a safe harbor locus.

Construction of such expression cassettes, following the teachings of the present specification, utilizes methodologies well known in the art of molecular biology (see, for example, Ausubel or Maniatis). Before use of the expression cassette to generate a transgenic animal, the responsiveness of the expression cassette to the stress-inducer associated with selected control elements can be tested by introducing the expression cassette into a suitable cell line (e.g., primary cells, transformed cells, or immortalized cell lines).

Furthermore, although not required for expression, exogenous sequences may also transcriptional or translational regulatory sequences, for example, promoters, enhancers, insulators, internal ribosome entry sites, sequences encoding 2A peptides and/or polyadenylation signals. Further, the control elements of the genes of interest can be operably linked to reporter genes to create chimeric genes (e.g., reporter expression cassettes).

Targeted insertion of non-coding nucleic acid sequence may also be achieved. Sequences encoding antisense RNAs, RNAi, shRNAs and micro RNAs (miRNAs) may also be used for targeted insertions.

In additional embodiments, the donor nucleic acid may comprise non-coding sequences that are specific target sites for additional nuclease designs. Subsequently, additional nucleases may be expressed in cells such that the original donor molecule is cleaved and modified by insertion of another donor molecule of interest. In this way, reiterative integrations of donor molecules may be generated allowing for trait stacking at a particular locus of interest or at a safe harbor locus.

Delivery

The nucleases, polynucleotides encoding these nucleases, donor polynucleotides and compositions comprising the proteins and/or polynucleotides described herein may be delivered in vivo or ex vivo by any suitable means into any cell type.

Suitable cells include eukaryotic (e.g., animal) and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOK1SV), VERO, MDCK, WI38, V79, B14AF28-G3, BHK, HaK, NS0, SP2/0-Ag14, HeLa, HEK293 (e.g., HEK293-F, HEK293-H, HEK293-T), and perC6 cells as well as insect cells such as Spodoptera-fugiperda (Sf), or fungal cells such as *Saccharomyces, Pichia* and *Schizosaccharomyces*. In certain embodiments, the cell line is a CHO, MDCK or HEK293 cell line. Suitable cells also include stem cells such as, by way of example, embryonic stem cells, induced pluripotent stem cells, hematopoietic stem cells, neuronal stem cells and mesenchymal stem cells.

Methods of delivering nucleases as described herein are described, for example, in U.S. Pat. Nos. 6,453,242; 6,503,717; 6,534,261; 6,599,692; 6,607,882; 6,689,558; 6,824, 978; 6,933,113; 6,979,539; 7,013,219; and 7,163,824, the disclosures of all of which are incorporated by reference herein in their entireties.

Nucleases and/or donor constructs as described herein may also be delivered using vectors containing sequences encoding one or more of the ZFN(s), TALEN(s) or CRIPSR/Cas systems. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties. Furthermore, it will be apparent that any of these vectors may comprise one or more of the sequences needed for treatment. Thus, when one or more nucleases and a donor construct are introduced into the cell, the nucleases and/or donor polynucleotide may be carried on the same vector or on different vectors (DNA MC(s)). When multiple vectors are used, each vector may comprise a sequence encoding one or multiple nucleases and/or donor constructs.

Conventional viral and non-viral based gene transfer methods can be used to introduce nucleic acids encoding nucleases and donor constructs in cells (e.g., mammalian cells) and target tissues. Non-viral vector delivery systems include DNA or RNA plasmids, DNA MCs, naked nucleic acid, and nucleic acid complexed with a delivery vehicle such as a liposome, nanoparticle or poloxamer. Viral vector delivery systems include DNA and RNA viruses, which have either episomal or integrated genomes after delivery to the cell. For a review of in vivo delivery of engineered DNA-binding proteins and fusion proteins comprising these binding proteins, see, e.g., Rebar (2004) *Expert Opinion Invest. Drugs* 13(7):829-839; Rossi et al. (2007) *Nature Biotech.* 25(12):1444-1454 as well as general gene delivery references such as Anderson, *Science* 256:808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Böhm (eds.) (1995); and Yu et al., *Gene Therapy* 1:13-26 (1994).

Methods of non-viral delivery of nucleic acids include electroporation, lipofection, microinjection, biolistics, virosomes, liposomes, immunoliposomes, nanoparticles, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424, WO 91/16024.

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate* Chem. 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et at (2009) *Nature Biotechnology* 27(7):643).

The use of RNA or DNA viral based systems for the delivery of nucleic acids encoding engineered ZFPs, TALEs and/or CRISPR/Cas systems take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFPs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin et al., *Mol. Cell. Biol.* 4:2072-2081 (1984); Hermonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138 (1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a promising alternative gene delivery systems based on the defective and nonpathogenic parvovirus adeno-associated type 2 virus. All vectors are derived from a plasmid that retains only the AAV 145 by inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)). Other AAV serotypes, including AAV1, AAV2, AAV3, AAV4, AAV5, AAV6, AAV7, AAV8, AAV9 and AAVrh.10 and any novel AAV serotype can also be used in accordance with the present invention.

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

Packaging cells are used to form virus particles that are capable of infecting a host cell. Such cells include 293 cells, which package adenovirus, and Ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Vectors (e.g., retroviruses, adenoviruses, liposomes, etc.) containing nucleases and/or donor constructs can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of polynucleotides (e.g. nuclease-encoding and/or double-stranded donors) described herein include non-integrating lentivirus vectors (IDLY). See, for example, Ory et al. (1996) *Proc. Natl. Acad. Sci. USA* 93:11382-11388; Dull et al. (1998) *J. Virol.*72:8463-8471; Zuffery et al. (1998) *J. Virol.*72:9873-9880; Follenzi et al. (2000) *Nature Genetics* 25:217-222; U.S. Patent Publication No 2009/054985.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences*, 17th ed., 1989).

It will be apparent that the nuclease-encoding sequences and donor constructs can be delivered using the same or different systems. For example, the nucleases and donors can be carried by the same DNA MC. Alternatively, a donor polynucleotide can be carried by a MC, while the one or more nucleases can be carried by a standard plasmid or AAV vector. Furthermore, the different vectors can be administered by the same or different routes (intramuscular injection, tail vein injection, other intravenous injection, intraperitoneal administration and/or intramuscular injection. The vectors can be delivered simultaneously or in any sequential order.

Thus, the instant disclosure includes in vivo or ex vivo treatment of diseases and conditions that are amenable to insertion of a transgenes encoding a therapeutic protein, for example treatment of hemophilias via nuclease-mediated integration of clotting factors such as Factor VIII (F8). The compositions are administered to a human patient in an amount effective to obtain the desired concentration of the therapeutic polypeptide in the serum or the target organ or cells. Administration can be by any means in which the polynucleotides are delivered to the desired target cells. For example, both in vivo and ex vivo methods are contemplated. Intravenous injection to the portal vein is a preferred method of administration. Other in vivo administration modes include, for example, direct injection into the lobes of the liver or the biliary duct and intravenous injection distal to the liver, including through the hepatic artery, direct injection in to the liver parenchyma, injection via the hepatic artery, and/or retrograde injection through the biliary tree. Ex vivo modes of administration include transduction in vitro of resected hepatocytes or other cells of the liver, followed by infusion of the transduced, resected hepatocytes back into the portal vasculature, liver parenchyma or biliary tree of the human patient, see e.g., Grossman et al., (1994) *Nature Genetics,* 6:335-341.

The effective amount of nuclease(s) and donor to be administered will vary from patient to patient and according to the therapeutic polypeptide of interest. Accordingly, effective amounts are best determined by the physician administering the compositions and appropriate dosages can be determined readily by one of ordinary skill in the art. After allowing sufficient time for integration and expression (typically 4-15 days, for example), analysis of the serum or other tissue levels of the therapeutic polypeptide and comparison to the initial level prior to administration will determine whether the amount being administered is too low, within the right range or too high. Suitable regimes for initial and subsequent administrations are also variable, but are typified by an initial administration followed by subsequent administrations if necessary. Subsequent administrations may be administered at variable intervals, ranging from daily to annually to every several years. One of skill in the art will appreciate that appropriate immunosuppressive techniques may be recommended to avoid inhibition or blockage of transduction by immunosuppression of the delivery vectors, see e.g., Vilquin et al., (1995) *Human Gene Ther.,* 6:1391-1401.

Formulations for both ex vivo and in vivo administrations include suspensions in liquid or emulsified liquids. The active ingredients often are mixed with excipients which are pharmaceutically acceptable and compatible with the active ingredient. Suitable excipients include, for example, water, saline, dextrose, glycerol, ethanol or the like, and combinations thereof. In addition, the composition may contain minor amounts of auxiliary substances, such as, wetting or emulsifying agents, pH buffering agents, stabilizing agents or other reagents that enhance the effectiveness of the pharmaceutical composition.

The following Examples relate to exemplary embodiments of the present disclosure in which the nuclease comprises a zinc finger nuclease (ZFN). It will be appreciated that this is for purposes of exemplification only and that other nucleases can be used, for instance TALENs, CRISPR/Cas systems, homing endonucleases (meganucleases) with engineered DNA-binding domains and/or fusions of naturally occurring of engineered homing endonucleases (meganucleases) DNA-binding domains and heterologous cleavage domains.

EXAMPLES

Example 1

Methods

Homology-directed repair donor templates were generated from HIV-derived, third-generation self-inactivating transfer constructs. IDLV stocks were prepared as previously described (Lombardo, A. et al. (2007) *Nat Biotechnol* 25, 1298-1306) and titered by a qPCR designed to discriminate the reverse transcribed vector genome from plasmid carried over from transient transfection. Sequence and maps of AAVS1-PGK.GFP were previously reported (Lombardo, A. et al. (2011) *Nature Methods* 8, 861-869). ZFNs that target intron 1 of PPP1R12C or exon 5 of IL2RG were previously described (Lombardo, A. et al. (2007) ibid) and were designed and assembled using an established archive of pre-validated 2-finger and 1-finger modules essentially as described in U.S. Patent Publication No. 20120060230.

Both pairs of ZFNs were transiently expressed as mRNAs. Plasmid templates for ZFNs mRNA production were linearized and purified by phenol/chloroform extraction followed by ethanol DNA precipitation. 2 μg/reaction of linearized plasmid template was in vitro transcribed at 37° C. for 2 hr using T7 RNA polymerase and 7.5 mM nucleotide triphosphates (MEGAscript Kit; Ambion). CapO mRNAs was generated by supplementing the reactions with 6 mMm7(3'-O-methyl)-G(5)ppp(5')G, a nonreversible cap analog (ARCA, New England Biolabs) and lowering the concentration of GTP to 1.5 mM. After TURBO DNase treatment (4 U/reaction, 1 hr at 37° C.), mRNAs were poly(A) tailed with E. *Coli* Poly(A) Polymerase (8 U/reaction) for 1 hr at 37° C. (PolyA tailing kit; Ambion), yielding ≥150 ntpolyA. Transcripts were purified by RNeasyPlus Mini Kit (Qiagen). All RNA samples were analyzed by denaturing agarose gel electrophoresis for quality assurance.

In Vitro Culture and Assays on CB-derived CD34+ Cells

CD34+ cells were either freshly purified from human cord blood after obtaining informed consent and upon approval by the San Raffaele Hospital Bioethical Committee, or purchased frozen from Lonza. $10^6$ CD34+ cells/ml were stimulated in serum-free StemSpan medium (StemCell Technologies) supplemented with penicillin, streptomycin and human early-acting cytokines (stem cell factor (SCF) 100 ng/ml, Flt3 ligand (Flt3-L) 100 ng/ml, thrombopoietin (TPO) 20 ng/ml, and interleukin 6 (IL-6) 20 ng/ml; all purchased from Peprotech) for 24 or 48 hr and then infected with IDLVs at multiplicity of infection (MOI) 100-500. The following day the cells were electroporated with 175 μg/ml ZFNs encoding mRNAs (P3 Primary *Cell* 4D-Nucleofector X Kit, program EO 100; Lonza). For some experiments, the following drugs were supplemented to the culture media: 1 μM SR1 (Novartis) added at every medium change, and 10 μM PGE2 (Cayman) added at the beginning of the culture, 1 hour before and just after electroporation. For CFC assays, 800 cells were plated one day after electroporation in methylcellulose-based medium (MethoCult H4434, Stem-Cell Technologies). Two weeks after plating, colonies were counted and identified according to morphological criteria.

Flow Cytometry

For immunophenotypic analysis of CD34+ cells and their progeny (performed on FACSCanto™ II; BD Pharmingen), standard anti-CD34+ antibodies were used (PECy7-conjugated anti-human CD34 (BD Pharmingen). Single stained and FMO stained cells were used as controls. For quantitative flow cytometry Flow-count Fluorospheres (Beckman Coulter) were used according to the manufacturers' instructions. Apoptosis analysis was performed on CD34+ cells one day after electroporation using PB-conjugated Annexin V (Biolegend) and Apoptosis Detection Kit with 7AAD (BD Pharmingen) according to the manufacturers' instructions. Percentages of live (7AAD−, Annexin V−), early apoptotic (7AAD−, Annexin V+), late apoptotic (7AAD+, Anexin V+) and necrotic (7AAD+, Annexin V−) cells are reported. Sorting was performed using MoFlo™ XDP Cell Sorter (Beckman Coulter).

Molecular Analyses

For molecular analyses, genomic DNA was isolated with DNeasy Blood & Tissue Kit or QIAamp® DNA Micro Kit (QIAGEN). Extraction of genomic DNA from colonies in CFC assays was performed with Lysis Buffer. NHEJ in AAVS1 locus or IL2RG gene was detected by the mismatch selective Cell assay as previously described (Lombardo 2007 ibid). Primers for PCR amplifications to detect targeted integration or for the Cell assay are indicated in Table 1. PCR amplicons were resolved on agarose gel and visualized by ethydium bromide staining. For Southern Blot analyses, genomic DNA was extracted with Blood & Cell Culture DNA Midi Kit (QIAGEN) and digested with BglI for AAVS1 locus and BspHI for IL2RG. Matched DNA amounts were separated on 1% agarose, transferred to a nylon membrane and probed with $^{32}$P-radiolabeled sequences according to standard protocols. Membranes were exposed in a Storage Phosphor Screen. For qPCR analysis, 200 ng of genomic DNA were analyzed using primers and probes complementary to a vector backbone sequence (Primer Binding Site), the GFP sequence and human TERT, the latter amplification used as normalizer, as previously described (Lombardo 2007, ibid).

For gene expression analysis on the SCID-X1 gene corrected colony, mRNA was extracted using the RNeasy® Micro Kit (QIAGEN) and cDNA was synthesized using the SuperScript® VILO cDNA Synthesis Kit (Invitrogen). The resulting cDNA was amplified before qPCR by Taqman® PreAmp Master Mix Kit (Invitrogen) according to manufacturer's instructions. Gene expression was performed in triplicate with a TaqMan® Expression assay specific for the recoded exon 7 of the IL2RG gene (Applied Biosystems) in a 7900HT real-time PCR thermal cycler. The relative expression level of the recoded IL2RG gene was calculated by the ΔΔCt method and represented as fold change relative to the housekeeping gene control (HPRT) as described (Lombardo (2011) ibid).

TABLE 1

Primers used

| | | |
|---|---|---|
| **Targeted integration into AAVS1 by HDR** | | |
| 5' integration junction | | |
| Forward AAVS1 primer | 5'-AACTCTGCCCTCTAACGCTGC-3' | SEQ ID NO: 1 |
| Reverse hPGK primer | 5'-ACGTGAAGAATGTGCGAGACCCAG-3' | SEQ ID NO: 2 |
| 3'integration junction | | |
| Forward BGHpA primer | 5'-TTGCATCGCATTGTCTGAGTAGG-3' | SEQ ID NO: 3 |
| Reverse AAVS1 primer | 5'-AACGGGGATGCAGGGGAACG-3' | SEQ ID NO: 4 |
| **Targeted integration into IL2RG by HDR** | | |
| 5'integration junction | | |
| Forward IL2RGprimer | 5'-GCTAAGGCCAAGAAAGTAGGGCTAAAG-3' | SEQ ID NO: 5 |
| Reverse IL2RG cDNA exon 6 recoded primer | 5'-AGCCAGAAGTACACGCACAGC-3' | SEQ ID NO: 6 |
| 3' integration junction | | |
| Forward SV40pA primer | 5'-ACCTCTACAAATGTGGTATGGCTG-3' | SEQ ID NO: 7 |
| Reverse IL2RGprimer | 5'-TTCCTTCCATCACCAAACCCTCTTG-3' | SEQ ID NO: 8 |
| **Targeted integration into IL2RG by NHEJ (sense orientation)** | | |
| 5' integration junction | | |
| Forward IL2RGprimer | 5'-GCTAAGGCCAAGAAAGTAGGGCTAAAG-3' | SEQ ID NO: 5 |
| Reverse dNEFprimer | 5'-CGAGCTCGGTACCTTTAAGACC-3' | SEQ ID NO: 9 |
| 3'integration junction | | |
| Forward 5NC2 primer | 5'-GAGTCCTGCGTCGAGAGAG-3' | SEQ ID NO: 10 |
| Reverse IL2RGprimer | 5'-TTCCTTCCATCACCAAACCCTCTTG-3' | SEQ ID NO: 8 |

TABLE 1-continued

| Primers used | | |
|---|---|---|
| **Targeted integration into IL2RG by NHEJ (antisense orientation)** | | |
| 5' integration junction | | |
| Forward IL2RGprimer | 5'-GCTAAGGCCAAGAAAGTAGGGCTAAAG-3' | SEQ ID NO: 5 |
| Reverse 5NC2 primer | 5'-GAGTCCTGCGTCGAGAGAG-3 ' | SEQ ID NO: 10 |
| 3'integration junction | | |
| Forward dNEFprimer | 5'-CGAGCTCGGTACCTTTAAGACC-3' | SEQ ID NO: 9 |
| Reverse IL2RGprimer | 5'-TTCCTTCCATCACCAAACCCTCTTG-3' | SEQ ID NO: 8 |
| **Mismatch selective endonuclease assay (AAVS1)** | | |
| Forward Cel1-AAVS1 primer | 5'-CTTCAGGACAGCATGTTTGC-3' | SEQ ID NO: 11 |
| Reverse Cel1-AAVS1 primer | 5'-ACAGGAGGTGGGGGTTAGAC-3' | SEQ ID NO: 12 |
| **Mismatch selective endonuclease assay (IL2RG)** | | |
| Forward Cel1-IL2RG primer | 5'-TTCTCCCTTCTCTCATAGACACCC-3' | SEQ ID NO: 13 |
| Reverse Cel1-IL2RG primer | 5'-CTCATGGATTGGGTCATGTGG-3' | SEQ ID NO: 14 |
| **Southern blot analysis to detect targeted integration in AAVS1** | | |
| Forward AAVS1 probe primer | 5'-TCCTCCTTCCCCGTTGCCAGTCTC-3' | SEQ ID NO: 15 |
| Reverse AAVS1 probe primer | 5'-GCAGCGTTAGAGGGCAGAGTTC-3' | SEQ ID NO: 16 |
| **Southern blot analysis to detect targeted integration in IL2RG** | | |
| Forward IL2RG probe primer | 5'-AGGGATACTGTGGGACATTGGAG-3' | SEQ ID NO: 17 |
| Reverse IL2RG probe primer | 5'-AGGTCCTTCTATCTGTCTGGTTG-3' | SEQ ID NO: 18 |

Mice Transplantation and Analysis

For the in vivo studies, 8- to 11-week-old NOD-SCID-IL2Rg$^{-/-}$ (NSG) mice were purchased from the Jackson laboratory. The experimental protocol was approved by the Institutional Animal Care and Use Committee of the San Raffaele Scientific Institute. At day 4 of culture, $3\times10^5$ gene targeted CD34+ cells (or $7.5\times10^5$ BM derived cells) were infused intravenously into the mice after sub-lethal irradiation (200 cGy).MDA3 human mammary carcinoma cell line was obtained by stable transduction of MDA-MB 231 cells with lentiviral vectors expressing the human cytokines GMCSF, IL-7 and IL-15 from the PGK promoter. $4\times10^6$MDA3 cells were implanted orthotopically in the mammary fat pad of NSG mice 14 weeks after CD34+ cells transplantation or in age-matched untransplanted NSG mice. Human CD45+ engraftment was followed by serial collections of blood from the mouse tail and, at the end of the experiment (12-23 weeks after transplantation), BM, spleen and *thymus* cells were harvested and analyzed. HumanT lymphocytes were enriched from mouse splenocytes using magnetic beads conjugated to anti human CD3 and CD28 antibodies (Dynabeads human T-activator CD3/CD28; Invitrogen), following the manufacturer instructions, and grown in Iscove's Modified Dulbecco's Media (IMDM) (GIBCO-BRL) supplemented with penicillin, streptomycin, 10% FBS and 5 ng/ml each of IL-7 and IL-15 (PeproTech).

T Lymphocyte Analysis

Human T lymphocytes were enriched from mouse splenocytes using magnetic beads conjugated to anti human CD3 and CD28 antibodies (Dynabeads human T-activator CD3/CD28; Invitrogen), following the manufacturers' instructions, and grown in Iscove's Modified Dulbecco's Media (IMDM) (GIBCO-BRL) supplemented with penicillin, streptomycin, 10% FBS and 5 ng/ml each of IL-7 and IL-15 (PeproTech).

For TCR V-β repertoire analysis, mRNA was extracted from the expanded T cells using RNeasy Mini Kit (QIAGEN) and cDNA was synthetized using SuperScript VILO cDNA Synthesis Kit (Invitrogen). Multiplex PCR optimized from a previous work (Akatsuka et at (1999) *Tissue Antigens* 53:122-134) were carried out on cDNA using V-β primers specific for 4 or 5 different families and a single FAM-labeled C-β primer. PCR products were fractionated on 6% polyacrylamide gel, visualized on Molecular Dynamics Typhoon 9410 (Amersham Biosciences) and analyzed using ImageQuant® TL 7.0 (Amersham Biosciences). The V-β complexity was determined by counting the number of distinct peaks and graded on a score of 0-8 (Wu et at (2000) *Blood* 95:352-359). The overall TCR complexity score was determined by summing up all 23 individual TCR V-β family specific scores.

For IL2RG phosphorylation analysis, T cells were starved overnight at 37° C. in IMDM without cytokines and then stimulated with IL-2 (1000 IU/ml, 100 IU/ml, 10 IU/ml) or IL-15 (10 ng/ml, 5 ng/ml, 1 ng/ml) at 37° C. for increasing times. Cells were then fixed in PBS 2% paraformaldehyde (PFA) for 10' at 37° C., and after washing in PBS 0.1% BSA (3 times), they were permeabilized with ice-cold absolute methanol for 7' on ice. After 60' incubation of each time point of cytokine stimulation with different dilutions of Pacific Blue Succinimidyl Ester (PBSE) (Life Technologies), cells were washed, pooled and stained for flow cytometry.

For proliferation assay, $10^5$ T cells were labeled with Cell Proliferation Dye eFluor 670 (eBioscience) according to the manufacturer's instructions. Labeled T cells were co-cultured in IMDM supplemented with penicillin, streptomycin, 10% FBS with 5 ng/ml each of IL-7 and IL-15, with different dilutions of MDA-MB 231 cells that had previously been irradiated at 10000 rad or stimulated for 3 days with PHA (2 μg/ml).

After 7 days of culture, cells were analyzed by flow cytometry. Division index was calculated using FlowJo® software.

For IFN-γ release assay, T cells were stimulated at 37° C. for 6 hours with PMA (50 ng/ml) and Ionomycin (1 μg/ml) in presence of 2 μl per ml of culture of BD Golgi Plug (BD Pharmingen). Cells were then fixed and permeabilized using BD Cytofix/Cytoperm Kit (BD Pharmingen) and stained for flow cytometry.

Statistical Analyses

Statistical analyses were performed by unpaired Student's t test for pairwise comparison or one way analysis of variance (ANOVA) with Bonferroni's multiple comparison post-test for three or more groups, as indicated. Values are expressed as Mean±standard error of the mean (SEM). Percent values were transformed into a log-odds scale (log (% x/(100−% x)) to perform statistical analyses.

Deep Sequencing of Potential IL2RG ZFN Off-target Loci

Genomic DNA from ZFN-treated CD34+ cells or their progeny harvested from transplanted mice was amplified using REPLI-g Mini Kit (QIAGEN) and the top ranking candidate off-target genomic loci from our previous study (Gabriel et al., (2011) *Nat Biotechnol* 29: 816-823) were amplified by PCR generating amplicons of 389±20 by surrounding the potential ZFN binding site. PCR products were purified using Agencourt AMPure® XP beads (Beckman Coulter, Brea, Calif.) and adaptors were added by TruSeq® DNA LT Sample Prep Kit (Illumina, San Diego, Calif.). In order to build an equimolar library, PCR products were quantified with KAPA Library Quantification Kit for Illumina sequencing platforms (KAPABIOSYSTEMS, Wilmington, Mass.) on C1000 Thermal Cycler (BIO-RAD, Hercules, Calif.) and sequenced on MiSeq Illumina Platform using MiSeq Reagent v.3 (Illumina). Raw paired-end reads were joined with Fastq-Join program from the EA-Utils NGS suite (Google Project Hosting) and aligned to the specific genomic target sequences using Burrows-Wheeler Alignment Tool with maximal exact match version, BWA-MEM (Li and Durbin (2009) *Bioinformatics.* 25(14):1754-60).

Alignments were evaluated and filtered using SAMtools (Li et al., (2009) *Bioinformatics,* 25, 2078-9), Picard and BAMtools (Barnett et at (2011) *Bioinformatics* 27 (12): 1691-1692). Sequences with only primary alignments with quality >15 were kept for further analysis. Deletions and insertions (indels) were quantified by a custom pipeline based on Python and the PySAM library. Sequences with indels of ≥1 by located within a region encompassing the spacer+5 by on each side were considered as ZFN-induced genome modifications. Coverage statistics were computed by the binomial distribution online calculator. Fisher exact test were computed with the SciPy Python package within the "stats" library. Multiple sequence alignment for indels visualization and plot was performed with ClustalW2 (Larkin et al., (2007) *Bioinformatics.* 23(21):2947-8) and MView (Brown et at (1998) *Bioinformatics.* 14(4):380-1).

Example 2

Efficient Gene Targeting in Human CD34+ Cells

Figure 1B:
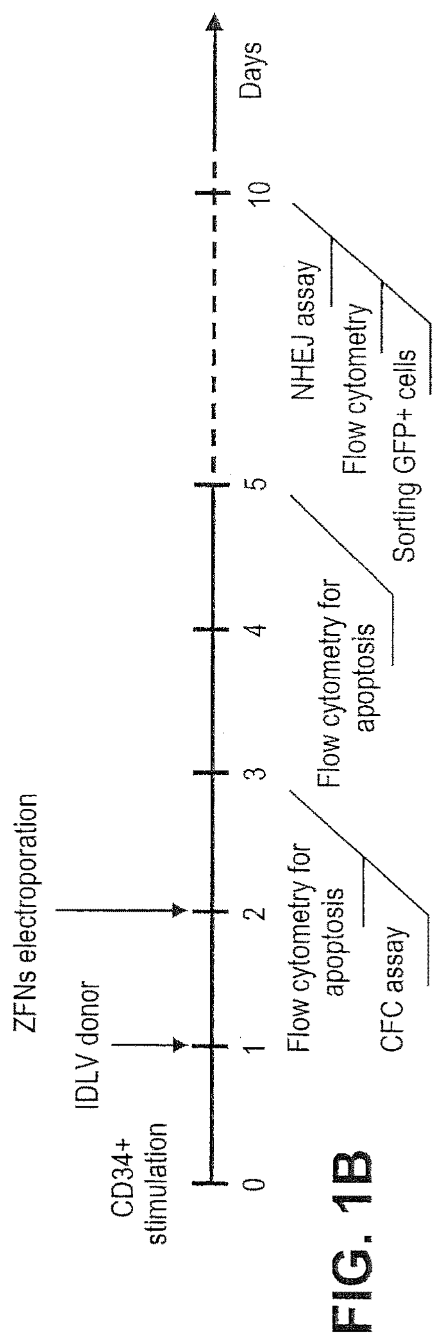
Figure 5A:
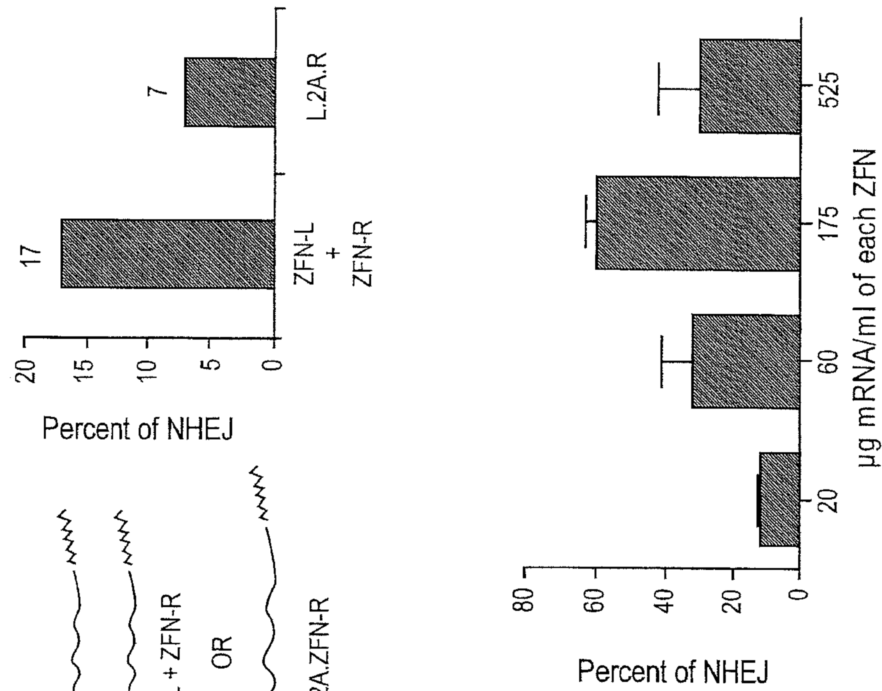
FIGS. 5A through 5D depict optimizing combined delivery of ZFNs and donor template DNA.
Figure 5A:
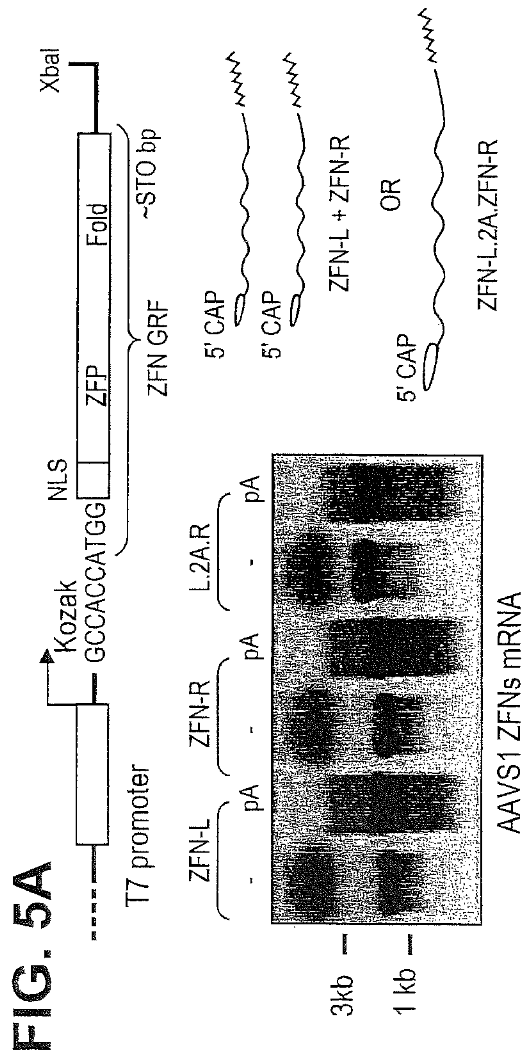
Figure 5B:
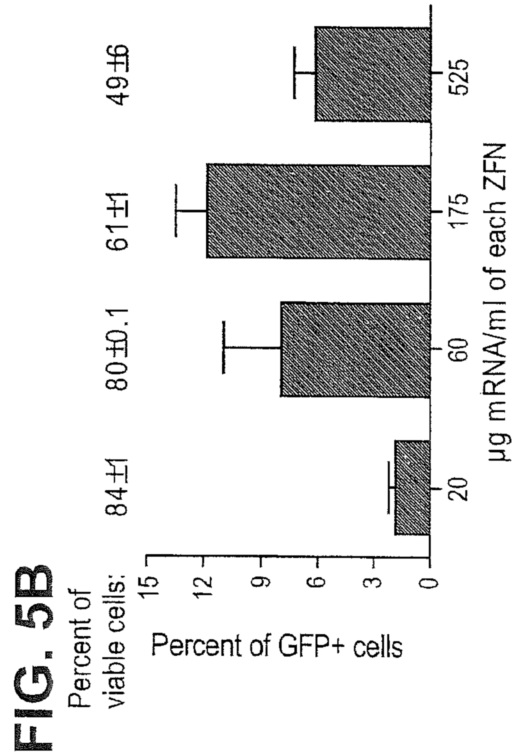
Figure 5C:
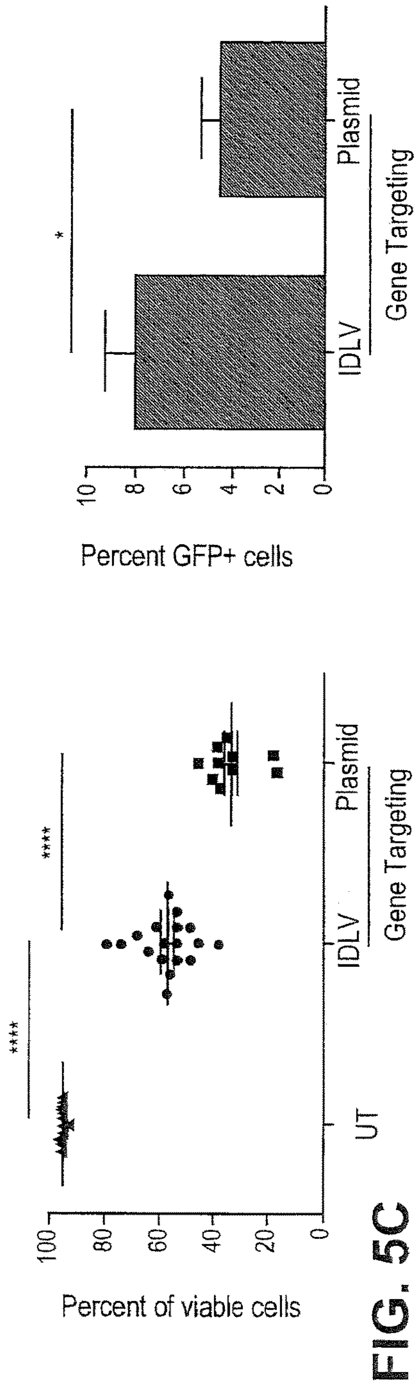
Figure 5D:
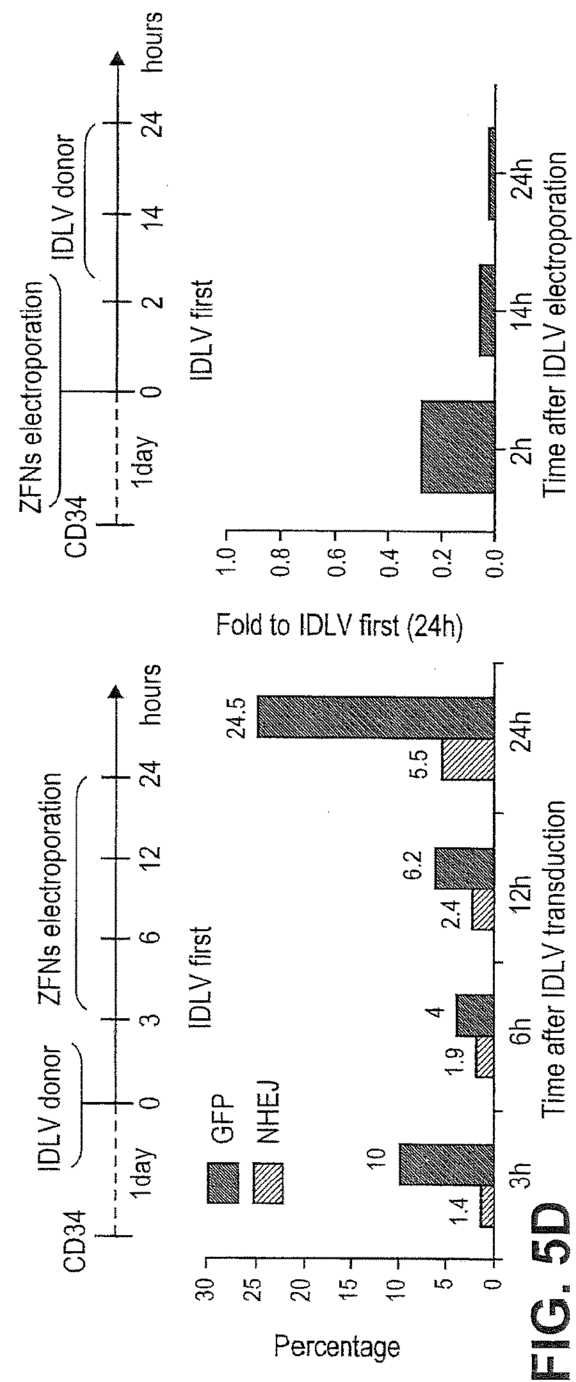

A protocol for targeted integration of a GFP expression cassette into genomic loci (FIG. 1A) of human CD34+ cells was developed by optimizing the delivery platform, dose and timing of ZFN and donor template administration. ZFN activity was scored by measuring the extent of NHEJ-mediated repair at their genomic target site, and HDR by measuring the frequency of GFP+ cells obtained in liquid culture. For ZFN expression, mRNA electroporation outperformed all approaches tested in terms of the frequency of transfected cells and protein expression level (FIG. 1L); mRNA dose and design were then optimized for expressing paired ZFN (FIG. 5). For donor template delivery, Integrase Defective Lentiviral Vector (IDLV, see Lombardo, 2007, ibid) infection outperformed plasmid DNA electroporation in terms of the frequency of GFP+ cells and cell viability (FIG. 5C). Finally, the highest frequency of GFP+ cells was obtained by combining IDLV-based donor template delivery 24 hours before ZFNs mRNA electroporation (FIG. 5D and FIG. 1B).

Figure 1C:
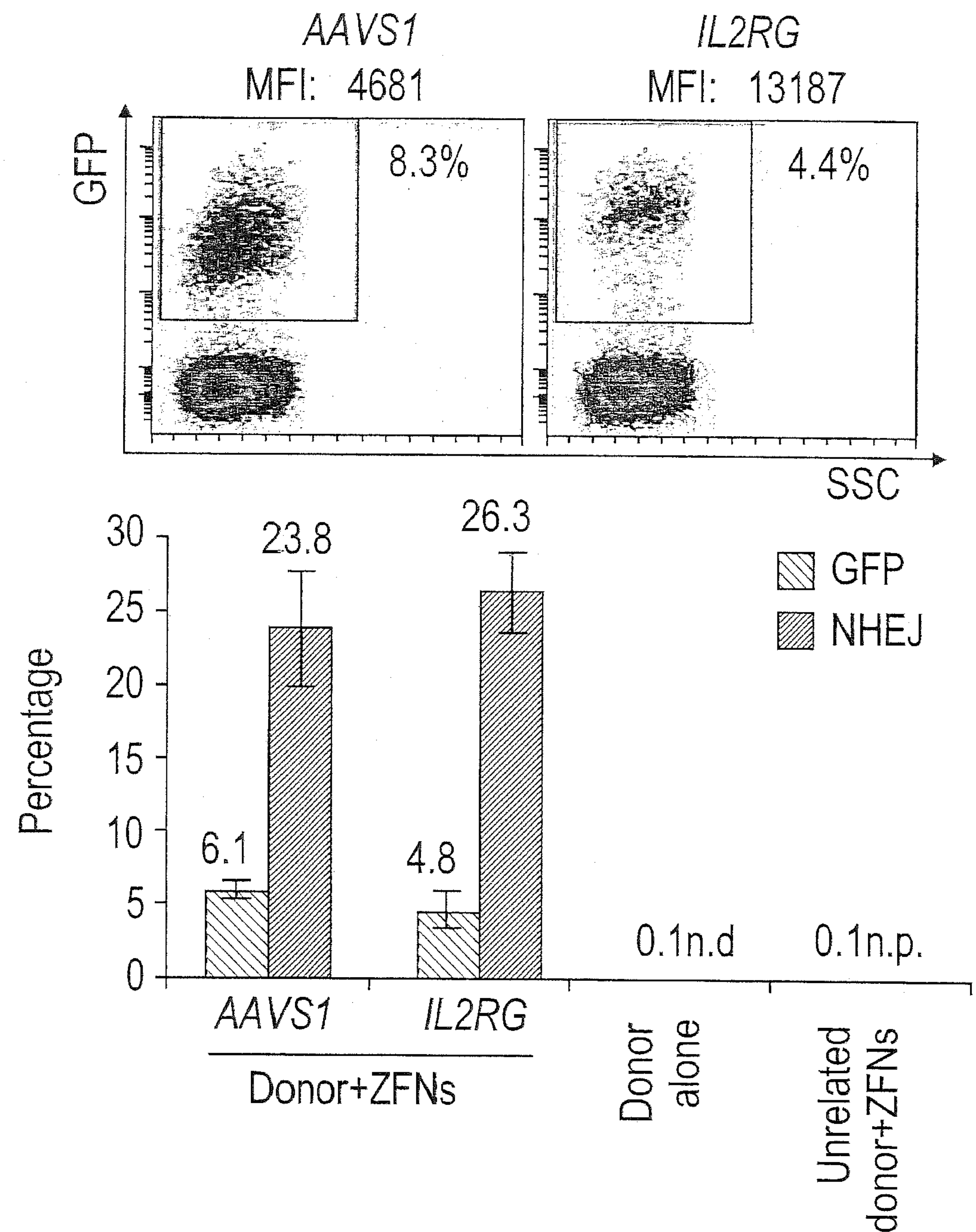

This optimized protocol reproducibly yielded high percentages of GFP-expressing progenies of CD34+ cells treated with ZFNs and cognate donor targeting the AAVS1 "safe harbor" site or a mutational hotspot within exon 5 of the IL2RG gene (6.1±0.59 or 4.8±1.2 mean±SEM GFP-positive cells, respectively; n=28 different CB donors; FIG. 1C). Accordingly, we measured high percentages of insertions and/or deletions ("indels") introduced by NHEJ into the respective ZFN target sites (23.8±3.8 or 26.3±2.7 for AAVS1 or IL2RG, respectively FIG. 1C).

Figure 1D:
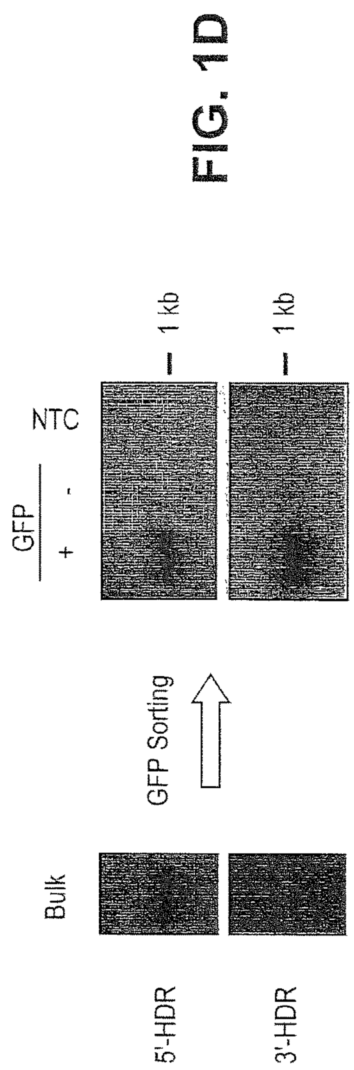
Figure 1E:
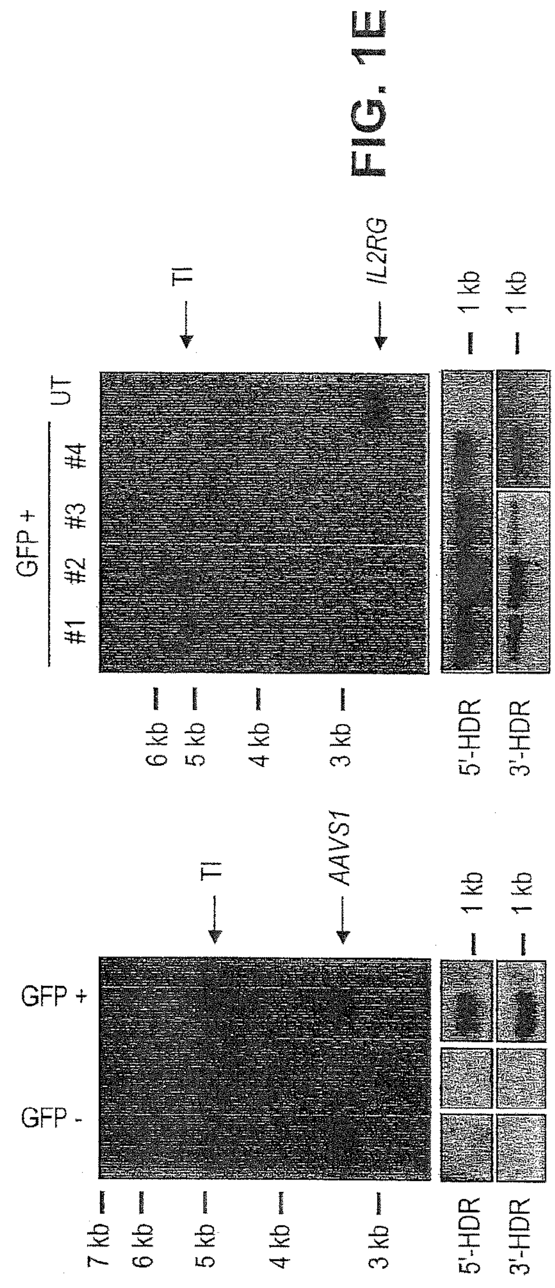

Integration of the GFP-expression cassette at the intended target sites was demonstrated by PCR analyses performed both on bulk treated and GFP+ sorted cells (FIG. 1D). Moreover, Bona Fide Gene Targeting was Shown by Southern Blot on Genomic DNA from induced Pluripotent Stem Cell (iPSC) clones obtained by reprogramming the GFP+ sorted cells and expanding them in culture (FIG. 1E).

Figure 1F:
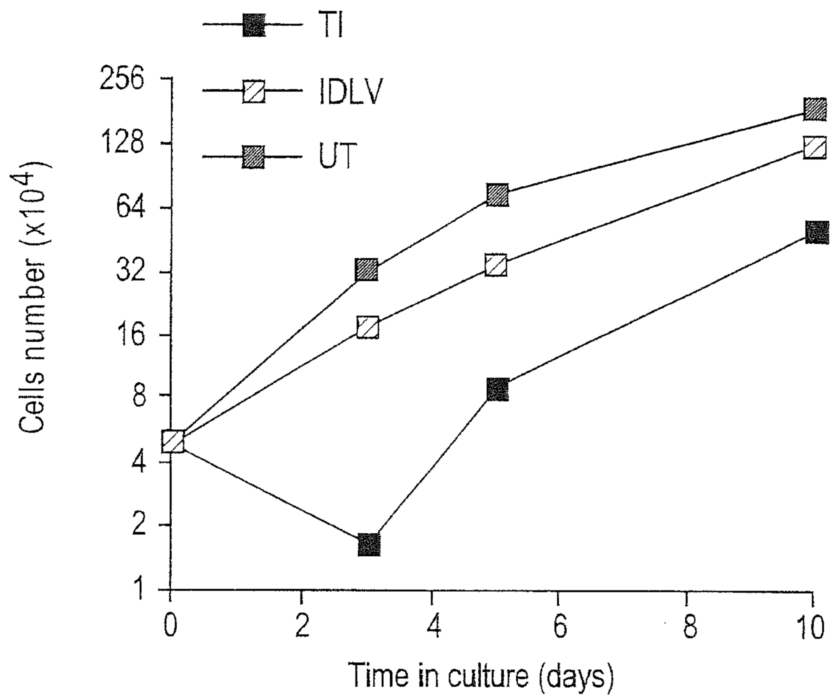
Figure 1G:
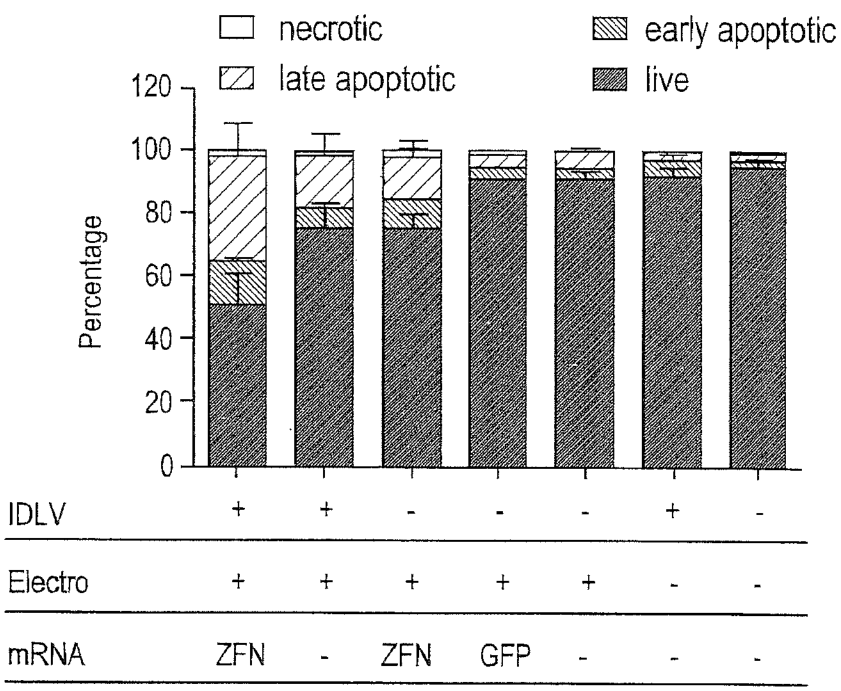

In parallel, we assessed the impact of the gene targeting procedure on the viability, proliferation and clonogenic capacity of the CD34+ cells. Twenty-four hours after electroporation there was a transient reduction in viable cell number, which resulted from the combined addition of the electroporation procedure, ZFN mRNA and IDLV transduction (FIGS. 1F and 1G). However, the surviving cells grew with similar kinetic as the untreated controls.

Figure 1H:
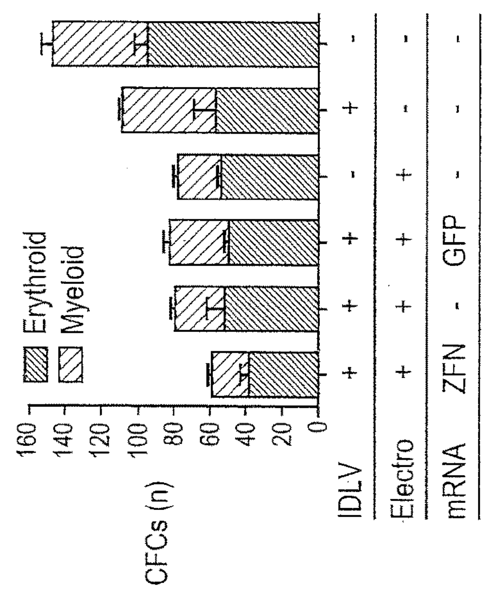
Figure 1I:
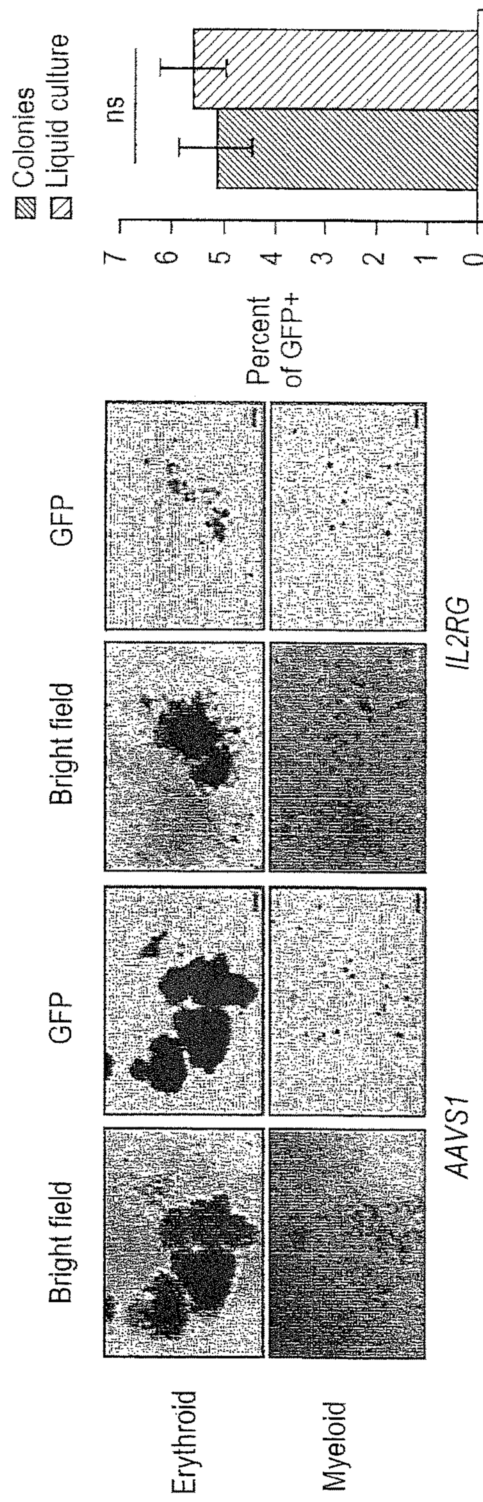
Figure 1J:
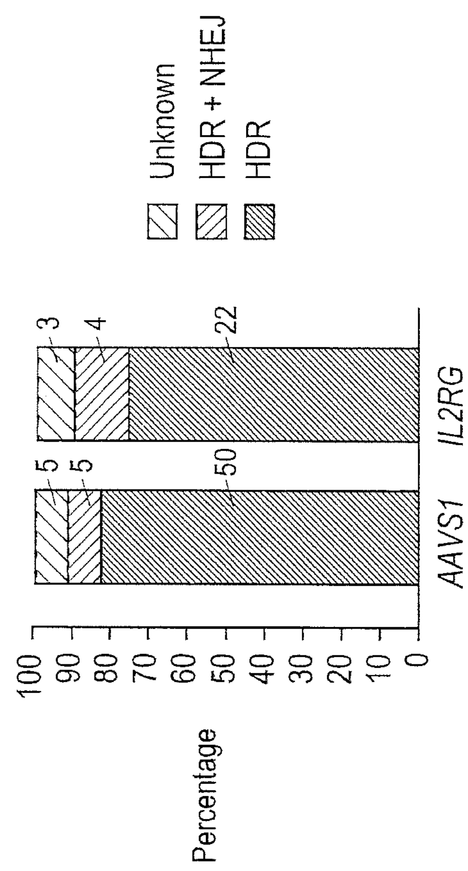
Figure 1J:
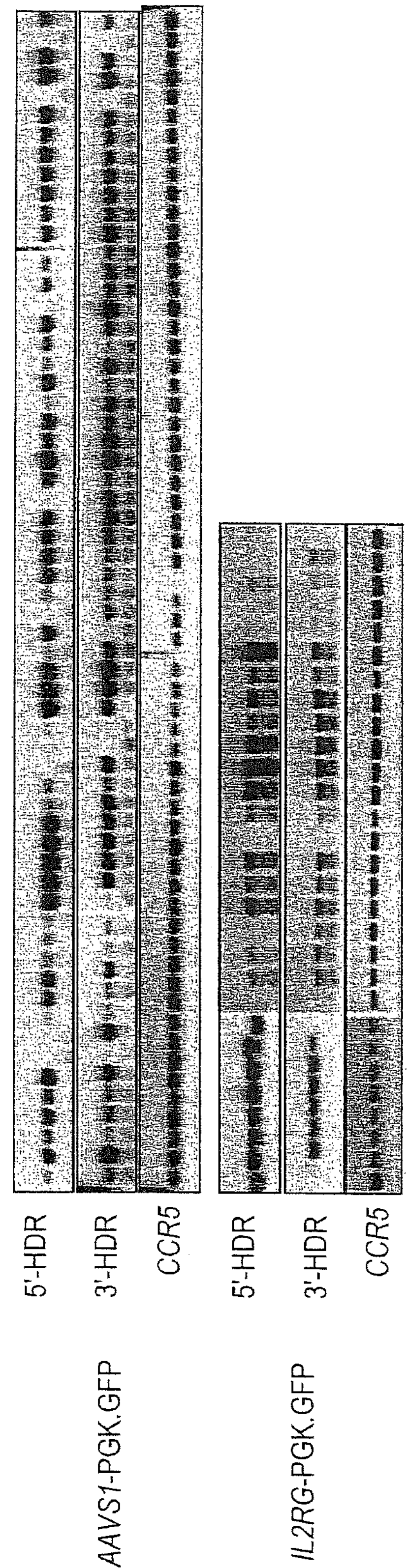
Figure 1K:
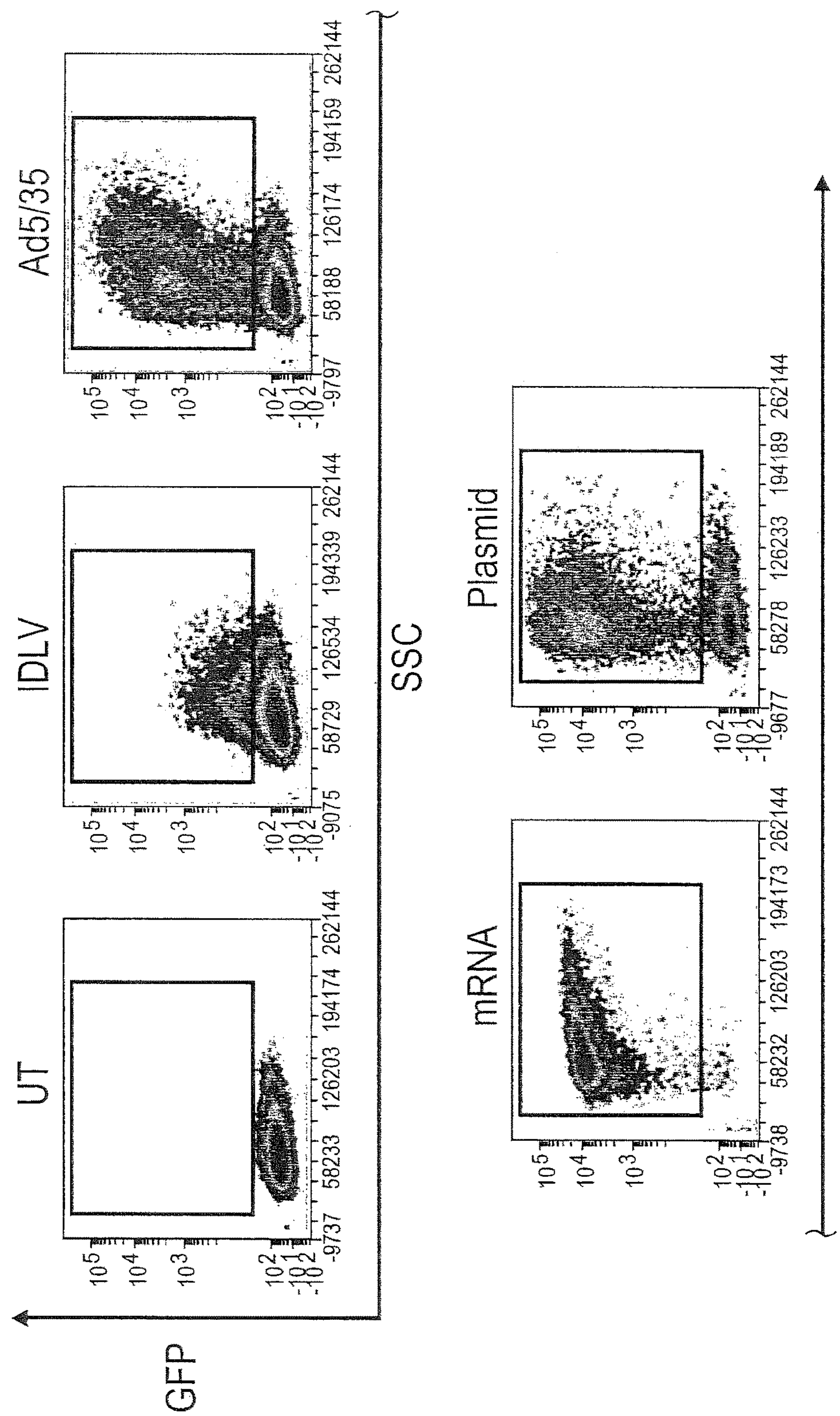
Figure 1L:
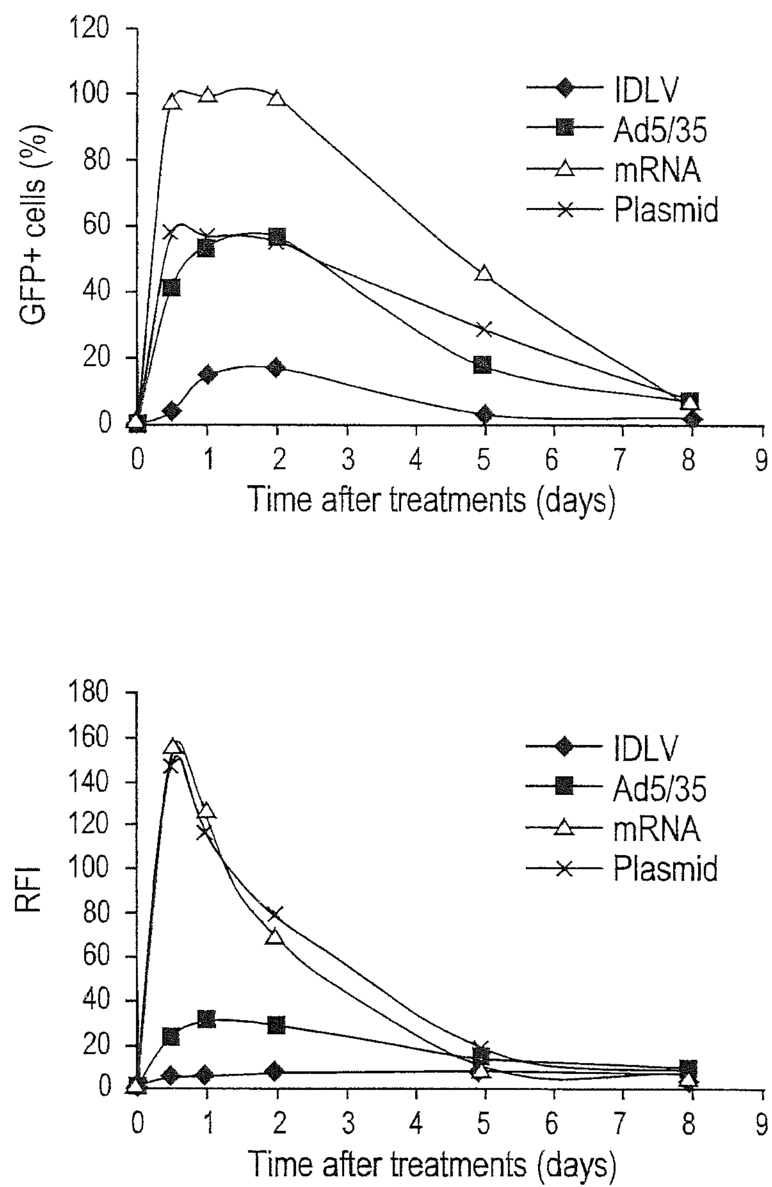

The acute cell loss observed in liquid culture also resulted in decreased numbers of colony-forming cells (CFC), when plated 24 hours after electroporation. However, the recovered cells gave rise to similar proportions of erythroid and myeloid colonies as the untreated controls (FIG. 1H). Importantly, GFP+ colonies of both types were found with the same frequency as observed for GFP+ cells in liquid cultures (FIG. 1I), demonstrating that gene targeting did not impair the clonogenic capacity of the cells recovered from the procedure. PCR analyses confirmed integration at the target site in >90% of the GFP+ colonies analyzed (n=68), confirming the high targeting specificity of the approach (FIG. 1J).

Example 3

Site-specific Integration in Long-term NSG Repopulating Cells

Figure 2A:
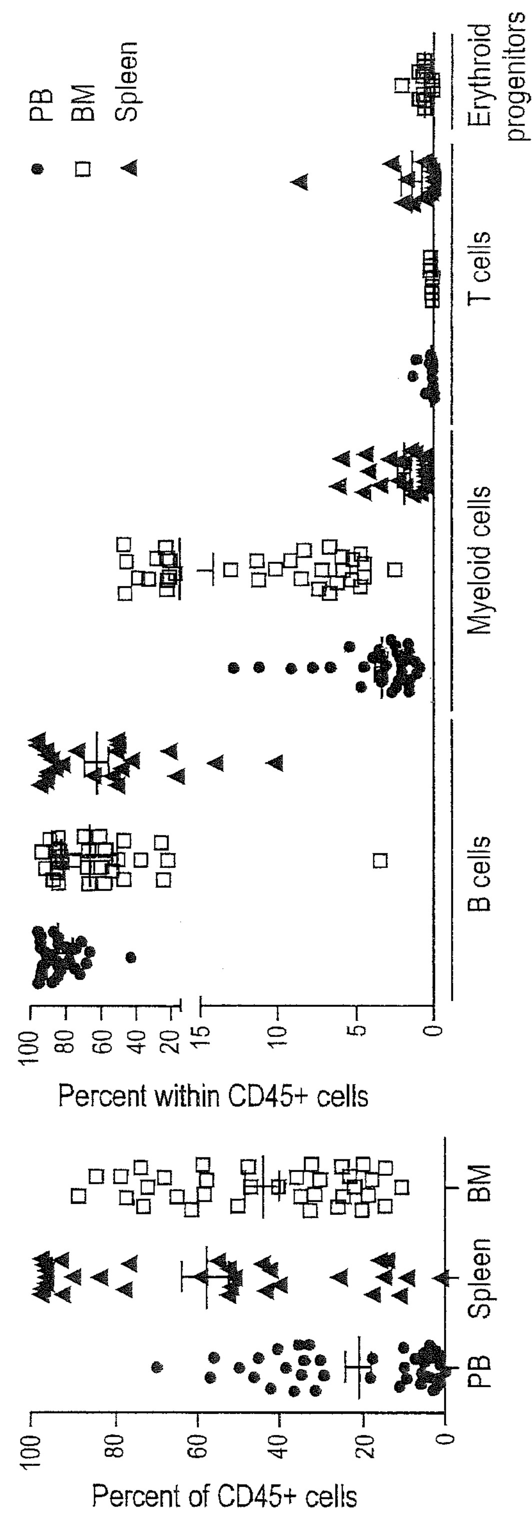
FIGS. 2A through 2G show transplantation of gene targeted CD34+ cells in NSG mice. 7-11 weeks old NSG mice were transplanted with $3\times10^{5}$ CD34+ cells treated as in FigurelB and monitored for engraftment of human CD45+ and GFP+ cells.

CD34+ cells that had undergone GFP-donor AAVS1 or IL2RG gene targeting were transplanted into NSG mice and monitored for human cell engraftment in the peripheral blood and, at the end of the experiment, in hematopoietic organs to assess the amount of targeted integration that had occurred in the HSC. Twelve weeks post-transplant mice were engrafted with human cells (FIG. 2A).

Figure 2B:
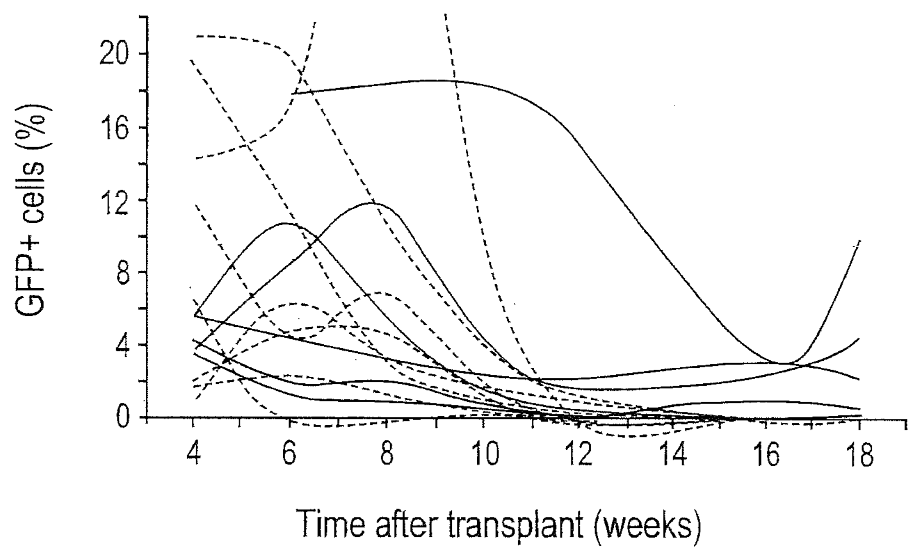

Engraftment levels varied among the mice, as expected, but mostly fell within the range observed for LV-transduced CD34+ cells in independent experiments. In the first 8 weeks post-transplant, the vast majority of mice (95%) contained a significant fraction of circulating GFP+ cells (mean 6.2±1.3%; n=22 mice on 5 different CB donors; FIG. 2B).

Figure 2C:
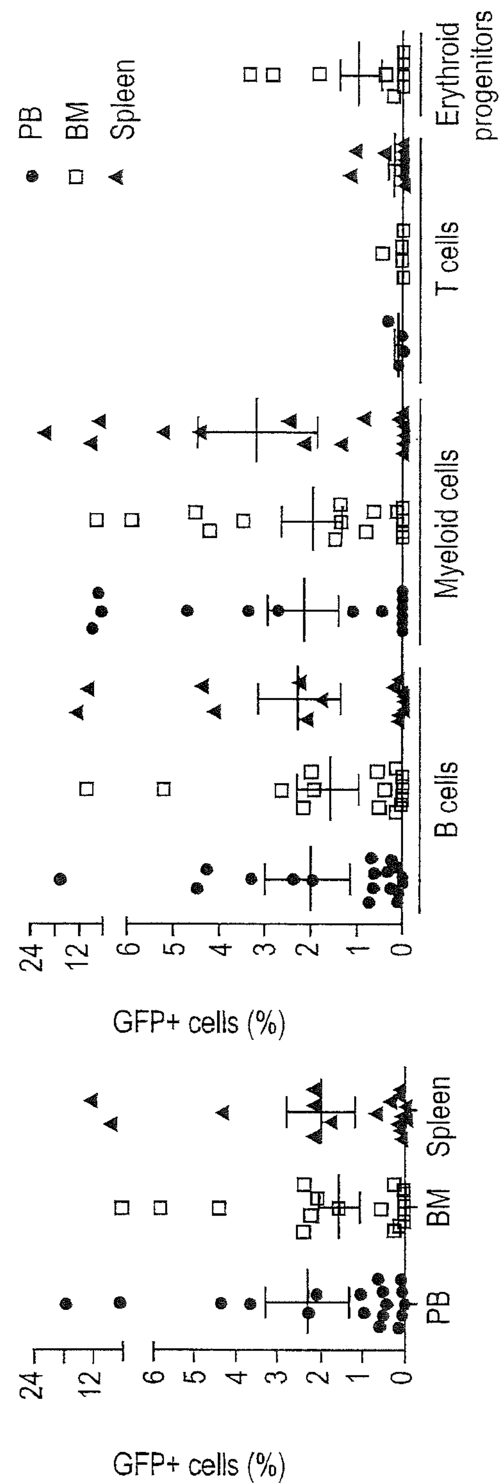

Upon exhaustion of the short-term human hematopoietic progenitors (after the $12^{th}$ weeks post-transplant), 42% of the transplanted mice maintained long-term GFP marking (n=41; 6 independent experiments performed on 13 CB donors). Importantly, end-point analyses performed on the peripheral blood (PB), spleen and bone marrow (BM) of the transplanted mice showed that GFP+ cells (mean 2±0.8%) were present within all human hematopoietic lineages, including lymphoid and myeloid cells, and erythroid precursors (FIG. 2C).

Figure 2D:
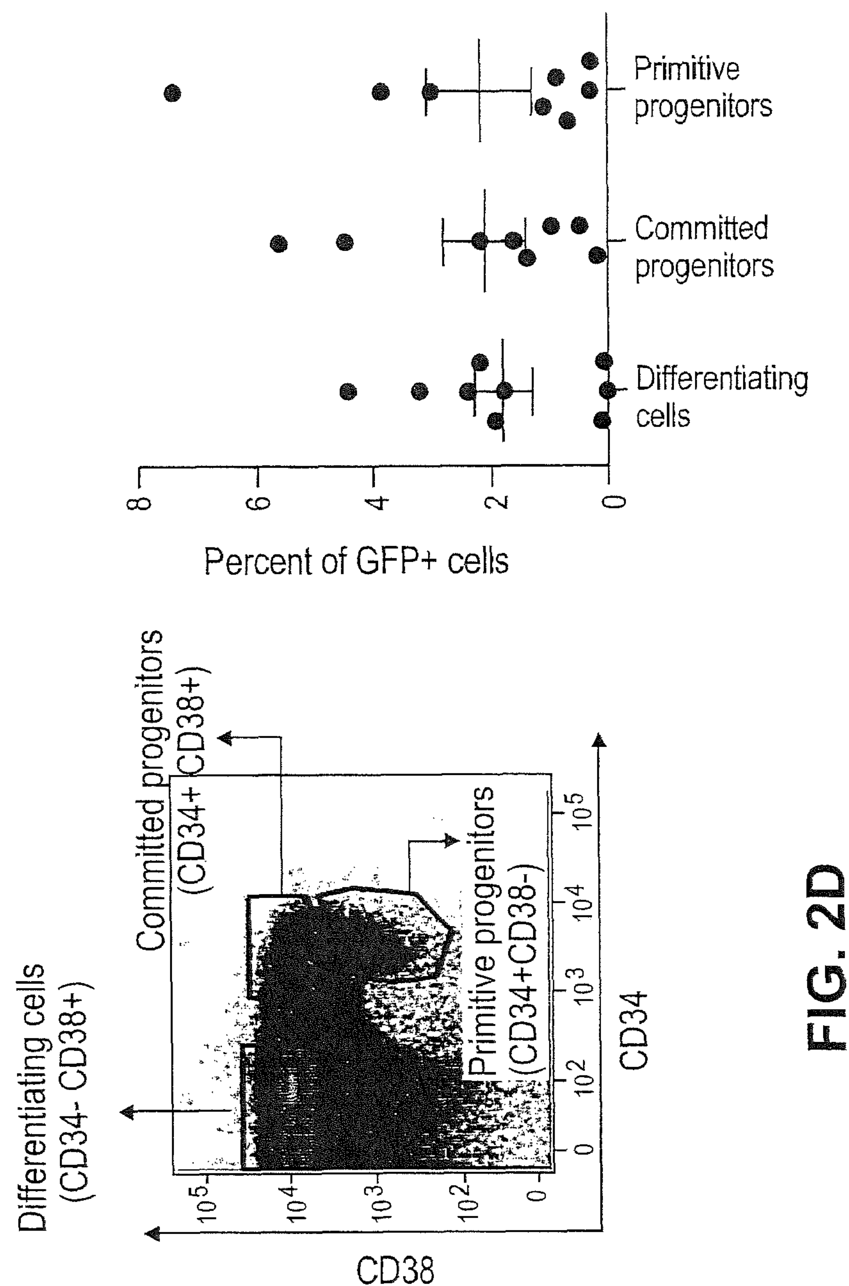
Figure 2E:
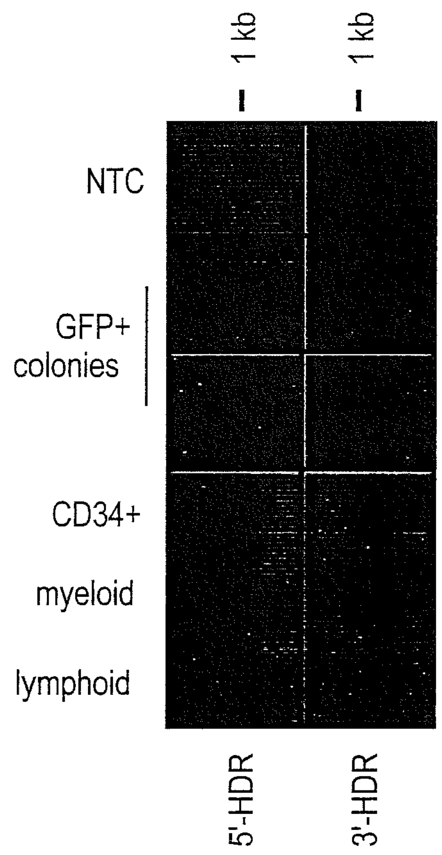
Figure 2F:
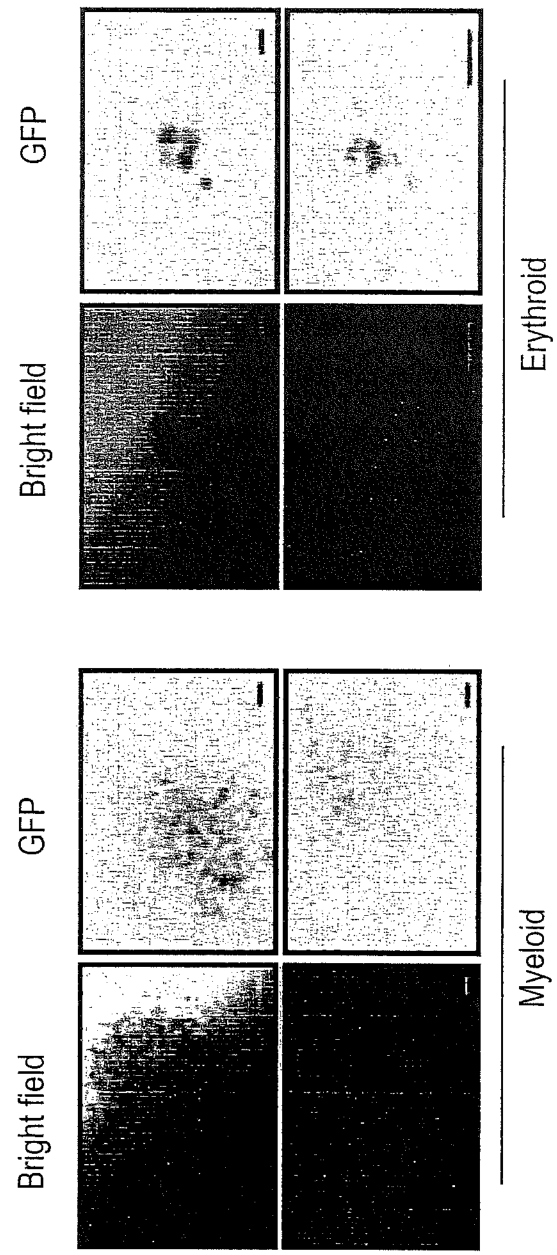
Figure 2G:
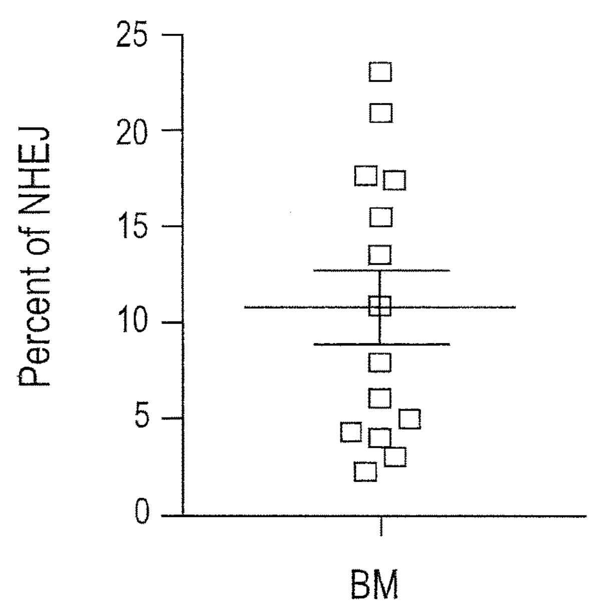

Human GFP+ progenitors were also present in the BM in similar percentages (mean 2.2±0.9%; FIG. 2D) among the more primitive progenitors (defined as CD34+CD38− cells), the committed progenitors (defined as CD34+CD38+ cells) and the differentiating cells (defined as CD34−CD38+ cells). PCR analyses performed on human lymphoid, myeloid and CD34+ cells purified from the spleen and BM of representative transplanted mice confirmed targeted integration (FIG. 2E). CFC assays on CD34+ cells purified from the BM of transplanted mice were also performed and GFP+ myeloid and erythroid colonies (microscopic images shown in FIG. 2F) were obtained showing targeted integration (FIG. 2E). BM analysis of the transplanted mice showed the occurrence of NHEJ-mediated indels in the ZFN target site in the majority of mice (64%, n=25 from 3 independent experiments; FIG. 2G) and at higher levels than observed for GFP marking, indicating that DNA DSB induction and repair by either HDR or NHEJ are compatible with hematopoietic repopulation.

Overall, these data show that the gene targeting protocol achieved site-specific integration in multi-potent long term NSG repopulating cells (SRC).

Example 4

Population Analysis Uncovered Low Targeting Efficiency in Primitive Progenitors

The in vivo studies revealed that only a fraction of mice (~40%) were long-term repopulated with GFP+ cells, and that the mean percentage of GFP+ cells in these mice was approximately 2%. These figures appear lower than expected from the transplantation of CD34+ cells showing ~5% targeting efficiency in vitro according to the following model. The NSG mice showed in FIG. 2 were transplanted with $3\times10^5$ treated CD34+ cells with 5% GFP marking. If we consider that only a small fraction of the injected CD34+ cells represent SRC and apply Poisson's statistics for random distribution of independent events to the number of mice engrafted with GFP+ cells, we would conclude that 1 in $3\times10^4$GFP+ cells is a SRC (from the 60% of mice lacking GFP+ cells we calculated distribution of 0.5 GFP+ SRC per mouse, which, considering the injection of $1.5\times10^4$GFP+ cells ($3\times10^5$ cells with 5% GFP marking), give an SRC frequency of 1 in $3\times10^4$ GFP+ cells; $3\times10^5\times0.05/0.5=3\times10^4$). If this calculation is right, each mouse should receive on average 10 SRC (GFP − and +) and the average contribution of a GFP+ SRC in a positive mouse should reach 10% of the human graft. The lower figure observed in the experiments (2%; p value by Wilcoxon test) indicates that there are more SRC injected per mouse than estimated based on the GFP marking and may suggest that either SRCs are targeted less efficiently than the bulk CD34+ cells, or the gene targeted SRCs have a competitive disadvantage in vivo. This data suggested that either SRCs were targeted less efficiently than the bulk CD34+ cells, or the gene targeted SRCs had a competitive disadvantage in vivo.

Figure 3A:
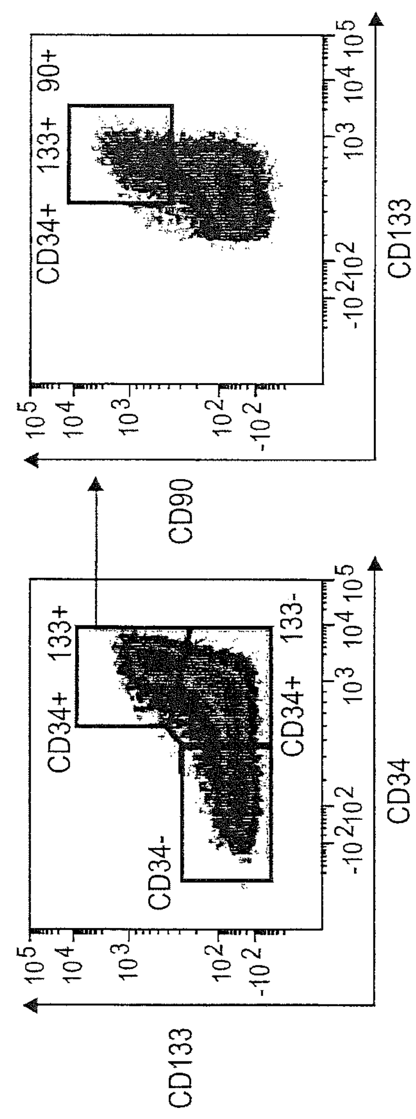
FIGS. 3A through 3J show gene targeting efficiency in primitive versus committed progenitors.

To address this point, we compared the percentages of GFP+ cells among different subpopulations of cultured CD34+ cells. We exploited surface markers broadly used to prospectively identify early (CD34+CD133+) and committed (CD34+CD133−) progenitors from the differentiated cells (CD34−; FIG. 3A). Within the former population, we further defined a subset comprising the more primitive progenitors based on expression of the CD90 marker (CD34+CD133+CD90+).

Figure 3B:
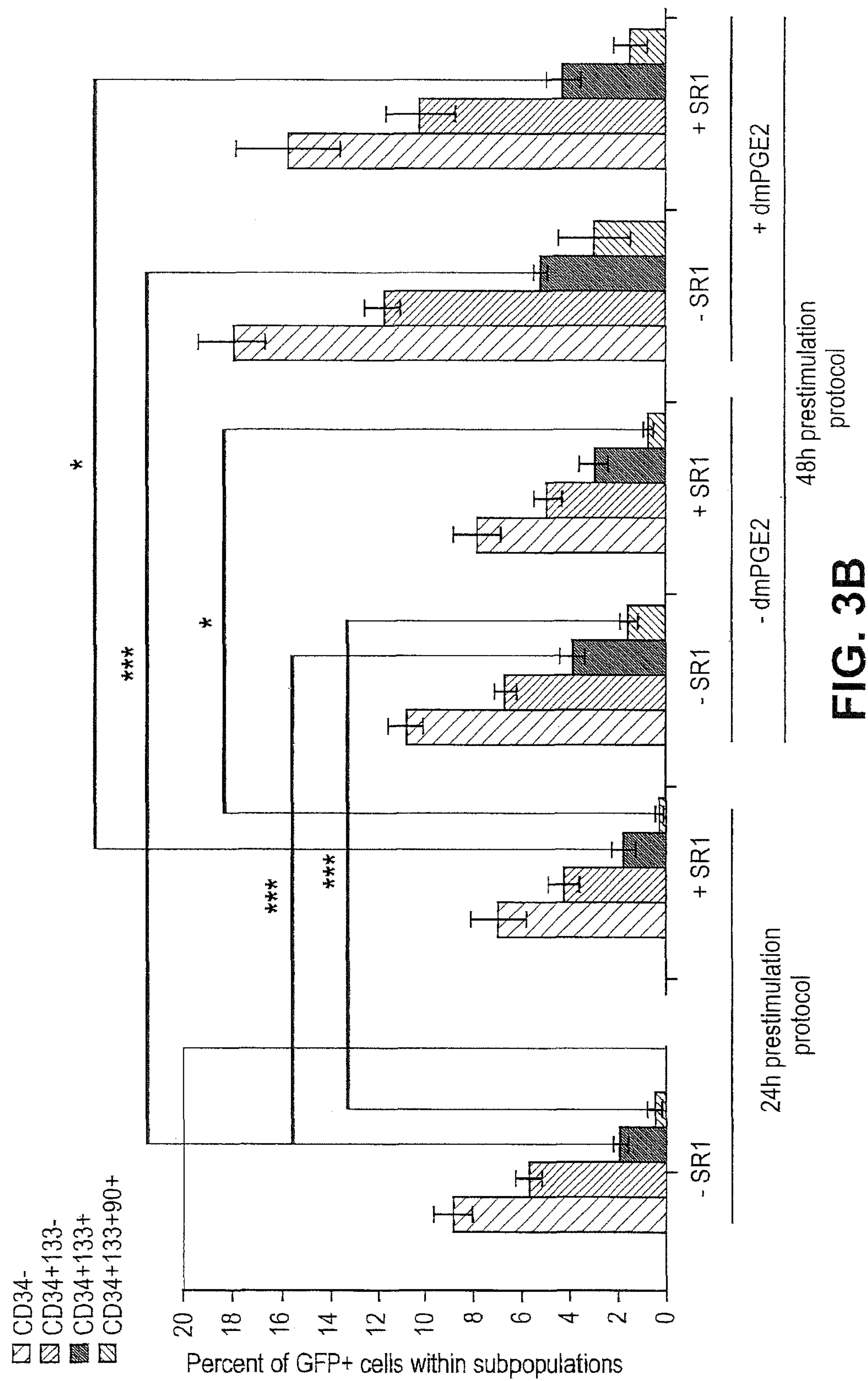

We found a decreasing frequency of GFP+ cells when moving from the differentiated cells up the progenitor/stem cell hierarchy (FIG. 3B, left panel). Strikingly, in the most primitive population, the percentage of GFP+ cells was 20-fold lower than that measured in the more differentiated cells. We thus investigated the potential rate-limiting steps for gene targeting in the more primitive progenitors. We first measured the efficiency of transgene expression upon mRNA electroporation using GFP and found it to be similar among the subpopulations and only slightly lower for the more primitive cells. On the contrary, the level of NHEJ induced at the ZFN target site at early time points was very robust in the more primitive subsets (CD133+CD90+ or CD90−) as compared to the committed progenitors (CD34+CD133−) and differentiated cells (CD34). The higher level of NHEJ in the more primitive cells was less evident at later time points of culture, potentially due to the more sensitive nature of this cell population under these conditions (FIG. 6B). Indeed, induction of apoptosis was highest in the most primitive CD133+CD90+ subset (FIG. 6C).

Taken together these data point to the relative fragility of the most primitive CD133+CD90+ subset during the ex vivo manipulation perform here, but also suggest that they are less permissive to HDR and/or donor template delivery in our experimental conditions.

We achieved efficient delivery of artificial nucleases and template DNA by combining mRNA transfection and IDLV infection. RNA transfection drives a robust but short-lived spike of ZFNs expression, allowing proficient activity of the nucleases at the genomic target sites while avoiding prolonged exposure and integration of the ZFN-expressing vectors. IDLV proved more efficient and was better tolerated than plasmid DNA to generate template DNA for HDR.

This delivery strategy allowed us to obtain efficient targeted integration into bulk CD34+ cells, which can be relevant in experimental or clinical settings aimed at genetic modification of committed progenitors. However, analysis of the cell populations comprising the heterogeneous CD34+ cell pool uncovered differences in gene targeting efficiency, with the more primitive cell types being less targeted. Whereas ZFNs expression and activity reached similar levels in all cell types, there was a substantially lower recovery of primitive cells harboring HDR-mediated integration. Our investigation indicates that primitive HSC are more sensitive than committed progenitors to gene targeting procedure.

In addition, it was shown also for other stem cell types that they can undergo transient cell cycle arrest, apoptosis, differentiation or senescence according to the strength and duration of a genotoxic insult. Our results suggest that the more quiescent HSC are less proficient at performing HDR than committed progenitors, likely because of slow cycling, as shown by the much lower HDR/NHEJ ratio measured both in vitro and in vivo at the ZFN target sites.

By delaying the time of treatment and exploiting recently described protocols for ex vivo maintenance and expansion of HSCs, we were able to partially relieve the block to HDR. This effect is likely due to an increased transit through the S/G2 phases of the cell cycle, when HDR can occur, and possibly, up-regulation of its endogenous machinery. Other beneficial effects might be increased permissiveness to gene delivery, more efficient mRNA translation and reduced growth arrest and apoptosis in response to the gene targeting procedure. Although dmPGE2 was shown to stimulate survival, proliferation and self-renewal of HSC, we did not identify the mechanism(s) that promote targeted integration. Since we did not observe significant differences in the apoptotic rate of cells treated with or without dmPGE2, it is possible that its effect is related to increased activation/proliferation. On the other hand, SR1 treatment did not significantly influence the targeting efficiency but helped maintain the more primitive fractions in culture, thus increasing the overall yield of gene targeted HSC.

IDLV can also be trapped at sites of NHEJ, albeit with low efficiency, as we previously reported. Indeed, we detected some evidence of NHEJ-mediated integration of the donor template at the ZFN target site in long-term repopulating HSC. This event can also contribute to transgene expression and be exploited for gene correction by forcing splicing into the corrective cDNA, potentially compensating for low HDR proficiency.

Our claim of successful genome editing in human HSC relies on the surrogate readout of long-term multilineage repopulation of the blood and bone marrow of transplanted NSG mice by transgene positive cells, and by the derivation of gene-targeted CFC from CD34+ cells retrieved from the mice. Although we could not assess the clonal composition of the human cell graft, the relatively homogenous percentage of GFP+ cells across different lineages in most mice further supports successful targeting of multipotent progenitors and stem cells. Moreover, the high level of NHEJ measured at the ZFN target sites in the human cell grafts supports efficient engraftment of SRC previously exposed to high ZFN activity.

Example 5

Figure 3C:
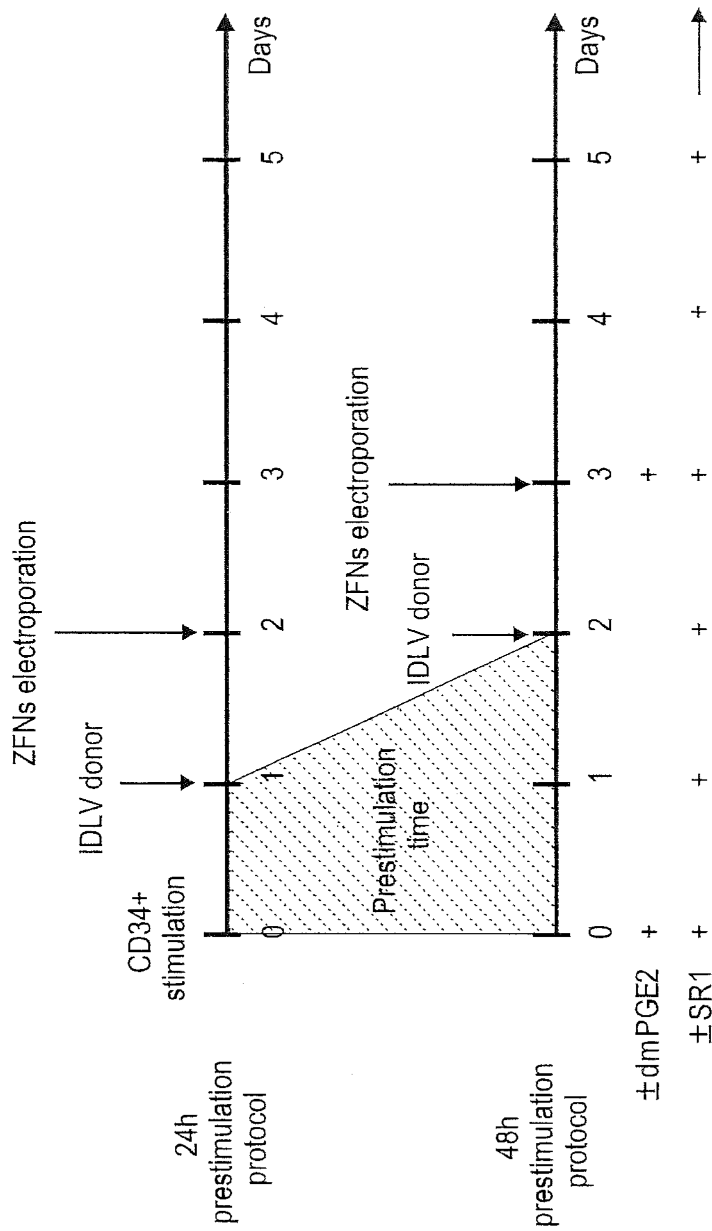
Figure 3D:
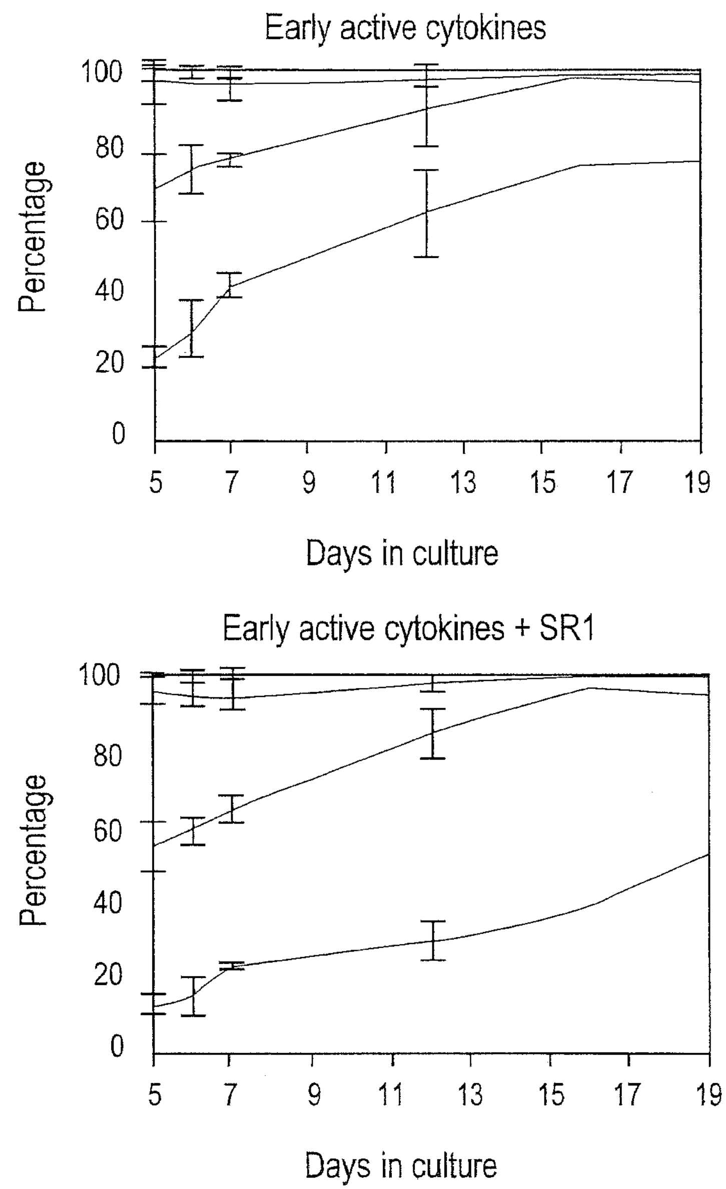

Tailoring Culture Conditions to Promote HSC Expansion Increases Gene Targeting Because cell cycle progression is a major requirement of HDR, and activation of the more primitive progenitors may require longer stimulation, we postponed the gene targeting procedure to the third day of culture (FIG. 3C). At this time, the cells are also likely to become more permissive to LV transduction. However, since increasing times of culture lead to increased differentiation, we also tested addition of the Aryl Hydrocarbon Receptor Antagonist (StemRegenin 1, SR1) and/or 16.16 dimethyl-prostaglandin E2 (dmPGE2) to the culture medium to promote progenitor expansion in conditions that have been reported to preserve the stemness of these cells (FIG. 3D).

Figure 3E:
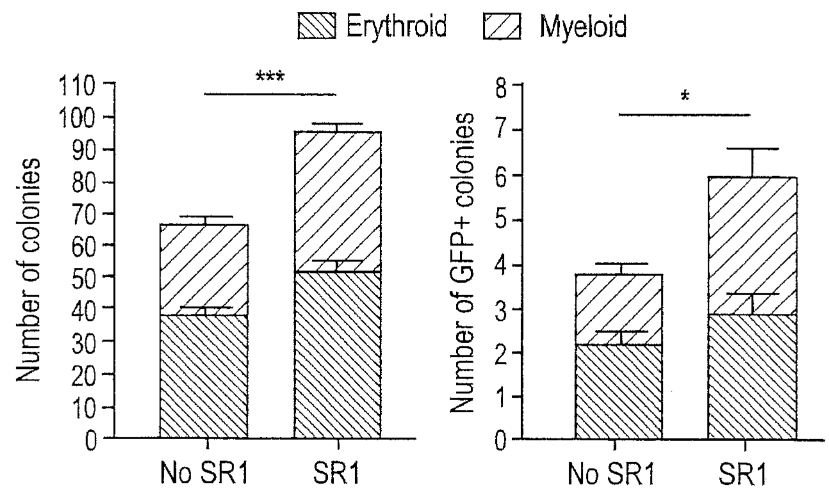
Figure 3F:
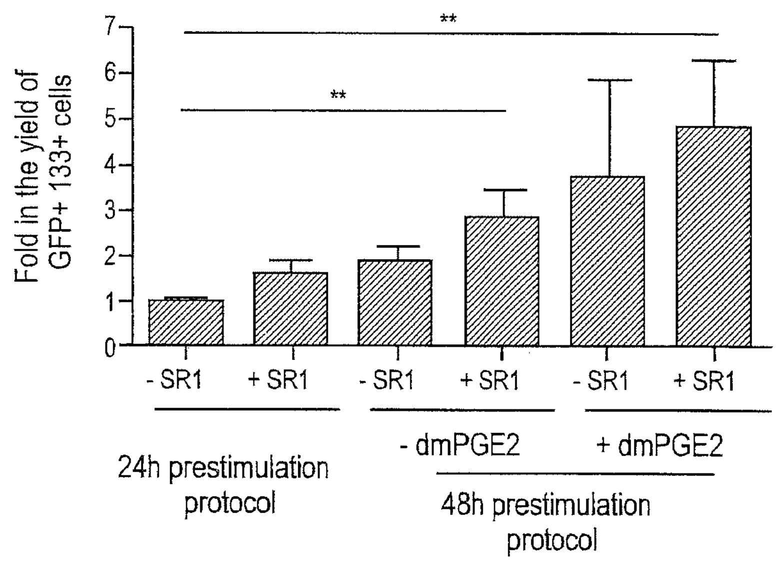
Figure 3G:
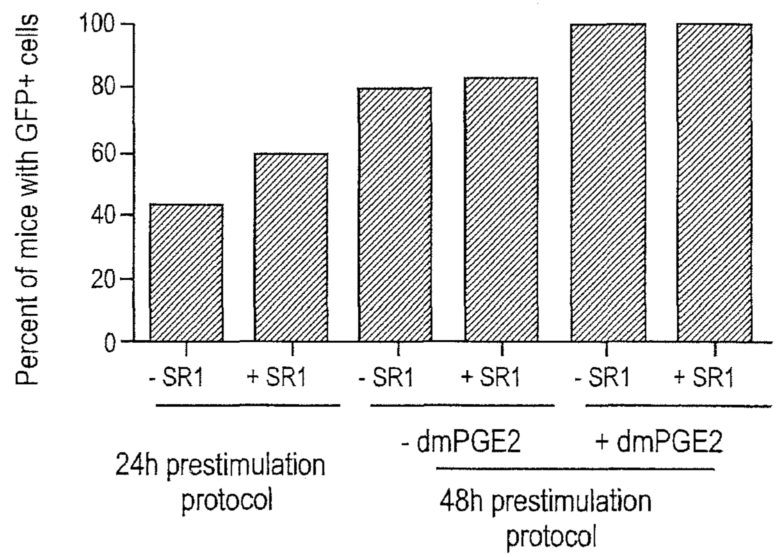
Figure 3H:
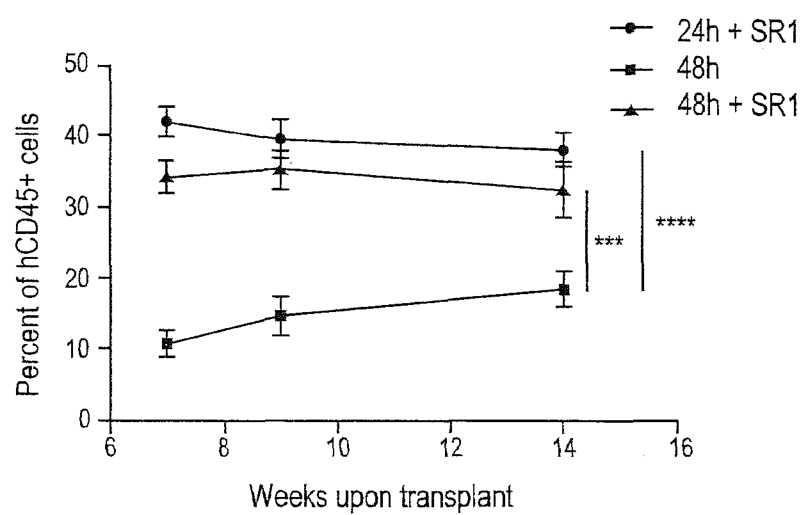
Figure 3I:
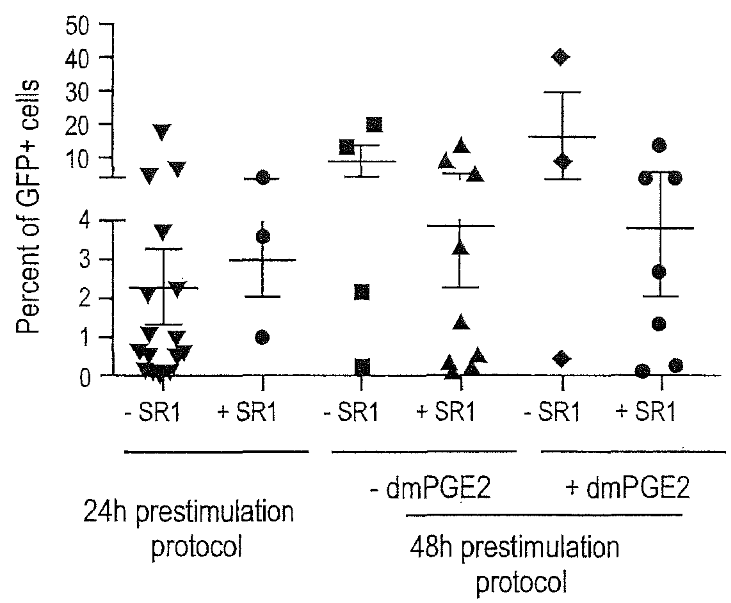
Figure 3J:
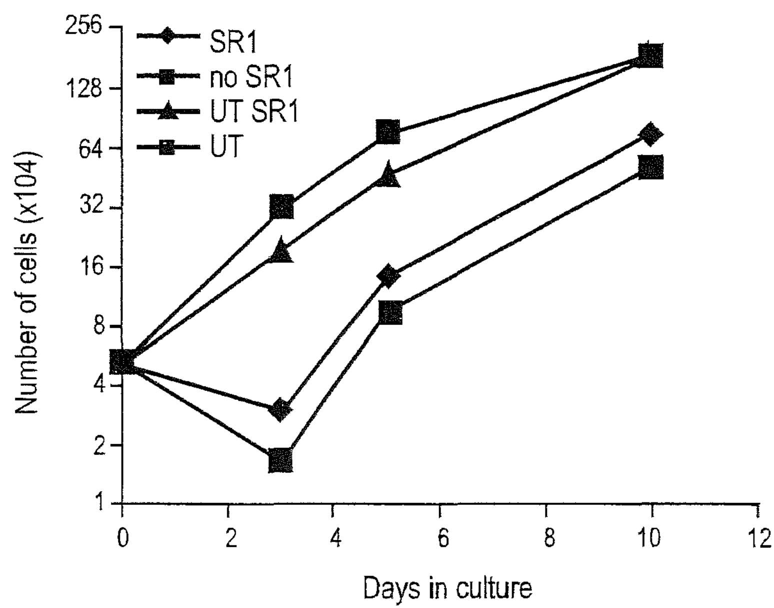

The delayed protocol resulted in a significantly increased (≥2-fold) percentage of GFP+ cells in the more primitive cell types (FIG. 3B, right panels). The addition of SR1 slightly reduced the percentage of GFP+ cells observed within each subpopulation but increased the overall yield of GFP+ CFC and early (CD133+) progenitors, consistent with the increased proportion of immature cells in SR1-treated cultures (FIG. 3E, FIG. 3F and FIG. 3J).

The addition of dmPGE2 further increased the percentage of GFP+ cells in all subpopulations, showing additive effects with SR1. Most importantly, both the delayed treatment and the addition of SR1 and dmPGE2 increased the fraction of mice successfully engrafted with GFP+ cells, which reached 100% when used in combination (FIG. 3G).

Figure 7A:
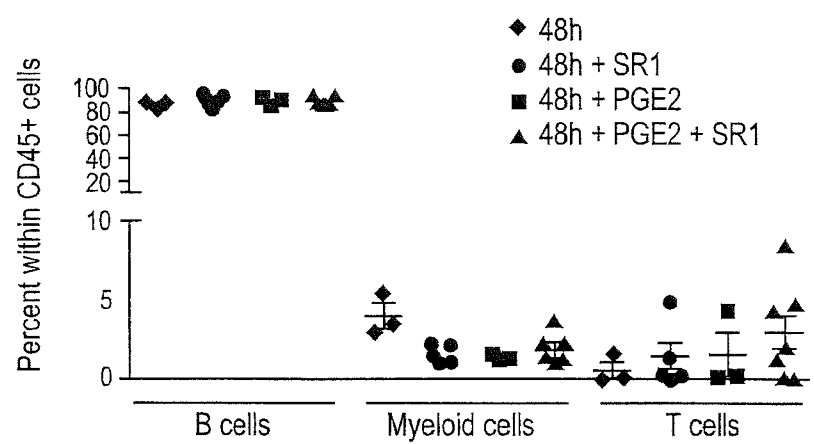
FIGS. 7A through 7D show long-term multilineage engraftment in NSG mice of gene targeted CD34+ cells treated with the improved protocols.
Figure 7B:
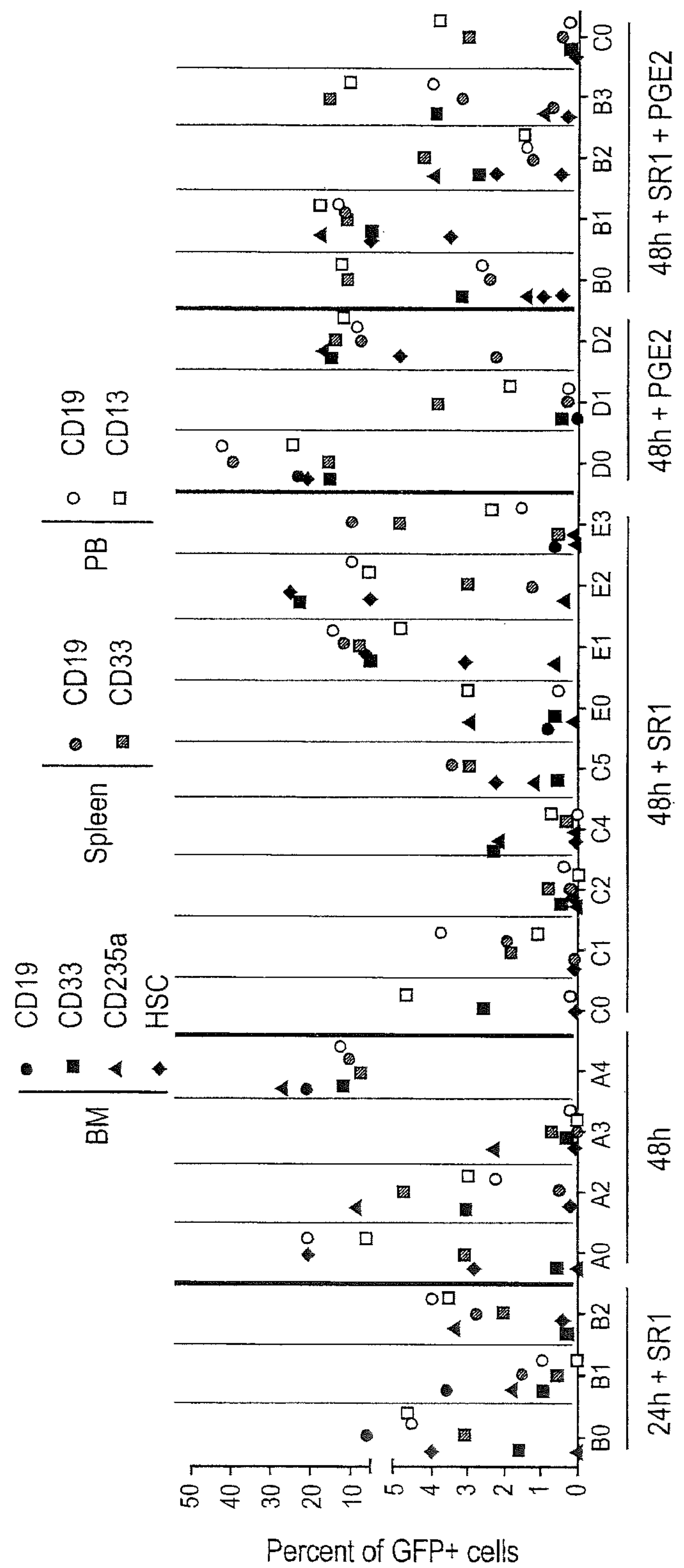
Figure 7C:
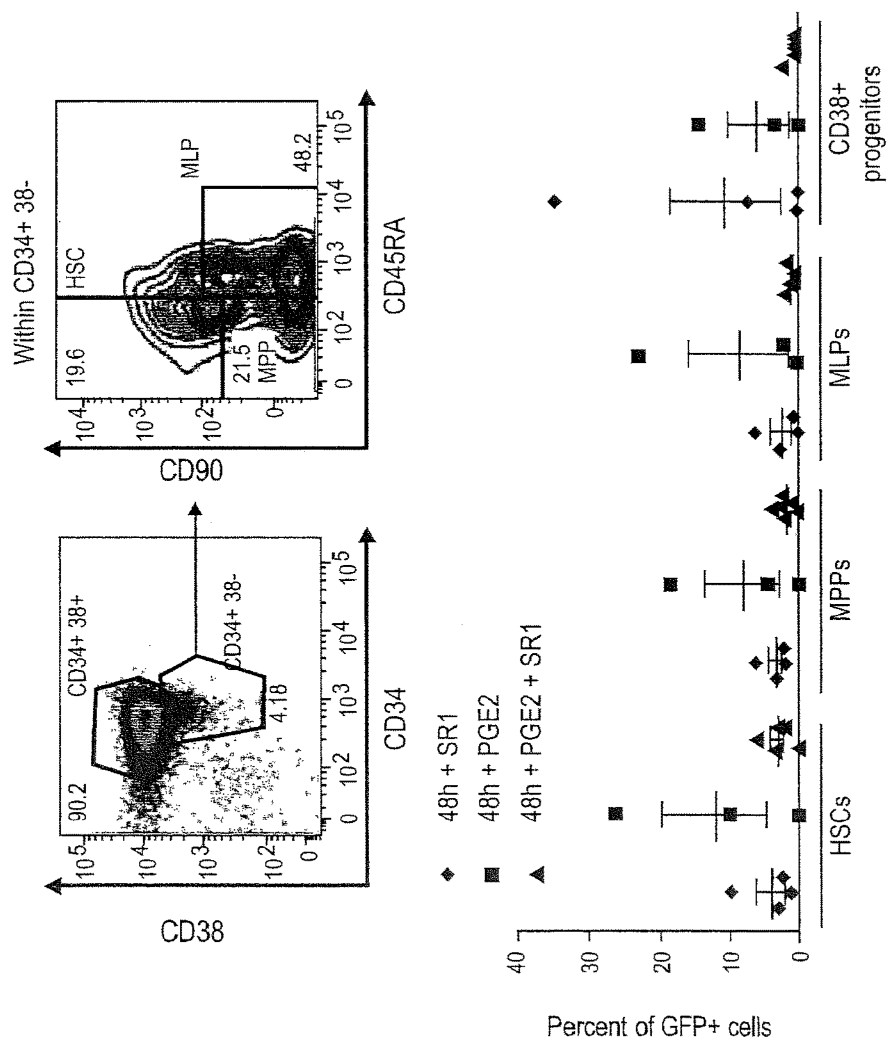
Figure 7D:
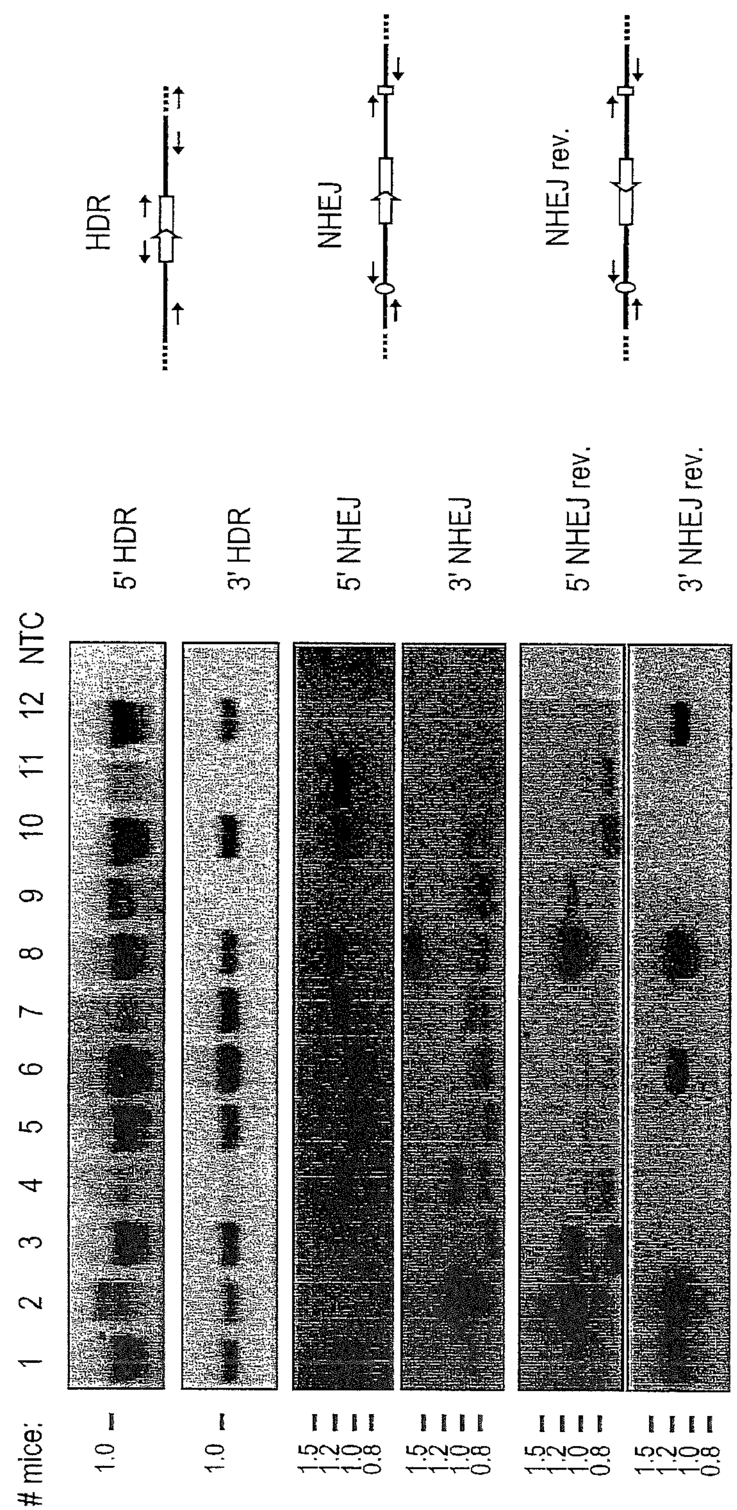

Total human cell engraftment in the mice was significantly increased after SR1 addition to the culture (FIG. 3H) and was stable long term, without skewing in the differentiation pattern of the treated cells (FIG. 7A). Consistently with the increased GFP marking observed in vitro in the more primitive cells, the mean percentage of GFP+ cells long-term engrafted in vivo increased with all types of delayed treatments (FIG. 3I). GFP+ cells contributed to multiple lineages and to the progenitor compartment in most of the mice (FIGS. 7B and 6C). Molecular analysis on bone marrow cells showed evidence of targeted integration at the IL2RG locus (FIG. 7D). Between 15-23 weeks after the primary transplant, human CD34+ cells were purified from the BM of 11 mice from (c) and transplanted (one mouse to one mouse) into 7-11 weeks old NSG mice. Secondary recipient mice were monitored for engraftment of human CD45+ and GFP+ cells at 8 and 12 weeks post-transplant on PB, and on BM at the end of the experiments. Serial transplant of purified CD34+ cells from the BM of primary mice showed engraftment and differentiation of targeted GFP+ cells in secondary recipients.

Overall, these data indicate that by tailoring experimental conditions we could improve the yield and frequency of targeted long term SRC.

Example 5

Figure 4A:
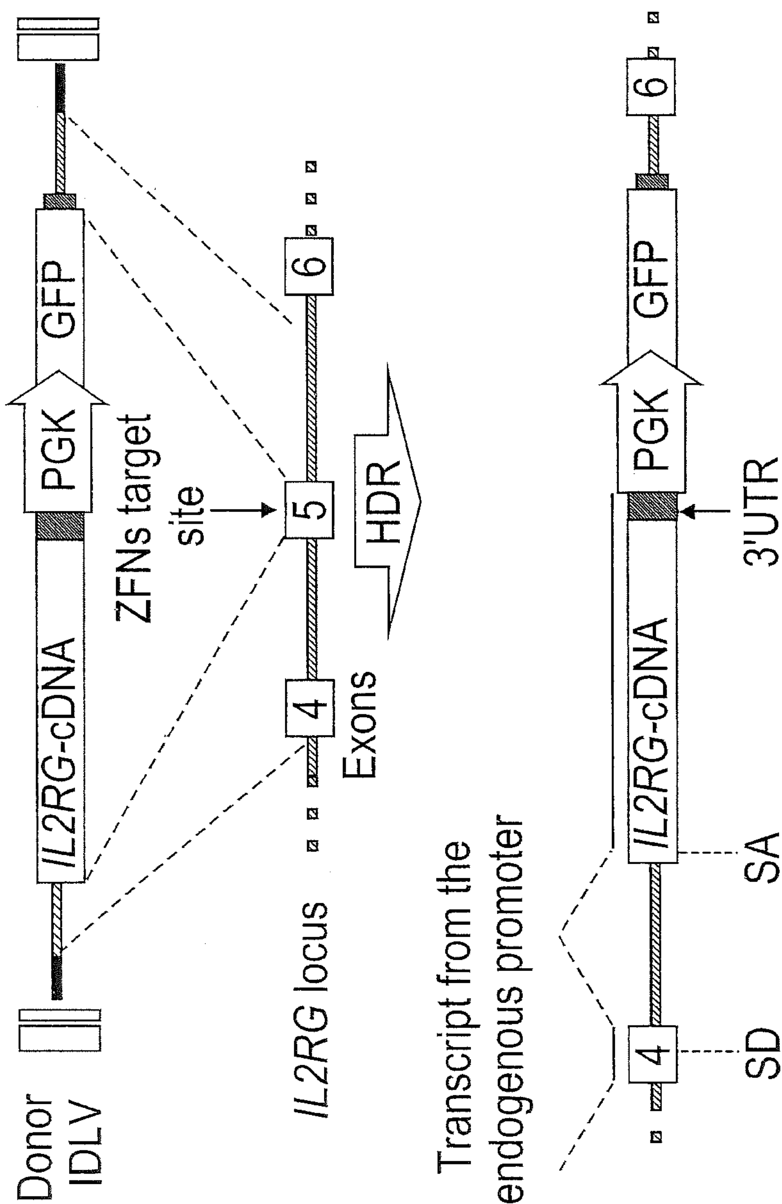
FIGS. 4A through 4J show functional reconstitution of IL2RG in the lymphoid progeny of HSC.

Functional Reconstitution of IL2RG Gene in the Lymphoid Progeny of Gene Edited HSCs The gene targeting construct used in the experiments described in FIG. 3 was designed to insert a cDNA comprising exon 5 to 8 of the IL2RG gene together with the GFP expression cassette into the ZFN target site of the IL2RG gene of CD34+ cells from healthy male donors (FIG. 4A). In this way, the cDNA is transcribed from the endogenous IL2RG promoter and spliced into its upstream exons, thus providing a platform for correcting all SCID-X1 causing mutations downstream of exon 4.

Figure 4B:
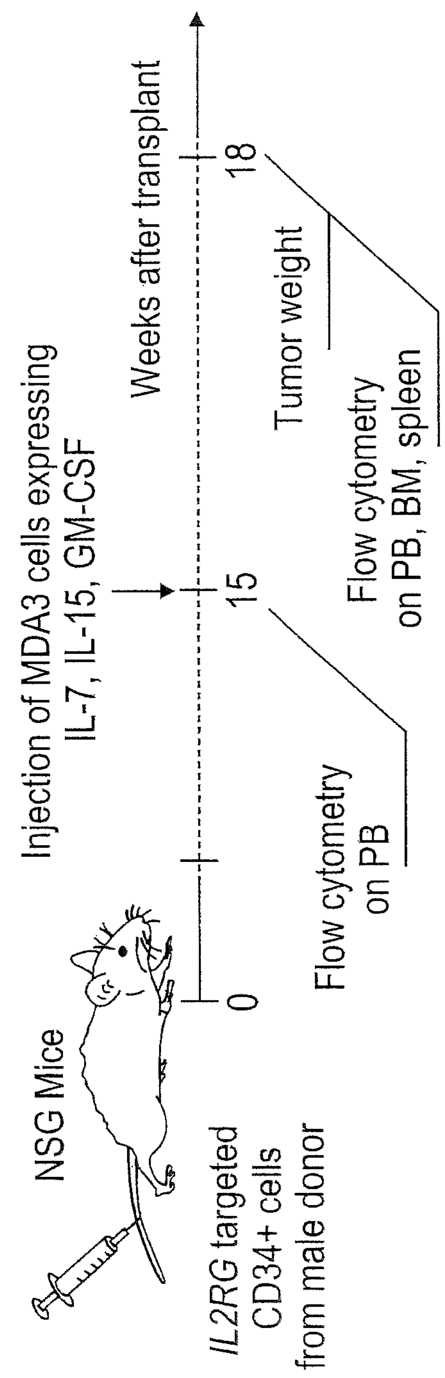

In order to assess functional reconstitution of the targeted gene, we challenged the repopulated mice with a human tumor model previously generated to study immune responses in human hematochimeric mice (FIG. 4B). This tumor cell line was engineered to express human IL-7, IL-15 and GM-CSF and allowed improved reconstitution of NSG mice with functional human T and NK cells that eventually rejected the tumor graft. These cell types are strictly dependent on IL2RG expression for survival and activity and are absent in SCID-X1 patients.

Figure 4C:
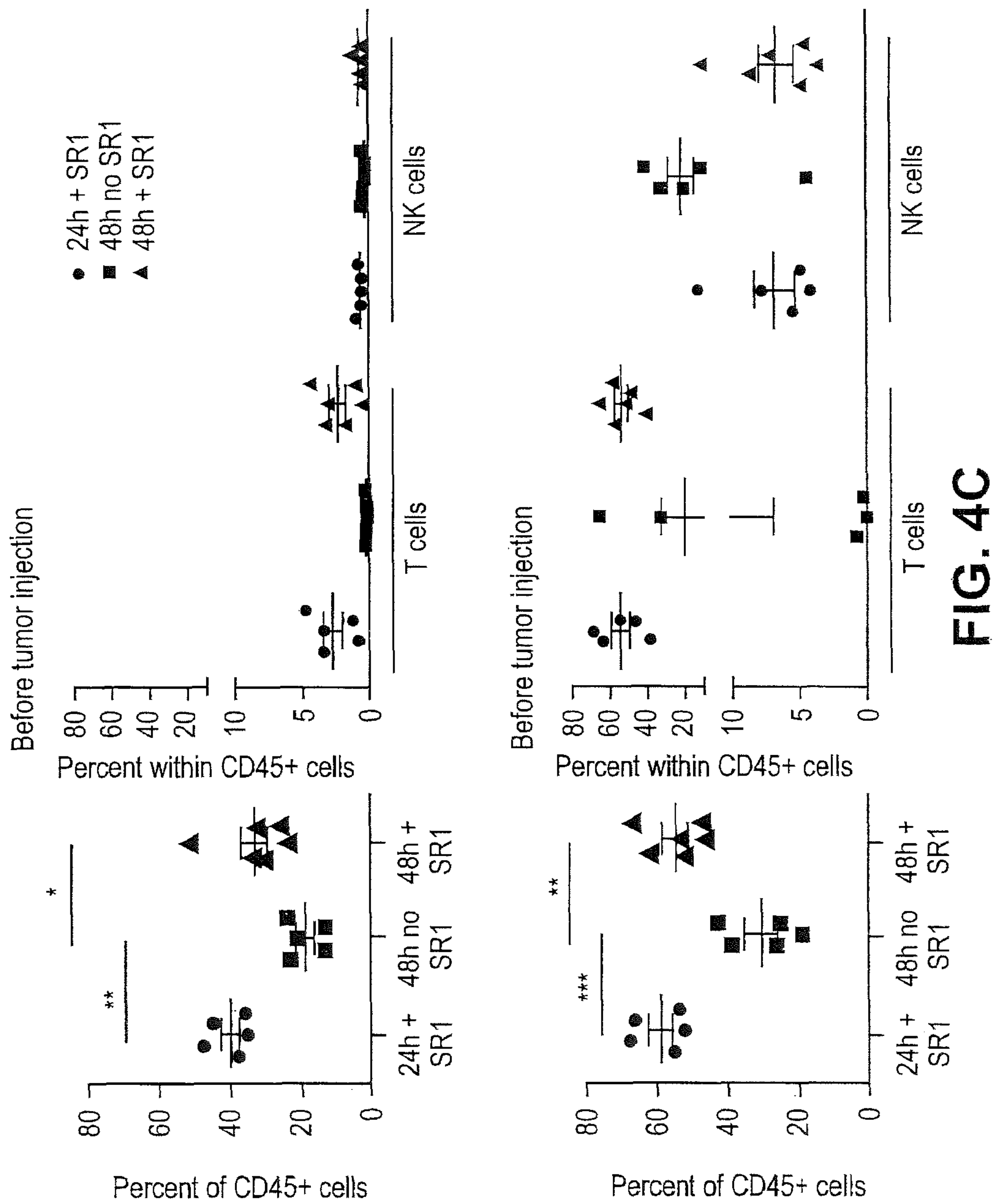
Figure 4D:
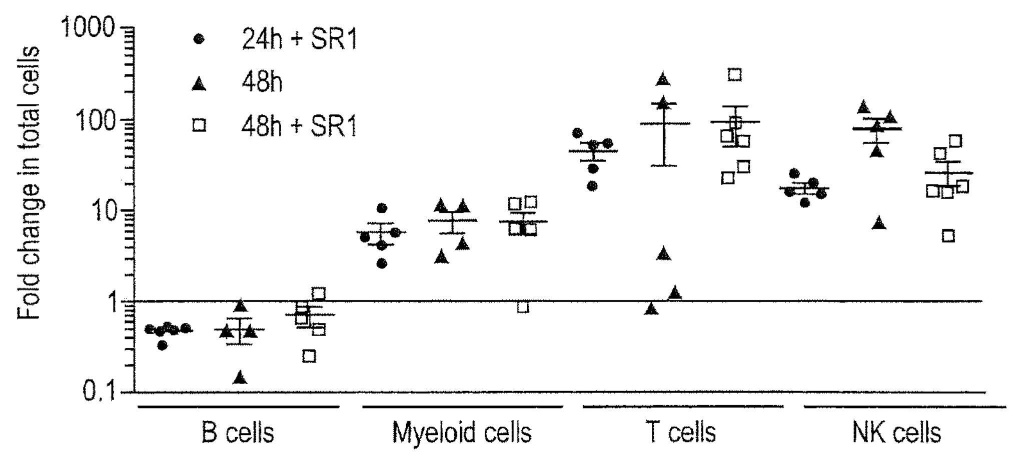
Figure 4E:
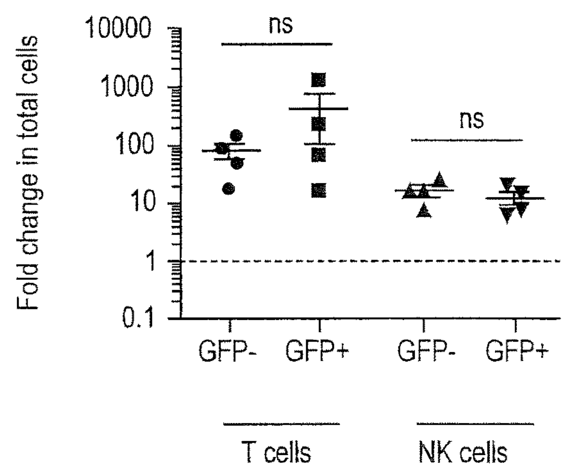
Figure 4F:
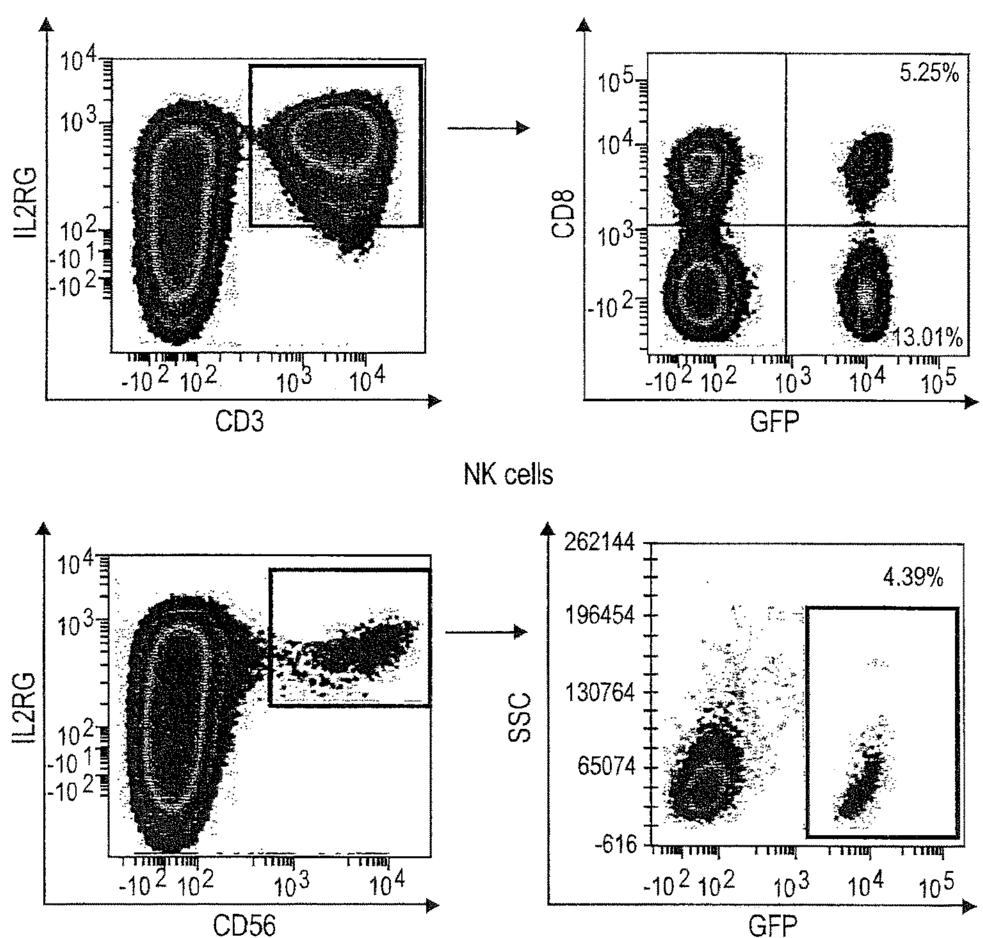

Upon tumor challenge, we observed a massive (mean 130±40-fold) expansion of the human T and NK lineages in the repopulated mice (FIG. 4C, 4D). Importantly, GFP+ T and NK cells expressed IL2RG on the cell surface (FIG. 4E) and expanded similarly if not more than their GFP negative counterparts in all mice (FIG. 4F).

Figure 4G:
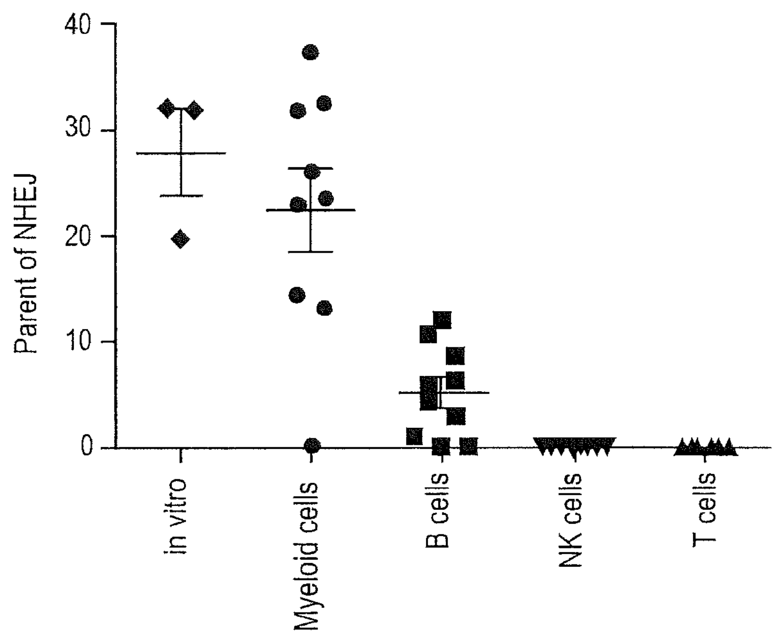
Figure 4H:
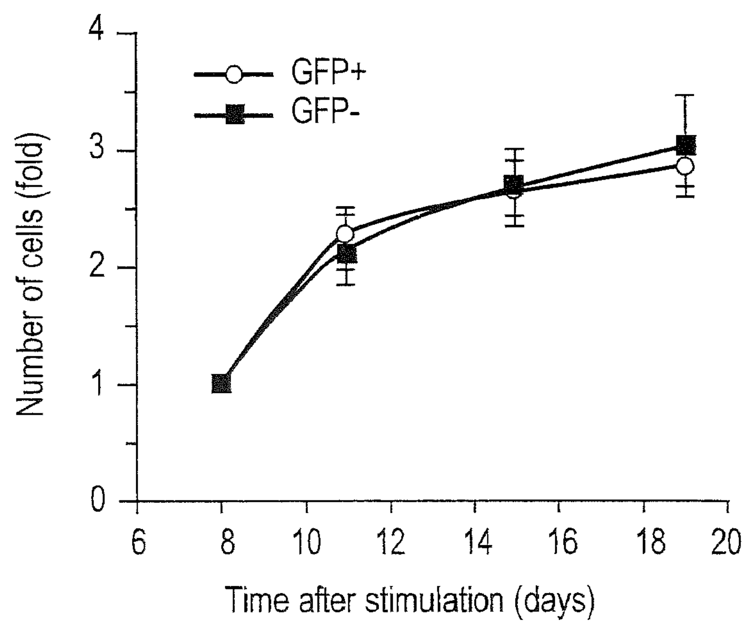

We then measured the extent of NHEJ at the targeted IL2RG locus in human myeloid and lymphoid cells sorted from the repopulated mice (FIG. 4G). Whereas myeloid cells showed high levels of NHEJ, comparable to those observed in the CD34+ cells pre-transplant, B cells showed very little, and T and NK cells virtually none.

These findings reflect the dramatic counter selection of lymphoid cells carrying a disrupted IL2RG gene, as it naturally occurs with inherited SCID-X1 alleles, and confirm the functionality of the reconstituted gene in the expanded GFP+ cells.

Figure 4I:
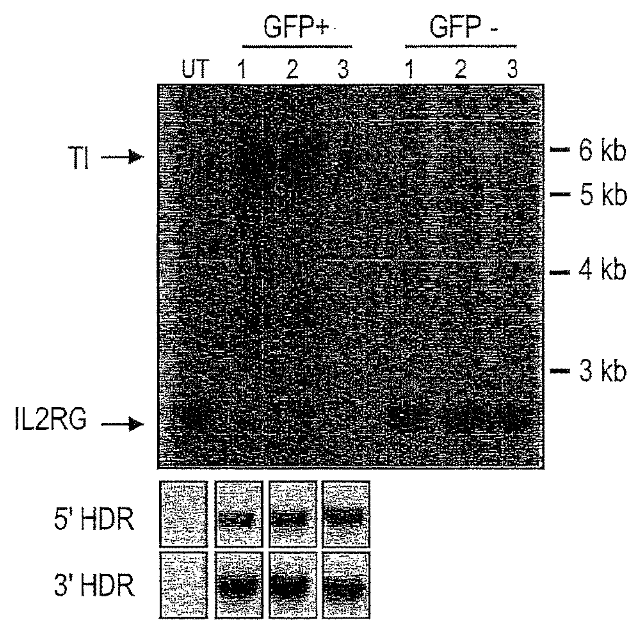

We then assessed the TCR repertoire of T cells from the engrafted mice by complementarity-determining region 3 spectratyping analysis and found a substantial TCR diversity with an almost overlapping polyclonal pattern between the GFP+ and GFP− sorted cell subsets (FIG. 4I). Viable GFP+ and GFP− T cells harvested from the transplanted NSG mice or of T cells purified from human PB of healthy donor (HD T-cells), cultured in presence (with cytokines) or absence (without cytokines) of human IL-7 and IL-15 were assessed and GFP+ and GFP− T cells harvested from mice were activated ex vivo with beads coated with CD3 and CD28 specific antibodies, and cultured with IL-7 and IL-15. CD4 and CD8 composition of GFP+ and GFP− cells, was measured during the ex vivo culture, including CD4, CD8, T stem memory cells (TSCM), which are CD62L+CD45RA+, T central memory (TCM) which are CD62L+CD45RA−, T effector memory (TEM) which are CD62L− CD45RA− and terminal effectors (TEMRA) which CD62L− CD45RA+ assessment. IL-2 and IFNγ production was also assessed. PHA stimulation was used as positive control.

In addition, T cells with substantial Vβ TCR diversity from the engrafted gene targeted HSPC after tumor challenge were also generated 3 weeks after injection of the MDA-MB 231 tumor cell line engineered to express human IL-7, IL-15 and GM-CSF. Analysis of TCR Vβ repertoire was also performed on PBMCs from a healthy donor and used as a reference for polyclonal repertoire. Multiplex PCRs for the 23 different Vβ families were run on 6% polyacrylamide gel and densitometric analysis was performed using ImageQuant TL 7.0 and the frequency distribution of the different complementarity-determining region 3 (CDR3) lengths identified within the indicated Vβ families. As expected from a polyclonal TCR repertoire, all Vβ families displayed a Gaussian distribution of the CDR3 lengths. All the samples analyzed display similar TCR Vβ repertoire distributions, constrained for some families and more polyclonal for others and no significant differences were observed between the GFP+ and GFP− cells.

Figure 4J:
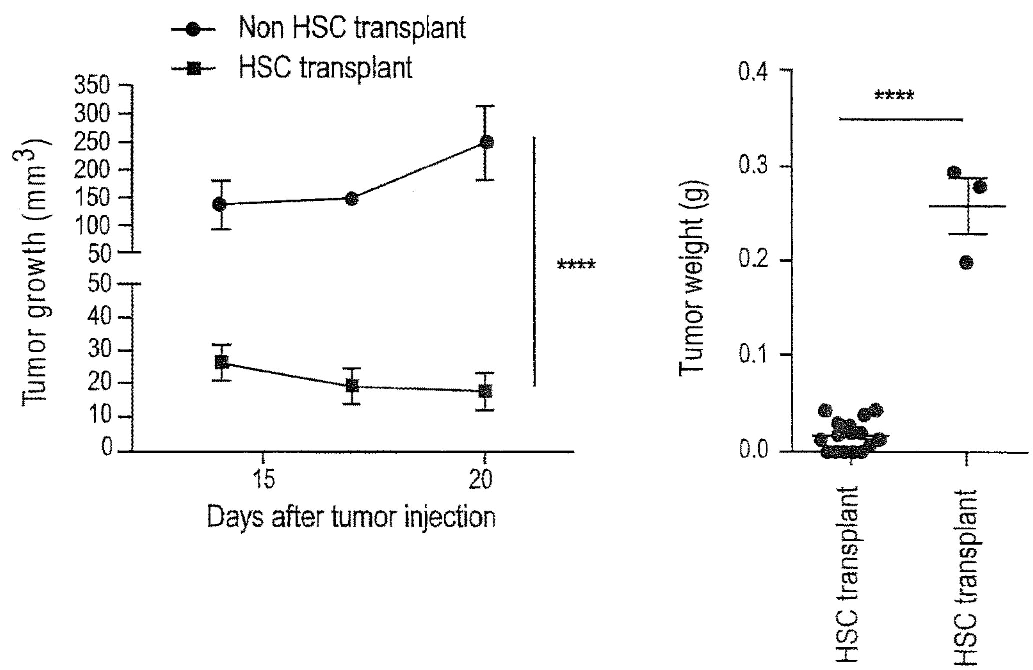

The GFP+ and GFP− T cells expanded ex vivo with the same kinetics in the presence of γ-chain dependent cytokines after polyclonal stimulation and proliferated to a similar extent in response to the allogeneic MDA-MB 231 cell line (FIG. 4J). GFP+ and GFP− T cells were similarly comprised of CD8 and CD4 cell subsets, and a majority of cells showed effector phenotypes. Consistently, both GFP+ and GFP− cells robustly produced γIFN and IL-2 after PMA-ionomycin stimulation or when co-cultured with the allogeneic tumor at different effector/target ratios.

Molecular analyses proved that nearly all GFP+ cells contained targeted integration into the IL2RG genes. We then measured the phosphorylation of two downstream effectors in the signaling cascade of γ-chain coupled receptors. In particular, GFP+ or GFP− T cells from the transplanted mice or T cells from the PB of healthy donor were exposed to the indicated doses of γ-chain related cytokines. The phosphorylation levels of STAT5 on Y694 (pSTATS), STAT3 on Y705 (pSTAT3) and AKT on 5473 (pAKT) were measured by flow cytometry analyses. The targeted T cells displayed similar kinetics and extent of phosphorylation of STATS and AKT as their GFP-counterpart after stimulation with increasing doses of IL-15 and IL-2.

Overall, these data stringently prove functional reconstitution of the edited IL2RG gene, which can support lymphopoiesis and mature T-cell function indistinguishably from the wild-type allele.

Example 6

Nucleotide Modified mRNA

CD34+ cells were analyzed to determine the effect of IDLV or plasmid donor integration on three IFN-I responsive genes (IRF7, OAS1 and RIG1) following ZFN-mediated targeted integration of IDLV and plasmid donors, including when using nucleotide-modified (nec-modified) ZFN mRNA. See e.g. Kormann et al, (2011) *Nature Biotechnology* 29(2):154-157. Briefly, CD34+ cord blood cells were treated as described above and the levels of gene expression of IRF7, OAS1 and RIG1 were evaluated.

Figure 8A:
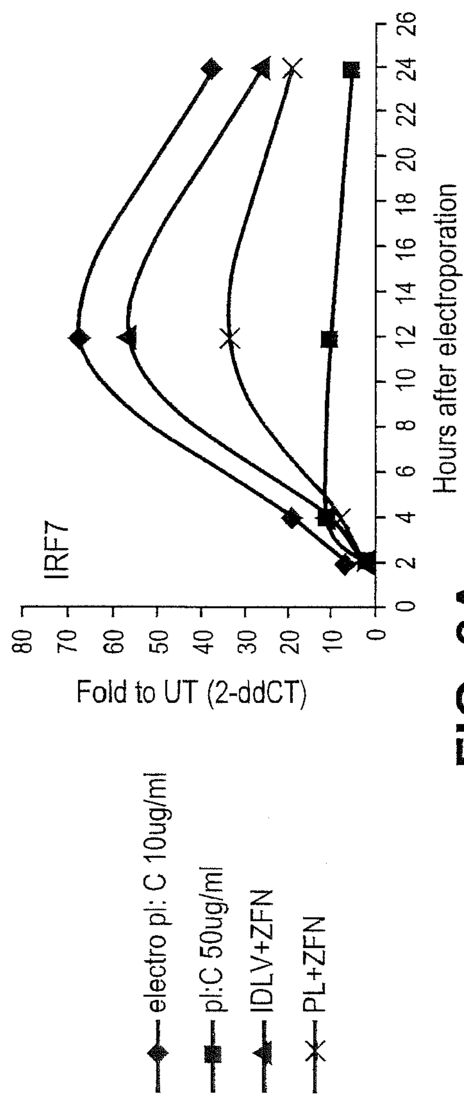
FIGS. 8A through 8C are graphs showing gene expression analysis of three IFN-I responsive genes performed on cord blood derived CD34+ cells at different time points upon positive control treatment with pI:C (50 ug/ml), electroporation of pI:C or AAVS1 gene targeting with an IDLV or a plasmid ("PL") donor.
Figure 8C:
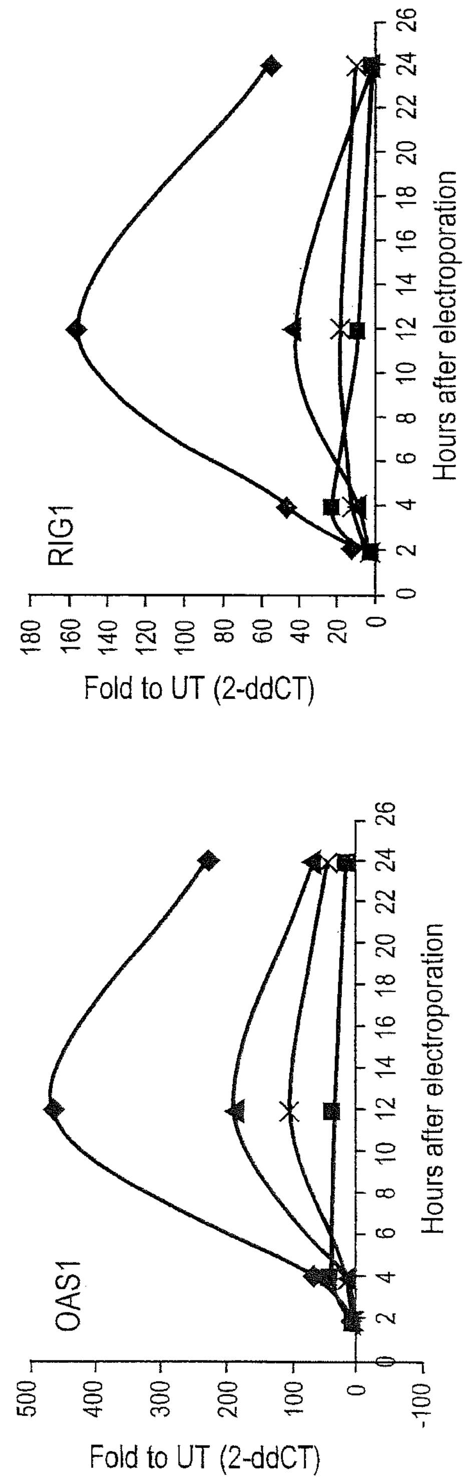
Figure 8B:
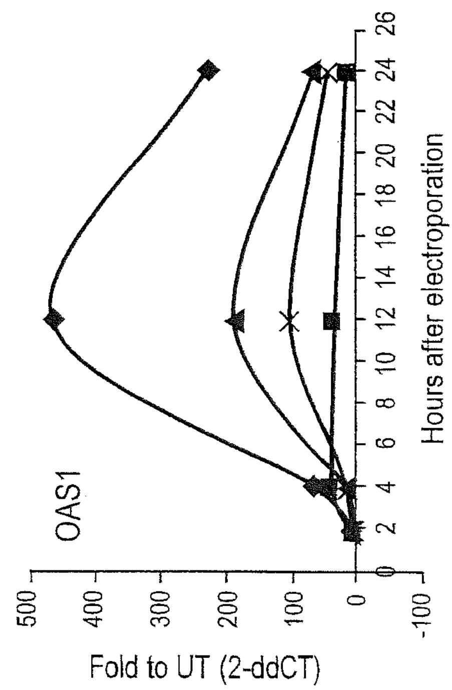
Figure 9:
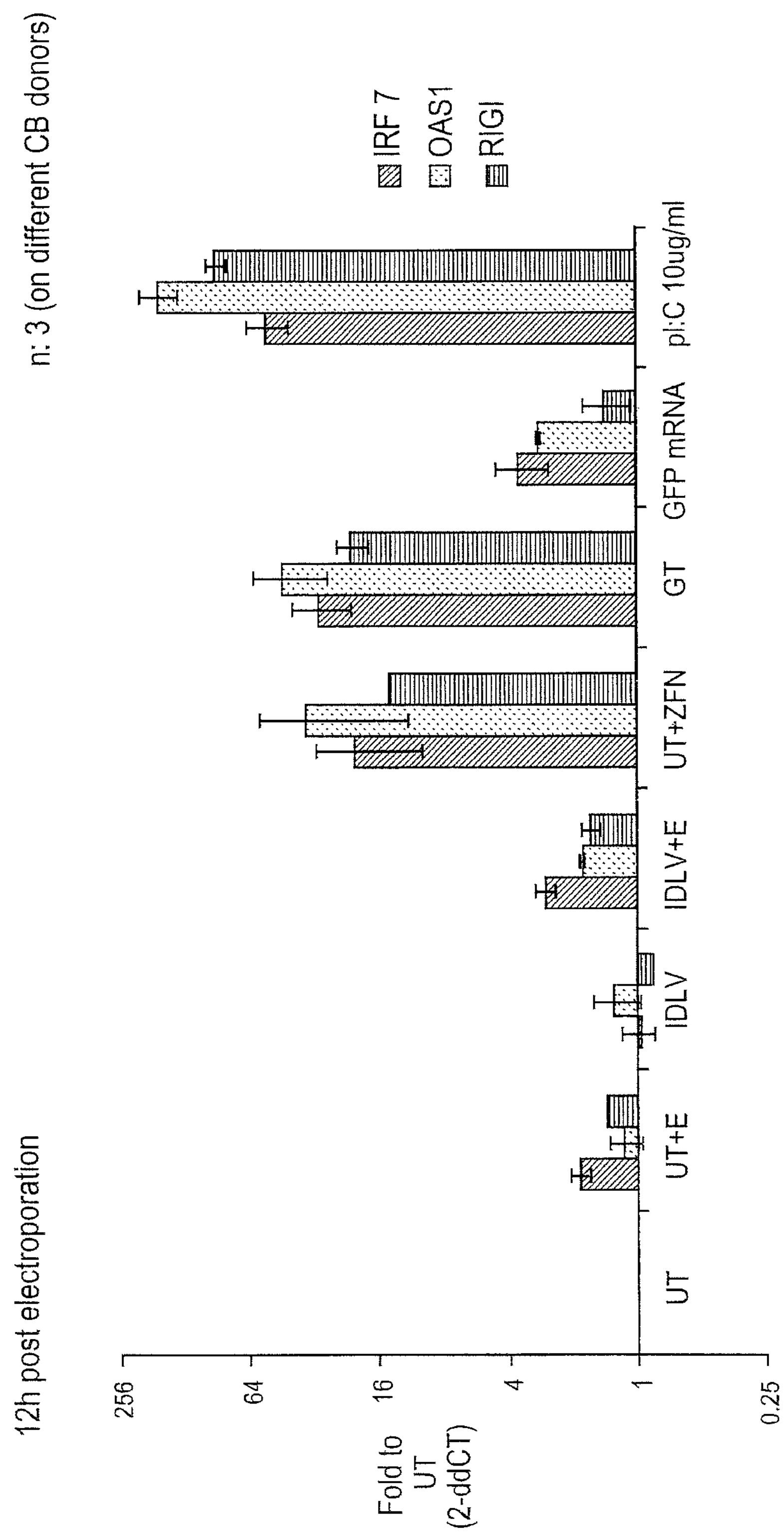
FIG. 9 is a graph showing gene expression analysis of the three IFN-I responsive genes IRF7, OAS1 and RIG1 performed on cord blood derived CD34+ cells. "UT" indicates untransduced; "UT+E": untransduced mock electroporated; "IDLV+E": transduced with IDLV donor and mock electroporated; "UT+ZFN": untransduced electroporated with AAVS1-ZFN mRNAs; "GT": AAVS1 gene targeted cells (IDLV+ZFNs treated); "GFP mRNA": electroporated with GFP encoding mRNA; "pI:C": electroporated with 10 ug/ml. Data shown as the fold increase in gene expression as compared to the UT cells. As shown, electroporation of mRNAs encoding for ZFNs drives IFN-I signaling upregulation.
Figure 10A:
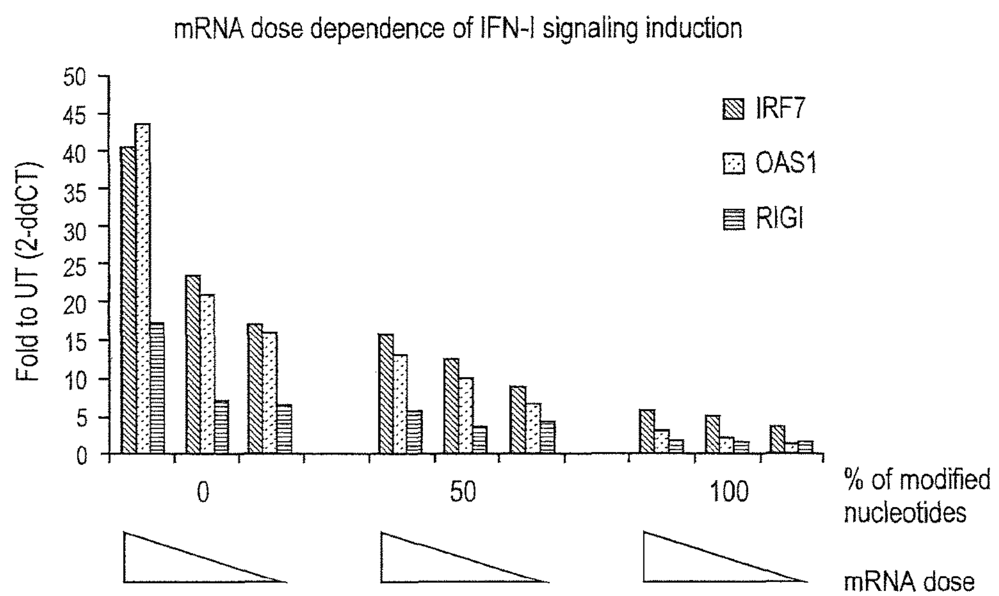
FIGS. 10A and 10B are graphs showing gene expression analysis of IFN-I responsive genes IRF7, OAS1 and RIG1 (FIG. 10A) as well as FACS analysis for GFP expression and NHEJ assay performed on cord blood derived CD34+ cells treated for AAVS1 gene targeting (FIG. 10B) using decreasing doses of ZFN mRNA transcribed in vitro using different percentages of the modified nucleotides pseudouridine (Ψ) and 5-methylcytidine (m5C); 0, 50 or 100% of incorporated modified nucleotides. As shown, corporation of modified nucleotides abrogates IFN-I signaling while having little effect on nuclease cleavage activity and targeted integration.
Figure 10B:
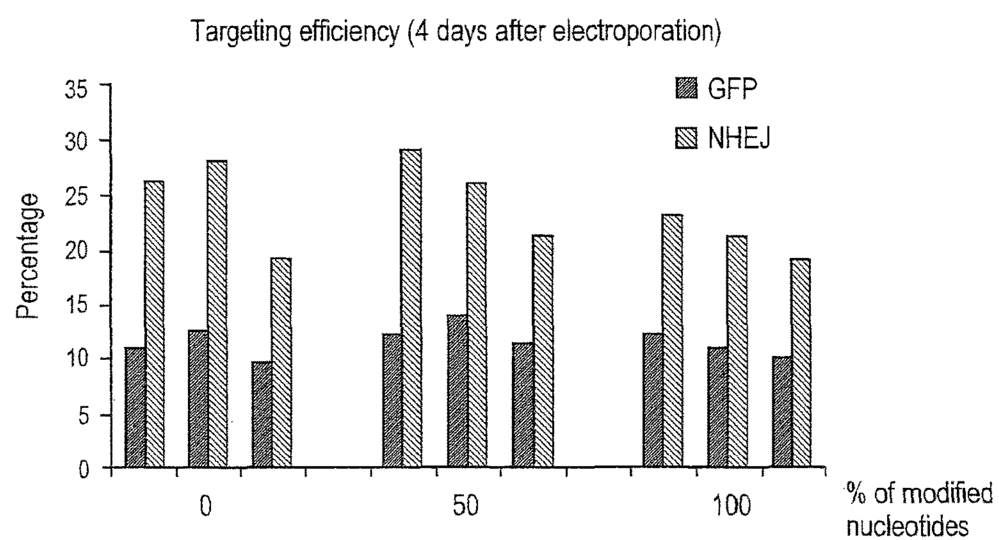

As shown in FIGS. 8 and 9, using mRNA lacking the modified nucleotides, the gene targeting procedure described herein strongly upregulates IFN-I signaling. As shown in FIG. 10, incorporation of modified nucleotides abrogates IFN activation. In this experiment, the ratio of pseudouridine and methylcytidine compared to normal nucleotides are expressed as percentages (i.e., 0%, 50% and 100% are ratios of 0:1, 1:1, 1:0).

Figure 11A:
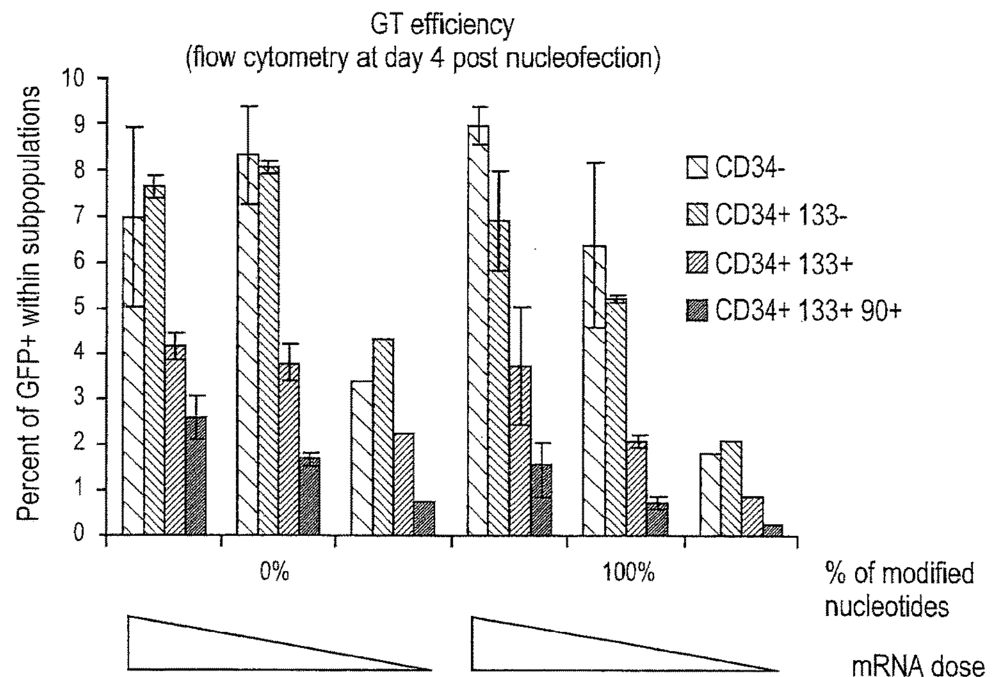
FIGS. 11A and 11B shows mRNA testing on BM-CD34+ cells. FACS analysis for GFP expression (FIG. 11A, gene targeting ("GT") efficiency) and vitality (7AAD, FIG. 11B, Lin+ cells at day 4 post nucleofection) performed on bone marrow derived CD34+ cells treated for AAVS1 gene targeting using decreasing doses of ZFN mRNA transcribed in vitro using different percentages of the modified nucleotides pseudouridine (Ψ) and 5-methylcytidine (m5C).
Figure 11B:
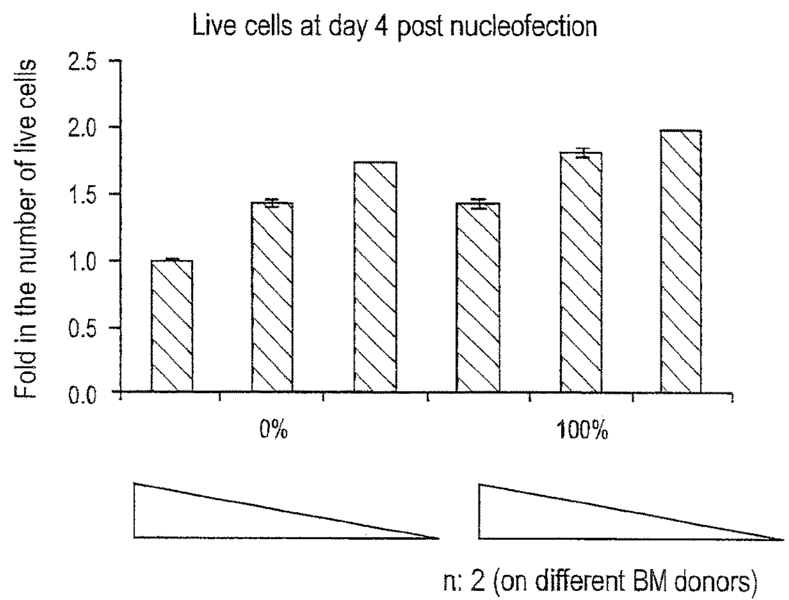

BM-CD34+ cells were also analyzed by FACS analysis for GFP expression and vitality (7AAD) performed on bone marrow derived CD34+ cells treated for AAVS1 gene targeting using decreasing doses of ZFN mRNA transcribed in vitro using different percentages of the modified nucleotides pseudouridine (Ψ) and 5-methylcytidine (m5C). Results are shown in FIG. 11.

Figure 12A:
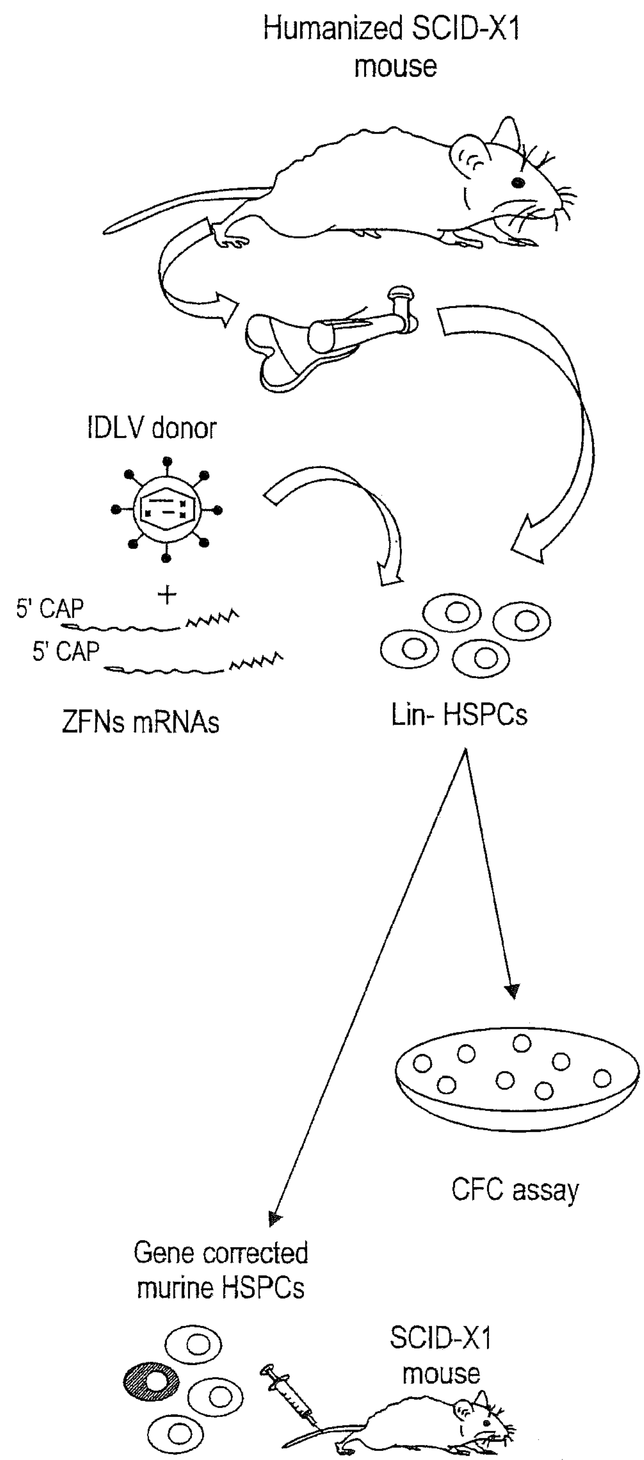
FIG. 12A is an illustration of the methods used. Lineage negative cells were purified from the bone marrow of a transgenic SCID-X1 mouse model carrying a mutated human gene sequence (resulting in 226R->H) in place of the endogenous murine Il2RG gene (FIG. 12B). After 3 h of prestimulation, the cells were transduced with an IDLY donor carrying a corrective IL2RG cDNA followed by a PGK.GFP reporter cassette and electroporated after 24 h with cognate ZFNs mRNA, transcribed in vitro using the modified nucleotides pseudouridine (Ψ) and 5-methylcytidine (m5C) (FIG. 12C).
Figure 12B:
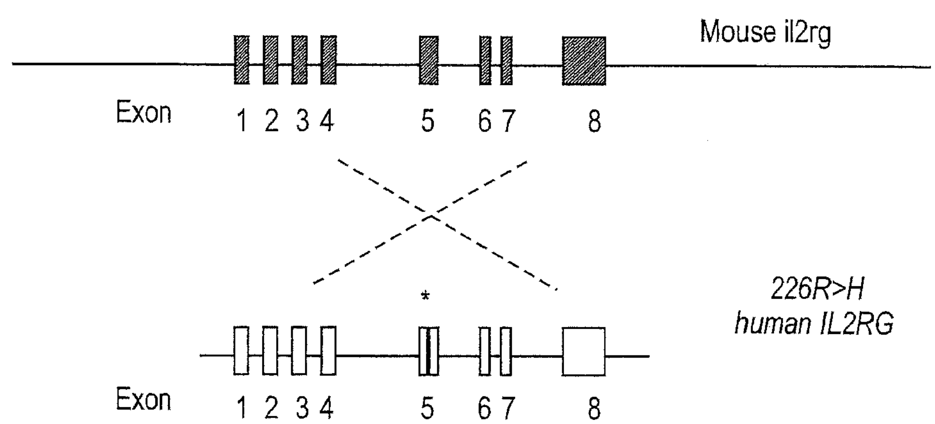
FIGS. 12, panels A to through 12E, show procedures and analysis of targeted gene correction in murine HSC.
FIG. 12D shows the percentages of GFP+ cells measured 5 and 14 days after electroporation on liquid cultures or after plating for the CFC assay and images of cells demonstrating GFP expression.
FIG. 12E shows the treated cells were injected into lethally irradiated SCID-X1 mice 1 day after electroporation. Engraftment of GFP+targeted cells was measured by serial peripheral blood analysis. Gene correction of the IL2RG gene rescued the differentiation of GFP+ HSPC into lymphoid lineages.
Figure 12C:
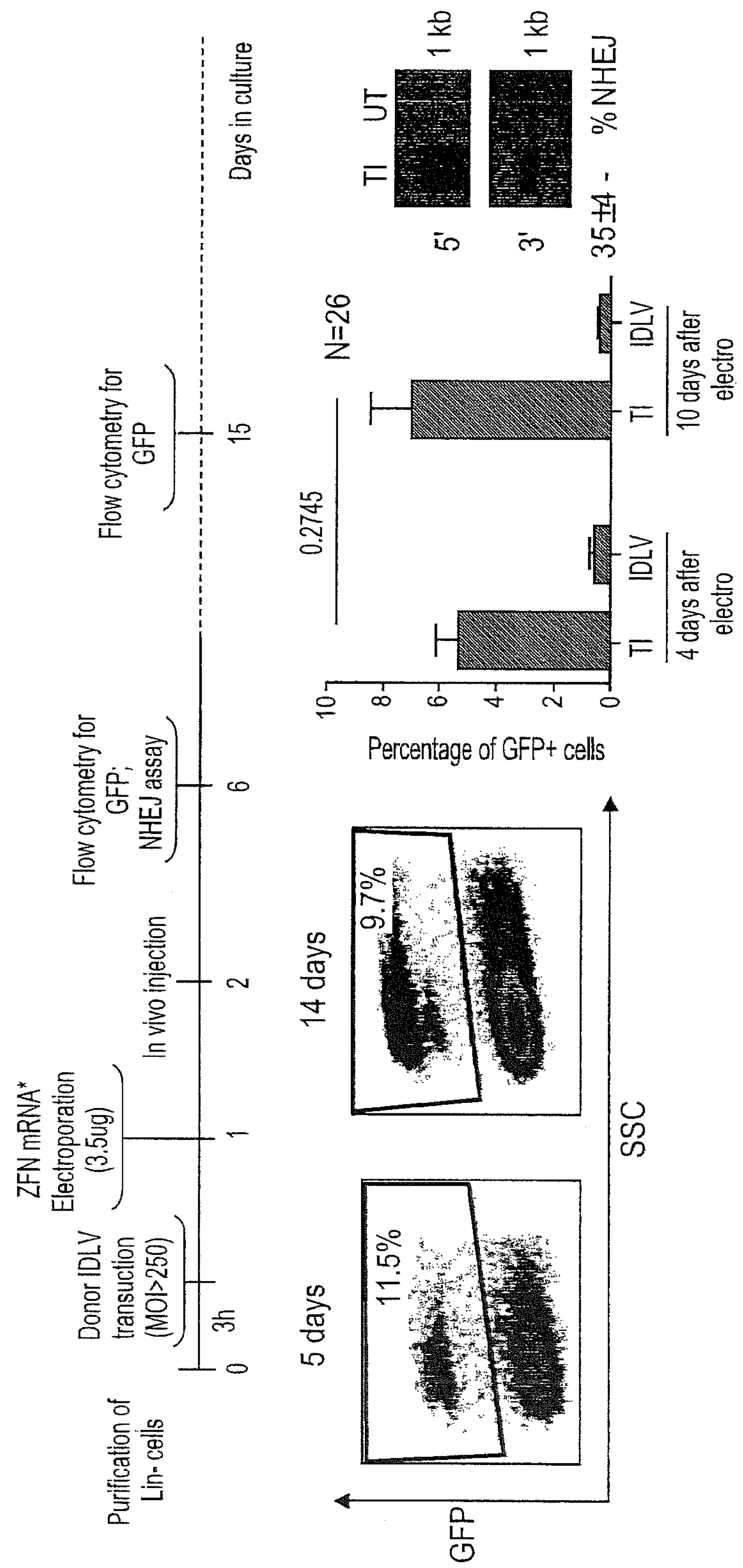

In addition, lineage negative cells were purified from the bone marrow of a transgenic SCID-X1 mouse model carrying a mutated human gene sequence in place of the endogenous murine Il2rg gene (see experimental outline, FIG. 12A). The IL2RG gene in the mouse was replaced by a human IL2RG gene comprising a mutation (226R->H), as shown in FIG. 12B. After 3 h of prestimulation, the cells were transduced with an IDLV donor carrying a corrective IL2RG cDNA followed by a PGK.GFP reporter cassette and electroporated after 24 h with cognate ZFNs mRNA, transcribed in vitro using the modified nucleotides pseudouridine (Ψ) and 5-methylcytidine (m5C) (FIG. 12C).

Figure 12D:
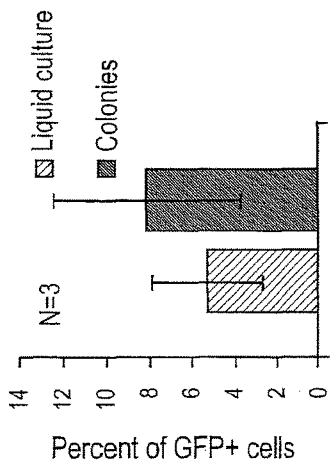
Figure 12D:
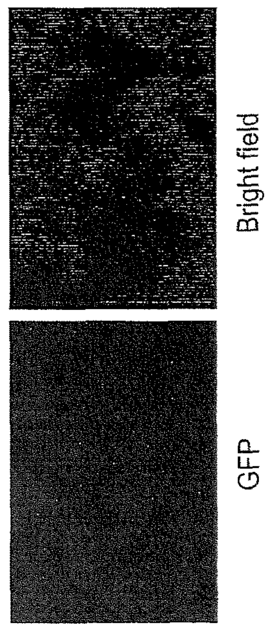
Figure 12D:
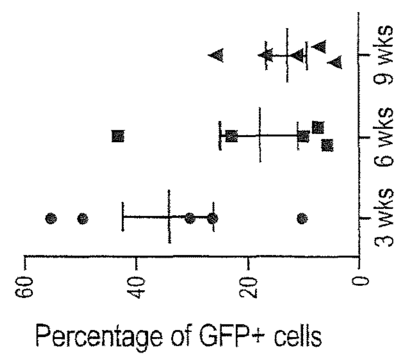
Figure 12E:
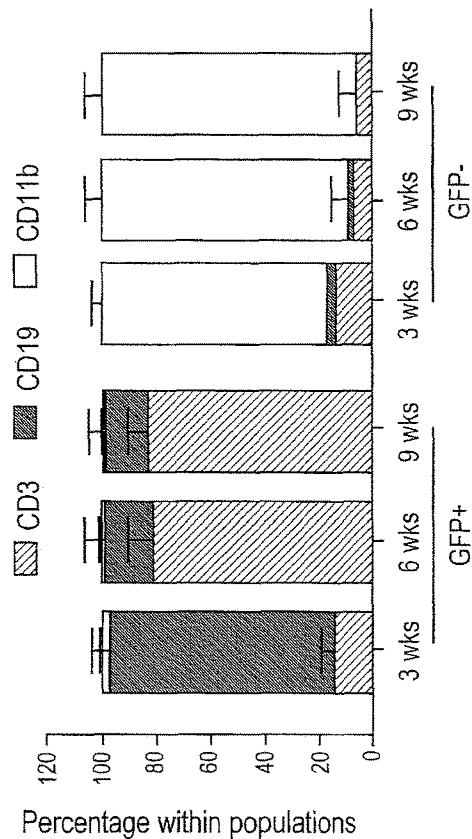

FIG. 12D shows the percentages of GFP+ cells was measured 5 and 14 days after electroporation on liquid cultures or after plating for the CFC assay and results of site specific PCR for the vector-to-genome junctions that confirmed targeted integration. FIG. 12E shows the treated cells were injected into lethally irradiated SCID-X1 mice 1 day after electroporation. Engraftment of GFP+ targeted cells was measured by serial peripheral blood analysis. Gene correction of the IL2RG gene rescued the differentiation of GFP+ HSPC into lymphoid lineages.

Example 7

High Specificity of IL2RG ZFNs on the HSC Genome

An unbiased genome-wide screening in K562 cells to identify potential off target sites of the IL2RG ZFNs to be used in this study was performed as described (Gabriel et al. (2011) *Nat Biotech* 29(9):816-23) found a low but detectable rate of indel accumulation in a small number of genomic loci bearing homology to the intended ZFN target site. We thus determined whether these sites were also affected in the HSPC treated here with ZFNs containing the same IL2RG DNA binding domains but coupled to improved obligate heterodimeric FokI domains. We deep sequenced the genomic regions encompassing the identified potential target sites on treated CD34+ cells cultured in vitro and on human cells harvested from the BM of long-term engrafted NSG mice (3 independent samples each, plus untreated control). Results are shown in Table 2.

TABLE 2

Analysis of off-target sites

| Nearest | | Homology | | NHEJ (%) | | | | | |
|---|---|---|---|---|---|---|---|---|---|
| | | | | In vitro | | | Mouse | | |
| RefSeq gene | In/Ex | (%) | ZFN-Dimer | A | B | G | B2 | C0 | E2 |
| IL2RG | Ex | 100 | L_5_R | 54.60 | 61.18 | 45.60 | 26.08 | 43.51 | 20.07 |
| SCARB1 | Outside | 70.8 | L_5_R | 0.17 | 0.70 | ns | ns | ns | ns |
| SLC31A1 | In | 75 | R_5_L | 0.61 | ns | ns | ns | 0.02 | ns |
| FAM133B | tn | 66.7 | R_6_R | ns | ns | ns | ns | ns | ns |
| KIAA0528 | In | 87.5 | L_5_L | ns | ns | ns | ns | ns | ns |
| SF3B1 | Outside | 66.7 | L_5_L | ns | ns | ns | ns | ns | ns |
| A2BP1 | Outside | 75 | L_5_R | ns | ns | ns | ns | ns | ns |
| ANKFY1 | Ex | 87.5 | L_3_R | ns | ns | ns | ns | ns | ns |
| TRIM43 | Outside | 91.7 | L_4_L | ns | ns | ns | ns | ns | ns |
| SEC16A | Ex | 70.8 | R_6_L | ns | ns | ns | ns | ns | ns |

As shown, whereas the intended IL2RG target site showed a remarkable 45 to 61% indel rate in the in vitro cultured cells and 20 to 43% in the in vivo engrafted cells, we found 0.17 to 0.7% indels in 2 in vitro samples for only the top 2 previously identified off target sites and 0.02% in one of them in an in vivo sample. Deep sequencing of all the other sites gave results not statistically different from the background error rate, which limits the sensitivity of our analysis at 0.01% (see, also Genovese et al. (2014) *Nature* 510, 235-240). The absence of detectable off-target activity at some of these sites is consistent with the adoption of obligate heterodimeric FokI variants in this study, which would detarget activity from sites bearing binding sites for either ZFN homodimer. Our analysis indicated the remarkable specificity of the ZFNs used, as the ratio between activity at the intended target site versus the top identified off target site is ≥100 fold (also considering the concomitant occurrence of HDR at the target site).

Thus, targeted integration in human cord blood and bone marrow HSPCs by long-term multilineage repopulation of transplanted mice was highly specific.

Example 8

IL2RG Gene Correction in BM Derived HSPC from a SCID-X1 Patient

Since treatment of SCID-X1 patients is likely to be provided well after birth, we investigated whether CD34+ cells from BM were amenable to genome editing as shown above for CB derived cells. The optimized protocol developed for CB performed similarly on CD34+ cells form adult BM in terms of overall gene targeting efficiency (mean 6±0.5% measured for 2 genomic loci in 4 different healthy donors), distribution of targeting events among the different progenitor subsets, and the rate of indels induced at the ZFN target sites.

Xenotransplantation proved the long-term multilineage repopulation capacity of the targeted cells, with all transplanted NSG mice bearing GFP+ cells at frequencies comparable to those observed with CB derived cells. Based to these promising results, we then tested our gene correction strategy on BM CD34+ cells from a symptomatic 4-month old SCID-X1 patient bearing a missense mutation in Exon 7 of IL2RG (c.865C>T; R289X).

As expected for this mutation, blood sampling or BM harvest from the patient did not show any T or NK cells. From 3 to 11% of the treated cell progeny became GFP+, depending on primitive versus committed progenitor status. CFC assays yielded 3 GFP+ colonies out of ~100 scored. Flow cytometry showed normal expression of the gamma chain protein in the myeloid progeny of the GFP+ CFCs. PCR analyses of these colonies proved targeted integration into IL2RG leading to expression of the expected fusion transcript bearing the corrective cDNA sequence spliced to the upstream endogenous exons.

Overall, these results showed reconstitution of a functional IL2RG gene upon targeted editing of a SCID-X1 allele in HSPC.

All patents, patent applications and publications mentioned herein are hereby incorporated by reference in their entirety.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method for targeted integration into purified hematopoietic stem cells (HSC) and/or progenitor cells (PC), the method comprising the following steps:

(a) stimulating the cells;

(b) delivering a non-integrating lentiviral (IDLV) donor nucleic acid to the cells one day after stimulation;

(c) culturing the cells obtained by step (b) for one day; and (d) delivering at least one zinc finger nuclease to the cells obtained by step (c) such that the donor nucleic acid is integrated into the genome, wherein the at least one zinc finger nuclease is delivered in mRNA form.

2. The method of claim 1, further comprising treating the HSC and/or PC cells with an aryl Hydrocarbon Receptor Antagonist.

3. The method according to claim 1, wherein the method comprises delivering at least one zinc finger nuclease by electroporation.

4. The method according to claim 1, wherein the donor nucleic acid is an exogenous sequence.

5. The method according to claim 1, wherein the nuclease comprises a pair of ZFNs.

6. The method according to claim 1, wherein the HSC and/or PC cells are selected from the group comprising CD34+ cells, CD34+CD133+ cells, CD34+CD133− cells, CD34+CD133+CD90+ cells, or a combination thereof.

7. The method according to claim 1, wherein the IDLV vector comprises an exogenous sequence flanked by regions of homology to an endogenous locus and the mRNA is delivered by electroporation.

8. The method according to claim 7, wherein the exogenous sequence is integrated into an endogenous safe harbor locus or downstream of the regulatory regions of an endogenous gene, such that expression of the exogenous sequence is driven by the endogenous regulatory regions.

9. The method according to claim 7, wherein the HSC and/or PC cells are selected from the group comprising CD34+ cells, CD34+CD133+ cells, CD 34+CD133− cells and CD34+CD133+CD90+ cells, or combination thereof.

10. The method of claim 1, further comprising the steps of:

(e) culturing the cells of step (d), and (f) isolating the cultured cells of step (e).

11. The method of claim 10, further comprising formulating the isolated cultured cells of step (f) into a pharmaceutical composition and administering the pharmaceutical composition to a subject.

* * * * *

SEQUENCE LISTING

<160> NUMBER OF SEQ ID NOS: 22

<210> SEQ ID NO 1
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
aactctgccc tctaacgctg c 21

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
acgtgaagaa tgtgcgagac ccag 24

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: Synthetic primer

<400> SEQUENCE: 3
ttgcatcgca ttgtctgagt agg 23

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 4
aacggggatg caggggaacg 20

<210> SEQ ID NO 5
<211> LENGTH: 27
<212> TYPE: DNA
<213> ORGANISM: Artificial Sequence
<220> FEATURE:
<223> OTHER INFORMATION: Description of Artificial Sequence: Synthetic primer

<400> SEQUENCE: 5
gctaaggcca agaaagtagg gctaaag 27

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 6
agccagaagt acacgcacag c 21

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
acctctacaa atgtggtatg gctg 24

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ttccttccat caccaaaccc tcttg 25

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
cgagctcggt acctttaaga cc 22

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
gagtcctgcg tcgagagag 19

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
cttcaggaca gcatgtttgc 20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
acaggaggtg ggggttagac 20

```
<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13

ttctcccttc tctcatagac accc                                            24


<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14

ctcatggatt gggtcatgtg g                                               21


<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15

tcctccttcc ccgttgccag tctc                                            24


<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16

gcagcgttag agggcagagt tc                                              22


<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17

agggatactg tgggacattg gag                                             23


<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18

aggtccttct atctgtctgg ttg                                             23
```

-continued

```
<210> SEQ ID NO 19
<211> LENGTH: 25
<212> TYPE: DNA
<213> ORGANISM: Homo sapiens

<400> SEQUENCE: 19

ctgacctctt ctcttcctcc cacag                                        25


<210> SEQ ID NO 20
<211> LENGTH: 13
<212> TYPE: DNA
<213> ORGANISM: Homo sapiens

<400> SEQUENCE: 20

tttctctcca cag                                                     13


<210> SEQ ID NO 21
<211> LENGTH: 10
<212> TYPE: DNA
<213> ORGANISM: Unknown
<220> FEATURE:
<223> OTHER INFORMATION: Description of Unknown: Kozak sequence

<400> SEQUENCE: 21

gccaccatgg                                                         10


<210> SEQ ID NO 22
<211> LENGTH: 9
<212> TYPE: PRT
<213> ORGANISM: Homo sapiens

<400> SEQUENCE: 22

Leu Ala Gly Leu Ile Asp Ala Asp Gly
1               5
```